US010870865B2

(12) United States Patent
Bouille et al.

(10) Patent No.: US 10,870,865 B2
(45) Date of Patent: Dec. 22, 2020

(54) PARTICLE FOR THE ENCAPSIDATION OF A GENOME ENGINEERING SYSTEM

(71) Applicant: FLASH THERAPEUTICS, Toulouse (FR)

(72) Inventors: Pascale Bouille, Vincennes (FR); Régis Gayon, Ramonville Saint-Agne (FR); Lucille Lamouroux, Pinsaguel (FR); Alexandra Iche, Corronsac (FR)

(73) Assignee: FLASH THERAPEUTICS, Toulouse (FR)

( * ) Notice: Subject to any disclaimer, the term of this patent is extended or adjusted under 35 U.S.C. 154(b) by 6 days.

(21) Appl. No.: 16/301,317

(22) PCT Filed: May 12, 2017

(86) PCT No.: PCT/FR2017/051164
§ 371 (c)(1),
(2) Date: Nov. 13, 2018

(87) PCT Pub. No.: WO2017/194902
PCT Pub. Date: Nov. 16, 2017

(65) Prior Publication Data
US 2020/0071720 A1 Mar. 5, 2020

(30) Foreign Application Priority Data

May 13, 2016 (FR) .................................. 16 54332
Oct. 24, 2016 (FR) .................................. 16 60309
Mar. 31, 2017 (FR) .................................. 17 52818

(51) Int. Cl.
A61K 39/21 (2006.01)
C12N 7/00 (2006.01)
A61K 38/00 (2006.01)
A61K 39/00 (2006.01)
A61K 39/12 (2006.01)
C12N 15/86 (2006.01)
C07K 14/005 (2006.01)
C12N 15/90 (2006.01)

(52) U.S. Cl.
CPC ............ C12N 15/86 (2013.01); C07K 14/005 (2013.01); C12N 7/00 (2013.01); C12N 15/907 (2013.01); C07K 2319/735 (2013.01); C07K 2319/85 (2013.01); C12N 2310/20 (2017.05); C12N 2740/16023 (2013.01); C12N 2740/16043 (2013.01); C12N 2740/16052 (2013.01); C12N 2795/18122 (2013.01); C12N 2800/24 (2013.01); C12N 2800/30 (2013.01); C12N 2800/50 (2013.01)

(58) Field of Classification Search
CPC ...................... C12N 15/86; C12N 7/00; C12N 2740/13043; A61K 38/00; C07K 14/47
See application file for complete search history.

(56) References Cited

FOREIGN PATENT DOCUMENTS

WO  2007072056 A2  6/2007

OTHER PUBLICATIONS

Prel et al., "Highly efficient in vitro and in vivo delivery of functional RNAs using new versatile MS2-chimeric retrovirus-like particles", Molecular Therapy—Methods & Clinical Development, 2015, 2:1-15.*
Prel et al., "Highly efficient in vitro and in vivo delivery of functional RNAs using new versatile MS2-chimeric retrovirus-like particles", Molecular Therapy—Methods & Clinical Development, 2015:1-15.*
Chen, Haifeng, Adeno-associated virus vectors for human gene therapy, World Journal of Medical Genetics, Aug. 27, 2015, pp. 28-45, vol. 5(3).
Anne Prel et al: "Highly efficient in vitro and in vivo delivery of functional RNAs using new versatile M52-chimeric retrovirus-like particles", Molecular Therapy—Methods & Clinical Development, pp. 1-16, (Oct. 2015).
Anne Prel et al: Highly efficient in vitro and in vivo delivery of functional RNAs using new versatile M52-chimeric retrovirus-like particles: Supplementary Figures S2, Molecular Therapy—Methods & Clinical Development, pp. 1, (Oct. 2015).
Michael R. Williams et al: A Retroviral CRISPR-Cas9 System for Cellular Autism-Associated Phenotype Discovery in Developing Neurons', Scientific Reports, pp. 1-12 (May 2016).
Shefah Qazi et al: "Programmed Self-Assembly of an Active P22-Cas9 Nanocarrier System", Molecular Pharmaceutics, pp. 1191-1196, vol. 13, No. 3 (Mar. 2016).

* cited by examiner

Primary Examiner — Barry A Chestnut
(74) Attorney, Agent, or Firm — Browdy and Neimark, PLLC

(57) ABSTRACT

The present invention relates to a retroviral particle comprising a protein derived from the Gag polyprotein, an envelope protein, optionally an integrase and at least two encapsidated non-viral RNAs, the encapsidated non-viral RNAs each comprising an RNA sequence of interest bound to an encapsidation sequence, each encapsidation sequence being recognized by a binding domain introduced into the protein derived from the Gag polyprotein and/or into the integrase, and at least one of said sequences of interest of the encapsidated non-viral RNAs comprises a part coding a nuclease.

17 Claims, 25 Drawing Sheets
Specification includes a Sequence Listing.

pcDNA-EF1-Cas9-MS2 12X

Linear p8.74ΔZF-MS2 Coat pEnv pILV-EF1-Cas9-WPRE pILV-EF1-GFP-WPRE pILV-H1-GuideU3-U6-GuideD1-WPRE pILV-H1/U6-GuideD1-WPRE linear p8.74 pcDNA-H1-GuideD1-MS2 2X pcDNA-H1-GuideD1Chimeric-MS2 2X pcDNA.EF1.PPRV.TALEN 5'.WPRE.MS2(12X)

pILV.EF1.TALEN 5' pILV.EF1.TALEN 3'

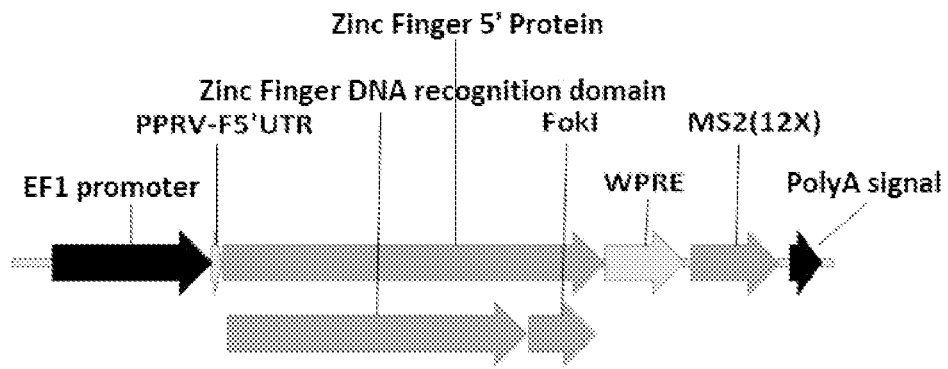
pcDNA.EF1.PPRV. ZFP 5'.WPRE.MS2(12X)
Figure 15a
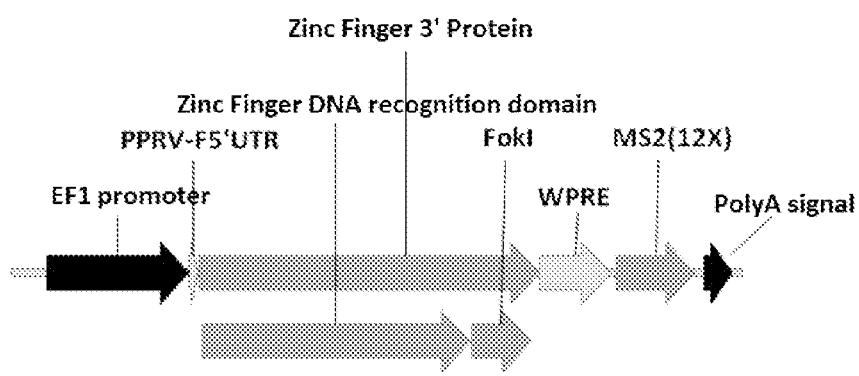
pcDNA.EF1.PPRV.ZFP pILV.EF1.ZFP 5' pILV.EF1.ZFP 3' linear pcDNA.EF1.PP7 12X

Linear P8.74- Pol-PP7 Coat

Linear p8.74- Pol-PP7 Coat pcDNA-U6-GuideD1Chimeric-MS2 2X pcDNA-U6-Guide_antiPD1Chimeric-MS2 2X pcDNA-U6-Guide-antiCXCR4Chimeric-MS2 2X pILV-H1/U6-GuideantiPD1-WPRE pcDNA-EF1-Cas9-PP7 2X pcDNA-U6-GuideD1Chimeric-PP7 2X pcDNA.EFI.FluorescentReporter.MS2 12X pcDNA.EFI.FluorescentReporter.PP7 2X pILV-EF1-ZsGreenI-WPRE

SEQUENCE LISTING

```
<160> NUMBER OF SEQ ID NOS: 7

<210> SEQ ID NO 1
<211> LENGTH: 32
<212> TYPE: DNA
<213> ORGANISM: Artificial Sequence
<220> FEATURE:
<223> OTHER INFORMATION: Synthetic

<400> SEQUENCE: 1
ctagaaaaca tgaggatcac ccatgtctgc ag                                   32

<210> SEQ ID NO 2
<211> LENGTH: 38
<212> TYPE: DNA
<213> ORGANISM: Artificial Sequence
<220> FEATURE:
<223> OTHER INFORMATION: Synthetic

<400> SEQUENCE: 2
ctagaaagga gcagacgata tggcgtcgct ccctgcag                             38
```

```
<210> SEQ ID NO 3
<211> LENGTH: 34
<212> TYPE: DNA
<213> ORGANISM: Artificial Sequence
<220> FEATURE:
<223> OTHER INFORMATION: Synthetic

<400> SEQUENCE: 3
ggccaacatg aggatcaccc atgtctgcag ggcc                                    34

<210> SEQ ID NO 4
<211> LENGTH: 38
<212> TYPE: DNA
<213> ORGANISM: Artificial Sequence
<220> FEATURE:
<223> OTHER INFORMATION: Synthetic

<400> SEQUENCE: 4
ctagaaacca gcagagcata tgggctcgct ggctgcag                                38

<210> SEQ ID NO 5
<211> LENGTH: 25
<212> TYPE: DNA
<213> ORGANISM: Artificial Sequence
<220> FEATURE:
<223> OTHER INFORMATION: Synthetic

<400> SEQUENCE: 5
ggagcagacg atatggcgtc gctcc                                              25

<210> SEQ ID NO 6
<211> LENGTH: 25
<212> TYPE: DNA
<213> ORGANISM: Artificial Sequence
<220> FEATURE:
<223> OTHER INFORMATION: Synthetic

<400> SEQUENCE: 6
ccagcagagc atatgggctc gctgg                                              25

<210> SEQ ID NO 7
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(14)
<223> OTHER INFORMATION: n is a, c, g, or t

<400> SEQUENCE: 7
ggatgnnnnn nnnn                                                          14
```

PARTICLE FOR THE ENCAPSIDATION OF A GENOME ENGINEERING SYSTEM

The Sequence Listing in ASCII text file format of 1826 bytes in size, created on May 8, 2019, with the file name "2019-05-14SequenceListing_Bouille3," filed in the U.S. Patent and Trademark Office on even date herewith, is hereby incorporated herein by reference.

The present invention relates to a retroviral system for transferring non-viral RNAs into target cells and more particularly a retroviral particle capable of delivering multiple RNAs. The invention also relates to compositions comprising these retroviral particles, kits for producing the latter, the associated manufacturing methods as well as the uses of the particles and compositions.

Introduction of multiple RNAs into a target cell is a major challenge in research and development and in gene therapy.

The use of vectors derived from viruses has become a crucial method for gene transfer. Currently, viral vectors can be divided into two main categories:

integrative vectors, which integrate into the recipient genome, and non-integrative vectors, which usually form an extrachromosomal genetic element.

The integrative vectors such as the gamma-retroviral vectors (RV) and lentiviral vectors (LV) are integrated stably. The non-integrative vectors, such as the adenoviral vectors (ADV) and the adeno-associated vectors (AAV) are quickly eliminated from the rapidly dividing cells. Certain factors influencing the choice of a particular vector comprise its encapsidation capacity, its range of target or host cells, its gene expression profile, its transduction effectiveness and its capacity for inducing an immune response, which is particularly problematic if repeated transductions are necessary.

Certain applications require the use of non-integrative vectors such as in gene therapy or in many in vitro, ex vivo and in vivo applications. As examples, there may be mentioned:

induction of the reprogramming of specialized cells into pluripotent cells, as well as induction of the differentiation of stem cells or pluripotent cells into specialized cells, expression of antigens or of proteins (toxic or non-toxic) simultaneously in a target cell, expression of genome engineering systems such as for example CRE protein, TALEN systems, Zn Finger Nuclease or CRISPR, or of any other system requiring expression of protein or of RNA.

One way of introducing RNAs into a target cell employs viral vectors based on viruses belonging to the family Retroviridae (also denoted Retrovirus family or RNA viruses). In fact, during its replication cycle, a virus of the family Retroviridae has the capacity to convert its genome, constituted by RNA, into double-stranded DNA, which will be integrated into the genome of the target cell. Particular examples of this family of Retroviruses are the gamma-retroviruses and the lentiviruses.

The replication cycle of a retrovirus comprises a first phase of recognition of the target (or host) cell via fixation to a membrane receptor. This recognition phase leads, after membrane fusion, to entry of the retrovirus into the host cell. The retroviral RNA is then copied into double-stranded DNA by reverse transcriptase, encoded by the retrovirus, then integrated into the genome of the host cell. This viral genome is then transcribed and translated by the host cell, like all the other genes of the cell. This genome codes all of the proteins and sequences allowing the production of other viruses.

More particularly, three genes are common to all of the retroviruses: gag, pol and env.

Gag is a gene coding a polyprotein, the proteins derived from this polyprotein by cleavage being structural proteins involved in assembly of the viruses during replication. These structural proteins are more specifically the matrix (MA) protein, the capsid (CA) protein and the nucleocapsid (NC) protein.

Pol is a gene coding the enzymes integrase, reverse transcriptase and protease.

Env is a gene coding envelope glycoproteins.

These three genes therefore make it possible to copy the retroviral RNA into double-stranded DNA, integrate this DNA into the genome of the host cell and then generate the structure of the neo-synthesized retroviruses: envelope, capsid and nucleocapsid proteins. However, for the neo-synthesized retroviruses to be complete, it is necessary to encapsidate two copies of the retroviral RNA in each of these structures. This encapsidation of two copies of the retroviral RNA in the structure is accomplished by the recognition, by the nucleocapsid protein, of an encapsidation sequence called Psi (for Packaging Signal) carried by the copy of the retroviral RNA.

When a viral vector derived from a retrovirus is used for purposes of gene therapy, at least one part of the coding regions of gag, pol and/or env is dissociated between the encapsidation system and the expression system of the sequence of interest. The gag and pol coding sequences, for example, are carried by the encapsidation plasmid supplying in trans the proteins necessary for the production of viral vectors. The encapsidation sequence and the sequence of interest are carried by independent systems, in order to make the retrovirus non-replicative.

However, in certain cases, integration of the RNA sequence of interest randomly into the genome of the host cell may interrupt an open reading frame and block the expression of important genes. Moreover, for certain applications, such as cell reprogramming or differentiation of stem cells, it is recommended that the expression of a sequence of interest should be carried out in a transient manner.

Application WO2007/072056 describes a viral vector system comprising env, gag, optionally gag/pol as well as an RNA sequence containing a heterologous encapsidation signal that is recognized by a corresponding RNA binding domain associated with gag or with gag/pol. This system is described in the application as being non-integrative and allowing transient expression.

However, such systems are still of limited effectiveness. In particular, for a target cell to express an RNA of interest carried by these systems, it is generally necessary to introduce several copies of this RNA of interest into the cell and consequently use high multiplicities of infection ("multiplicity of infection", MOI). The MOI corresponds to the ratio of the number of vector systems introduced to the number of cells to be infected. A high MOI in fact makes it possible to introduce several copies of the RNA of interest into the cells, allowing one and the same cell to undergo several infections. Now, although it makes it possible to improve the expression level of the RNA of interest that is carried, because of the multiple infections that the cell undergoes, the use of high MOIs also gives rise to some toxicity.

As mentioned above, this type of system is also of interest for genome engineering, and in particular for applications in gene therapy.

At present, introduction of genome engineering systems into target cells is still complex and constitutes a major challenge for the successful implementation of the genome engineering systems mentioned above.

In fact, for a genome engineering system to be able to function, as a minimum, an enzyme capable of cleaving DNA, or nuclease, needs to be introduced into the target cell. Applications in gene therapy further require specificity of DNA cleavage for precisely targeting a given gene, without causing unwanted cleavage. Thus, for use of the TALEN, ZnFinger and CRISPR systems, it is generally necessary to introduce a recognition element into the DNA. Consequently, such systems require at least one nuclease, and preferably two constitutive elements of the engineering system in question, to be introduced into the transduced cells.

Furthermore, these genome engineering systems must take account of parameters such as the duration and the intensity of expression of the genetic material introduced into the target cell, to allow satisfactory effectiveness of the system without inducing toxicity.

The current methods for delivery of these genome engineering systems are mainly.
- transfection of DNA,
- electroporation of RNA, and
- the use of viral vectors.

However, each of these methods has serious drawbacks.

In fact, transfection of DNA is a method that has very low effectiveness on primary or sensitive cells, owing to high toxicity linked to the transfer of DNA, the presence of bacterial sequences in the plasmids and/or random integration of the plasmids into the genome of the transfected cells.

For its part, electroporation of messenger RNA is a method that is preferably used ex vivo, in primary or sensitive cells, but this too does not give good results in terms of effectiveness owing to high toxicity resulting from destabilization of the membranes of the target cells.

The use of viral vectors seems be the most promising method for increasing the effectiveness of delivery, while minimizing cytotoxicity. However, although the lentiviral vectors are effective tools, they integrate into the genome of the target cells to give stable expression of the transgene, which may lead to uncontrolled reactions. Furthermore, the integration deficient lentiviral vectors (IDLV) may be used in order to limit the duration of expression of the nuclease, but they do not guarantee complete absence of integration into the genome of the target cells.

The other alternative is to use AAV adenoviral systems for applications in vivo, but this type of tool involves the use of a nuclease of reduced size because the encapsidation capacity of the adenoviral systems is limited to a size under 4.8 kb, incompatible with the CRISPR or TALEN systems (Chen, 2015).

Therefore there is still a need for viral vector systems that are more efficient and less toxic.

The work of the inventors has made it possible to devise a vector system capable of delivering several RNAs of interest into one and the same cell in a single infection.

The present invention therefore relates to a retroviral particle comprising a protein derived from the Gag polyprotein, an envelope protein, optionally an integrase and at least two encapsidated non-viral RNAs, the encapsidated non-viral RNAs each comprising an RNA sequence of interest bound to an encapsidation sequence, each encapsidation sequence being recognized by a binding domain introduced into the protein derived from the Gag polyprotein and/or into the integrase, and at least one of said sequences of interest of the encapsidated non-viral RNAs comprises a part coding a nuclease.

The retroviral particle according to the invention makes it possible to introduce at least two non-viral RNAs, preferably 3, into a cell by a single infection. These particles may be introduced into the cells by an in vivo, in vitro or ex vivo method.

By "protein derived from the Gag polyprotein" is meant any protein resulting from cleavage of the Gag polyprotein. More particularly, it is a nucleocapsid protein, a matrix protein (for example, in retroviral particles derived from the murine viruses of the MoMuLV type) or protein p12, specific to the gammaretroviruses.

By "envelope protein" is meant any envelope protein, including a pseudotyping envelope protein. As an example, there may be mentioned the Ampho envelope protein, the ecotropic envelope protein, the envelope protein of the Moloney murine leukaemia virus (MoMuLV), the envelope protein of the feline immunodeficiency virus (FIV), the envelope protein of the Harvey murine sarcoma virus (HaMuSV), the envelope protein of the murine mammary tumour virus (MuMTV), the envelope protein of the Rous sarcoma virus (RSV), the envelope protein of the measles virus (MV), the envelope protein of the Gibbon ape leukaemia virus (GALV), the protein of the feline endogenous virus (RD114) or the envelope protein of the vesicular stomatitis virus (VSV-G). More particularly, the envelope protein is the Ampho envelope protein, the ecotropic envelope protein, the envelope protein of the Moloney murine leukaemia virus (MoMuLV), the envelope protein of the feline immunodeficiency virus (FIV), the envelope protein of the Harvey murine sarcoma virus (HaMuSV), the envelope protein of the murine mammary tumour virus (MuMTV), the envelope protein of the Rous sarcoma virus (RSV), the envelope protein of the measles virus (MV), the envelope protein of the Gibbon ape leukaemia virus (GALV) or the envelope protein of the vesicular stomatitis virus (VSV-G). The envelope protein may thus be modified for targeting certain cellular types or certain applications (use of surface receptors as envelope protein).

It is also possible to modify the envelope protein with an antibody, a glycolipid and/or a particular ligand in order to target a particular receptor and/or cellular type.

Preferably, the envelope protein is the VSV-G protein.

By "integrase" is meant the enzymatic protein encoded by the pol gene, which allows integration of the retroviral DNA in the DNA of the cell infected by the retrovirus during replication of said retrovirus.

By "encapsidation sequence" is meant an RNA motif (sequence and three-dimensional structure) recognized specifically by a binding domain. Preferably, the encapsidation sequence is a stem-loop motif. Even more preferably, the encapsidation sequence of the retroviral particle is the stem-loop motif of the RNA of the MS2 bacteriophage or of the PP7 phage such as, for example, that resulting from the sequence ctagaaaacatgaggatcacccatgtctgcag (SEQ ID No.1) or (ctagaaaggagcagacgatatggcgtcgctccctgcag SEQ ID No.2) respectively. The stem-loop motif and more particularly the stem-loop motif of the RNA of the MS2 bacteriophage or that of the RNA of the PP7 phage may be used alone or repeated several times, preferably from 2 to 25 times, more preferably from 2 to 18 times, for example from 6 to 18 times.

By "binding domain" is meant all or part of a protein binding specifically to the encapsidation sequence bound to the RNA sequence of interest. More particularly, it is a mutant or non-mutant protein, defined by a three-dimensional structure, binding specifically to the encapsidation sequence. Preferably, the binding domain is a heterologous domain. More preferably, the binding domain is the Coat protein of the MS2 bacteriophage, of the PP7 phage or of the Q3 phage, the prophage HK022 Nun protein, the U1A protein or the hPum protein.

More preferably, the binding domain is the Coat protein of the MS2 bacteriophage or of the PP7 phage.

Even more preferably, when the binding domain is the Coat protein of the PP7 phage, the latter's sequence is deficient for self-assembly, owing to a deletion of amino acids 67 to 75 (PCPΔFG) (Chao et al. 2008). Preferably, the sequence of the Coat protein of the PP7 phage is codon-optimized for human cells, i.e. the DNA bases are selected for coding amino acids preferentially present in the human species.

By "each sequence" is meant that the encapsidation sequences may be identical or different, depending on whether these encapsidation sequences are recognized by an identical or different binding domain. In fact, the retroviral particle according to the invention may comprise one or more binding domains. When several binding domains are introduced, they may be introduced into the Gag polyprotein and/or into the integrase.

The binding domain allows not only recognition of the encapsidation sequence but also the encapsidation of the RNAs carrying the encapsidation sequence into the particle (or in the present case, of a non-viral RNA bound to an encapsidation sequence).

By "encapsidation" is meant the packaging of an RNA in the viral capsid of a viral particle. It should be noted that in the present invention, encapsidation of non-viral RNAs is carried out by the recognition of a non-viral encapsidation signal, in particular other than Psi.

By "sequence of interest" is meant a sequence coding or having a function that is of interest for the user. More particularly, the sequence of interest carried by each of the two encapsidated non-viral RNAs may be identical or different.

Using the particles according to the invention, it is possible to transfer identical or different non-viral RNAs into target cells.

As the encapsidated RNAs are non-viral, these RNAs do not have the recognition sites of the proteins encoded by the pol gene.

In fact, these non-viral RNAs are not included in the early steps of the replication cycle of the retroviruses, namely:
  copying of the single-stranded viral RNA into double-stranded DNA by reverse transcriptase;
  maturation of the double-stranded viral DNA by recognition of the LTR ends by integrase and maturation of the cytoplasmic pre-integration complex into a nuclear pre-integration complex.

These viral proteins (reverse transcriptase, integrase), encoded by the pol gene, are therefore optional in the particle and the pol gene may therefore either be present, or deleted partially or totally. Preferably, the pol gene is either present, or deleted partially.

It should be noted that the retroviral particles according to the invention comprise genetic material that is both viral and non-viral:

the gag gene, which may be viral or chimeric. More particularly, the gag gene is chimeric when the binding domain or domains is/are introduced into the latter.

optionally, the pol gene, which may be viral or chimeric. As the pol gene codes several enzymes, the sequences relating to these enzymes may be deleted totally or partially, present and non-functional, or present and functional. More particularly, the pol gene is chimeric when the binding domain or domains is/are introduced into the integrase.

at least two non-viral RNAs, each non-viral RNA bearing a sequence of interest and an encapsidation sequence. More particularly, these non-viral RNAs are devoid of any viral sequence.

More specifically, the retroviral particles according to the invention make it possible to introduce, into target cells, RNAs capable of inducing:
  transfer of one or more endogenous or exogenous coding sequences of interest of the target cell,
  transfer of one or more non-coding RNAs such as RNAs capable of inducing an effect on genetic expression, for example by means of shRNA, miRNA, sgRNA, LncRNA or circRNA.
  transfer of cellular RNAs, of the messenger RNA type or others (miRNA etc.), subgenomic replicons of RNA viruses (HCV, etc.) or of complete genomes of RNA viruses,
  simultaneous expression of endogenous or exogenous coding or non-coding sequences of the target cell,
  participation in modification of the genome of the target cell by genome engineering systems, for example the CRISPR system.

By "nuclease" is meant an enzyme having the capacity to cleave one or two strands of DNA, a nuclease having the capacity to initiate cleavage of a phosphodiester bond of the nucleic acids of two nucleotides.

Advantageously, the nuclease is an endonuclease, i.e. it cuts the DNA strand inside the latter.

The nuclease may moreover generate sticky ends or non-sticky ends. Advantageously, it generates sticky ends.

The nuclease may be in its native form (WT), in a mutated form, in an optimized form, in a truncated form or a knock-out form. It is in fact possible to mutate the native nuclease to knock out its capacity for cleaving the phosphodiester bond of nucleic acids.

At least one of the sequences of interest of the encapsidated non-viral RNAs comprises a part coding a nuclease, i.e. this RNA sequence may comprise solely an RNA sequence coding a nuclease or alternatively an RNA sequence coding a nuclease and one or more other RNA sequences, and these other RNA sequences may for example code at least one protein, identical or different, or a non-coding RNA sequence.

More particularly, the nuclease is selected from the group constituted by the nucleases associated with the CRISPR system, the nuclease of the TALEN system, the nuclease of the Zn Finger system and the *Natronobacterium gregoryi* Argonaute (NgAgo) nuclease.

The CRISPR/Cas9 genome engineering system has become a genetic engineering tool with great potential. It involves two types of components:
  CRISPRs (Clustered Regularly Interspaced Short Palindromic Repeats) characterized by series of short direct repetitions (of 21 to 37 base pairs), regularly spaced by so-called "spacer" sequences, generally single, from 20 to 40 base pairs;

one of the nucleases associated with the CRISPR system, preferably the Cas9 nuclease (CRISPR associated protein 9), i.e. a specialized enzyme for cutting DNA with two active cutting zones, one for each strand of the double helix. For example, S. pyogenes uses the tool Cas9 for detecting and dismantling foreign DNA, such as invasion of the DNA of bacteriophages or of a plasmid DNA. Cas9 carries out this detection by unwinding the foreign DNA and verifying complementarity with the long spacer region of about twenty base pairs of the guide RNA. If a DNA sequence is related to the guide RNA, Cas9 cuts the invasive DNA.

This system is used for quickly and easily modifying the genome of animal and plant cells. Owing to the specificity of the target of Cas9, which originates from the guide RNA and from the complementarity of the DNA and not from the modifications of the protein itself (like TALEN and the zinc finger nucleases), the Cas9 tool can target a new DNA very easily.

The TALEN genome engineering system uses an artificial nuclease generated by the fusion of a DNA binding domain, called TALE, with a domain having the capacity to cleave DNA, called TALENs. The simple relationship between the amino acid sequence and the DNA sequence recognized by the DNA binding domain makes it possible to synthesize personalized proteins. These systems may be designed for fixing to almost any specific sequence of target DNA by combining a recognition domain of the DNA target TALE with a DNA cleavage domain.

The TAL effectors (TALE) are proteins secreted naturally by the bacterium *Xanthomonas* comprising a DNA binding domain constituted by repetitions of 33 or 34 identical amino acids except for the very variable amino acids 12 and 13, which confers recognition of a specific nucleotide. This simple relationship between the amino acid sequence and the recognition of the DNA makes it possible to create specific DNA binding domains of a sequence by selecting an assembly of repeated segments containing the appropriate variable residues. These specific DNA binding domains of a sequence may be designed quickly for fixing to almost any desired DNA sequence.

The non-specific DNA cleavage domain of the endonuclease Fok1 may be used for constructing hybrid nucleases that have proved to be effective in tests on yeast, in plant cells and animal cells. The first studies on TALENs were carried out with the original domain of Fok1, or variants of Fok1 having greater specificity or effectiveness of DNA cleavage.

The Fok1 domains function in the form of a dimer, which requires two constructs with DNA binding domains directed against sites of the genome having head to tail orientations and correct spacing.

By combining a TALE domain with a DNA cleavage domain (which will cut the DNA strand), it is thus possible to create specific restriction enzymes for any DNA sequence.

The Zn Finger system uses zinc finger nuclease, and consists of a combination of two proteins, each comprising three specifically selected zinc fingers for DNA recognition and a catalytic domain of the endonuclease Fok I.

The nature of the amino acids that make up a zinc finger will lead to the recognition of a specific sequence of DNA of three nucleotides. Thus, by using two proteins each comprising three specific zinc fingers, recognition is carried out on a specific sequence of eighteen nucleotides and will endow the genome with recognition specificity.

The endonuclease used is the endonuclease domain of the enzyme Fok I and acts in the dimeric form.

The Fok1 domains function in the form of a dimer, which requires two constructs with DNA binding domains directed against sites of the genome having head to tail orientations and correct spacing.

Advantageously, two proteins each comprising three zinc finger structures recognizing sequences several nucleotides apart are used. The binding of the two zinc finger proteins on their respective sequences brings the two endonucleases associated with them closer together. This bringing closer together allows dimerization of the endonucleases and then cleavage of the DNA double strand.

Preferably, the nuclease is selected from the group constituted by the Cas9 nuclease, the TALEN nuclease and the Zn Finger nuclease.

For "nucleases associated with the CRISPR system", there may be mentioned as a non-limitative example the wild-type version of the Cas9 nuclease (Cas9 WT), mutated for one of its two active sites (Cas9N or Cas9 Nickase) or mutated for its two active sites (dCas9), as well as the Cpf1 nuclease.

The Cas9 (CRISPR associated protein 9) nuclease is a specialized enzyme for cutting DNA with two active cutting zones, one for each strand of the double helix. For example, S. pyogenes uses the Cas9 tool for detecting and dismantling foreign DNA, such as invasion of the DNA of bacteriophages or of a plasmid DNA.

The TALEN nuclease (transcription activator-like effector nuclease) is generated by the fusion of a DNA binding domain, called TALE, and an enzymatic domain having the capacity to cleave DNA, such as for example the catalytic domain of Fok1, or variants of Fok1.

By "variant of Fok1" is meant any protein domain making it possible to cut the DNA sequence 5'-GGATG(N)$_9$-3' (SEQ ID NO:7).

The nuclease of the Zn Finger system is an artificial enzyme formed by the fusion of a DNA binding domain, of the zinc finger type, and of a DNA cleavage catalytic domain, for example the catalytic domain of Fok1, or variants of Fok1.

According to a first type of retroviral particle according to the invention, the sequence of interest of at least two encapsidated non-viral RNAs may comprise a part coding a nuclease.

These particles are of particular interest for the TALEN and ZnFinger genome engineering systems the nucleases of which act in the dimeric form. Also preferably, the sequence of interest comprises a part coding the TALEN nuclease or the zinc finger nuclease, more preferably for the catalytic domain of Fok1, or variants of Fok1.

According to a second type of retroviral particle, the at least two encapsidated non-viral RNAs differ by their sequence of interest.

More particularly, in this second type:
the sequence of interest of at least one RNA comprises a part coding a nuclease and a part coding a DNA recognition system at 3', and
the sequence of interest of at least one RNA comprises a part coding a nuclease and a part coding a DNA recognition system at 5'.

The part coding a DNA recognition system of the sequence of interest corresponds advantageously to an RNA coding a protein capable of recognizing a specific sequence of DNA.

Advantageously, in a retroviral particle according to this second type, the sequences of interest comprise a part coding the catalytic domain of the FokI nuclease, or variants of the latter.

This catalytic domain of the FokI nuclease is advantageously used for constructing the TALEN recombinant nucleases and the zinc finger nuclease, for implementing the TALEN or ZnFinger genome engineering systems, respectively.

By way of example, the retroviral particle according to the invention may comprise two encapsidated non-viral RNAs with different sequences of interest:
- a first sequence of interest comprising a part coding the FokI nuclease and a part coding a TALE 3', and
- a second sequence of interest comprising a part coding the FokI nuclease and a part coding a TALE 5';

or the retroviral particle according to the invention may comprise two encapsidated non-viral RNAs with different sequences of interest:
- a first sequence of interest comprising a part coding the FokI nuclease and a part coding three zinc fingers for recognition of a DNA sequence at 3', and
- a second sequence of interest comprising a part coding the FokI nuclease and a part coding three zinc fingers for recognition of a DNA sequence at 5'.

According to a specific embodiment, in the retroviral particle according to the invention, the sequence of interest of at least one of the encapsidated non-viral RNAs codes a nuclease.

Advantageously, in this specific embodiment, the nuclease is Cas9.

More particularly, in the retroviral particle according to this specific embodiment, the at least two encapsidated non-viral RNAs differ by their sequence of interest and the sequence of interest of the other encapsidated non-viral RNAs corresponds to at least one recognition element of a guide RNA.

A guide RNA corresponds to an RNA sequence generally comprising two recognition elements:
- a non-coding RNA ranging from 3 to 40 bases, capable of hybridizing by base complementarity to a specific sequence of the DNA and
- a non-coding RNA called "transactivator" ("scaffold"), which allows the nuclease to be fixed on the DNA.

The RNA sequence allows specific targeting of a specific DNA cleavage site.

The sequence of interest may comprise one or more part(s) corresponding to one or more guide RNAs, identical or different.

Advantageously, the sequence of interest of the second encapsidated non-viral RNA corresponds to a guide RNA. The guide RNA includes both the DNA recognition part and the part allowing fixation of a nuclease.

Preferably, the guide RNA is an sgRNA. Even more preferably, the guide RNA is a chimeric sgRNA comprising two repetitions of the encapsidation sequence.

Preferably, the particle comprises two RNAs with different sequences of interest:
- a first sequence of interest coding the Cas9 nuclease, and
- a second sequence of interest corresponding to a guide RNA.

Advantageously, the retroviral particle according to this specific embodiment further comprises at least one third encapsidated non-viral RNA having a sequence of interest corresponding to a second recognition element of a guide RNA or to an additional guide RNA.

Advantageously, the particle comprises three RNAs with different sequences of interest:
- a first sequence of interest coding the Cas9 nuclease,
- a second sequence of interest corresponding to a guide RNA, and
- a third sequence of interest corresponding to a guide RNA identical to or different from the second sequence of interest.

Advantageously, the retroviral particle according to the invention comprises a nucleocapsid protein, an envelope protein, optionally an integrase and at least two encapsidated non-viral RNAs, the encapsidated non-viral RNAs each comprising an RNA sequence of interest bound to an encapsidation sequence, each encapsidation sequence being recognized by a binding domain introduced into the nucleocapsid protein and/or into the integrase.

By "nucleocapsid protein" is meant the protein of structure NC encoded by the gag gene. When the binding domain is introduced into the nucleocapsid protein, this protein is a chimeric protein, derived from a chimeric gag gene.

When the binding domain is introduced into the integrase, the integrase is a chimeric protein, derived from a chimeric pol gene.

By "chimeric protein" is meant a recombinant protein comprising several different fused protein sequences.

According to a first embodiment, in the retroviral particle according to the invention, the binding domain is introduced into the nucleocapsid protein and the at least two encapsidated non-viral RNAs differ by their RNA sequence.

This first embodiment allows early, transient expression of the RNA of interest, without an associated integration event in the genome of the target cells.

In fact, on bringing a particle according to this first embodiment into contact with a target cell, the membrane of the retroviral particle and that of the target cell will fuse and allow the contents of the particle to be released in the target cell. The RNAs are then released in the cytoplasm and the cellular machinery allows these RNAs to be translated directly into protein(s), i.e. without additional steps such as reverse transcription, translocation into the nucleus or integration in the genome of the target cell.

More particularly, the at least two non-viral RNAs have the same encapsidation sequence. In this case, the at least two encapsidated non-viral RNAs differ by their RNA sequence of interest, i.e. the RNA sequences of interest contained in the two encapsidated non-viral RNAs are different. By "different" is meant sequences of interest that are not identical or have a difference not resulting from a spontaneous mutation or not intentionally selected by the manipulator.

Alternatively, the at least two non-viral RNAs have two different encapsidation sequences. These at least two encapsidation sequences are then recognized by at least two different binding domains, at least one of these domains being introduced into the nucleocapsid protein. In this case, the at least two encapsidated non-viral RNAs may comprise identical or different sequences of interest.

It is possible to encapsidate at least two non-viral RNAs, preferably three non-viral RNAs.

According to a particular embodiment of the first embodiment, a second binding domain is introduced into the nucleocapsid protein of the retroviral particle according to the invention.

By way of example, the second binding domain may be the "Coat" protein of the MS2 bacteriophage when the first binding domain is the "Coat" protein of the PP7 phage or the second binding domain may be the "Coat" protein of the PP7 phage when the first binding domain is the "Coat" protein of the MS2 bacteriophage.

In this case, at least two encapsidated non-viral RNAs bear different encapsidation sequences, each encapsidation sequence corresponding respectively to the first and second binding domain introduced into the nucleocapsid protein.

More particularly, when three non-viral RNAs are encapsidated:
- at least two of the encapsidated non-viral RNAs have the same encapsidation sequence corresponding to the first binding domain and differ only by their RNA sequence of interest,
- the third encapsidated non-viral RNA may bear an identical or different encapsidation sequence. When the encapsidation sequence is different, the latter may correspond to a second binding domain introduced into the nucleocapsid protein.

Other binding domains may also be introduced into the nucleocapsid protein.

Besides the binding domain or domains introduced into the nucleocapsid protein, it is also possible to introduce a binding domain into the integrase.

The integrase is then a chimeric protein, derived from a chimeric pol gene.

Preferably, when the binding domain is introduced into the integrase, the sequence of the integrase is mutated at the level of the C-terminal domain in order to insert the sequence of the binding domain. Even more preferably, the sequence of the integrase is mutated at the level of the C-terminal domain so as to introduce that of the "Coat" protein of the MS2 bacteriophage or PP7 phage.

In this case, the at least two encapsidated non-viral RNAs may bear different encapsidation sequences, each encapsidation sequence corresponding to the binding domains introduced into the nucleocapsid protein and into the integrase, respectively.

More particularly, when three non-viral RNAs are encapsidated:
- at least two of the encapsidated non-viral RNAs have the same encapsidation sequence corresponding to the first binding domain and differ only by their RNA sequence of interest,
- the third encapsidated non-viral RNA bearing a different encapsidation sequence, corresponding to a second binding domain introduced into the integrase.

Other binding domains may also be introduced into the integrase.

Advantageously, the retroviral particle according to the invention is a lentiviral particle.

Preferably, in such a lentiviral particle:
the binding domain is the "Coat" protein of the MS2 bacteriophage,
the encapsidation sequence of the non-viral RNA is a stem-loop sequence of MS2,
the nucleocapsid protein is the nucleocapsid (NC) protein of HIV belonging to the Gag polyprotein, chimeric, the NC sequence being mutated at the level of the second zinc finger in order to insert the sequence of the "Coat" protein of the MS2 bacteriophage.
Advantageously:
The envelope protein is the VSV-G protein coding the envelope protein of the Vesicular stomatitis virus.
The encapsidation sequence comprises from 2 to 25 repetitions of the stem-loop sequence of MS2, preferably from 6 to 18 repetitions of the stem-loop sequence, even more preferably from 10 to 14, for example 12 repetitions. Preferably, the stem-loop sequence is as follows: ctagaaaacatgaggatcacccatgtctgcag (SEQ ID No.1).

Or, preferably, in such a lentiviral particle:
the binding domain is the "Coat" protein of the PP7 phage,
the encapsidation sequence of the non-viral RNA is a stem-loop sequence of PP7,
the nucleocapsid protein is the nucleocapsid (NC) protein of HIV belonging to the Gag polyprotein, chimeric, the NC sequence being mutated at the level of the second zinc finger in order to insert the sequence of the "Coat" protein of the PP7 phage.
Advantageously:
The envelope protein is the VSV-G protein coding the envelope protein of the Vesicular stomatitis virus.
The encapsidation sequence comprises from 2 to 25 repetitions of the stem-loop sequence of PP7, preferably from 2 to 18 repetitions of the stem-loop sequence, even more preferably from 2 to 12, for example 6 repetitions. Preferably, the stem-loop sequence is as follows: ctagaaaggagcagacgatatggcgtcgctccctgcag (SEQ ID No.2).

Advantageously, SEQ ID No.2 may be optimized to promote the folding of the stem-loop. In particular, it was found that it could be advantageous to insert SEQ ID No.2 and SEQ ID No.4 successively. This alternation of SEQ ID No.2 and SEQ ID No.4 (ctagaaaccagcagag-catatgggctcgctggctgcag) to promote folding is particularly advantageous in the case of a coding RNA. On the other hand, for a non-coding RNA, each stem-loop motif of PP7 is advantageously obtained by successively inserting the stem-loop sequence SEQ ID No.5 (ggagcagacga-tatggcgtcgctcc) and the stem-loop sequence SEQ ID No.6 (ccagcagagcatatgggctcgctgg).

Optionally, the second binding domain introduced into the integrase may be the Coat protein of the PP7 phage if the first binding domain is the Coat protein of the MS2 bacteriophage, or the second binding domain introduced into the integrase may be the Coat protein of the MS2 bacteriophage if the first binding domain is the Coat protein of the PP7 phage.

According to a second embodiment, the invention relates to a retroviral particle comprising a protein derived from the Gag polyprotein, preferably a nucleocapsid protein, an envelope protein, an integrase and at least two encapsidated non-viral RNAs, the encapsidated non-viral RNAs each comprising an RNA sequence of interest bound to an encapsidation sequence, each encapsidation sequence being recognized by a binding domain introduced into the integrase, and optionally by a binding domain introduced into a protein derived from the Gag polyprotein, preferably a nucleocapsid protein.

This second embodiment allows transient expression of the RNA of interest, without an associated integration event in the genome of the target cells.

Preferably, in this second embodiment, the sequence of the integrase is mutated at the level of the C-terminal domain in order to insert the sequence of the binding domain.

Advantageously, the binding domain is a heterologous domain. More particularly, the binding domain is the Coat protein of the MS2 bacteriophage, PP7 phage or Qβ phage, the prophage HK022 Nun protein, the U1A protein or the hPum protein.

Preferably, the sequence of the integrase is mutated at the level of the C-terminal domain so as to introduce that of the "Coat" protein of the MS2 bacteriophage or PP7 phage.

The at least two non-viral RNAs may or may not have the same encapsidation sequence.

Similarly, the at least two encapsidated non-viral RNAs may or may not have the same RNA sequence of interest.

Preferably, the at least two encapsidated non-viral RNAs differ by their RNA sequence of interest, i.e. the RNA sequences of interest contained in the two encapsidated non-viral RNAs are different.

More particularly, the at least two non-viral RNAs have the same encapsidation sequence, the latter being recognized by the binding domain introduced into the integrase.

It is possible to encapsidate at least two non-viral RNAs, preferably three non-viral RNAs.

According to a particular embodiment of the second embodiment, a second binding domain is introduced into the integrase of the retroviral particle according to the invention.

As an example, the second binding domain may be the "Coat" protein of the MS2 bacteriophage when the first binding domain is the "Coat" protein of the PP7 phage or the second binding domain may be the "Coat" protein of the PP7 phage when the first binding domain is the "Coat" protein of the MS2 bacteriophage.

In this case, at least two encapsidated non-viral RNAs bear different encapsidation sequences, each encapsidation sequence corresponding respectively to the first and second binding domain introduced into the integrase.

More particularly, when three non-viral RNAs are encapsidated:
  at least two of the encapsidated non-viral RNAs have the same encapsidation sequence corresponding to the first binding domain, and these two non-viral RNAs may optionally differ by their RNA sequence of interest,
  the third encapsidated non-viral RNA may bear an identical or different encapsidation sequence. When the encapsidation sequence is different, the latter may correspond to a second binding domain introduced into the integrase.

Other binding domains may also be introduced into the integrase.

Besides the binding domain or domains introduced into the integrase, it is also possible to introduce a binding domain into the nucleocapsid protein.

The nucleocapsid protein is then a chimeric protein, derived from a chimeric gag gene.

In this case, the at least two encapsidated non-viral RNAs may bear different encapsidation sequences, each encapsidation sequence corresponding to the binding domains introduced into the integrase and into the nucleocapsid protein, respectively.

More particularly, when three non-viral RNAs are encapsidated:
  at least two of the encapsidated non-viral RNAs have the same encapsidation sequence corresponding to the first binding domain introduced into the integrase, and these non-viral RNAs may optionally differ by their RNA sequence of interest,
  the third encapsidated non-viral RNA bears a different encapsidation sequence, corresponding to a second binding domain introduced into the nucleocapsid protein.

Other binding domains may also be introduced into the nucleocapsid protein.

Advantageously, in the case when the particle according to the invention comprises a nucleocapsid protein, the binding domain may be introduced into the nucleocapsid protein, and a second binding domain may be introduced into the nucleocapsid and/or into the integrase.

Preferably, the retroviral particle according to the invention then comprises a nucleocapsid protein, an envelope protein, optionally an integrase and at least two encapsidated non-viral RNAs, the encapsidated non-viral RNAs each comprising an RNA sequence of interest bound to an encapsidation sequence, at least one encapsidation sequence being the stem-loop motif (or stem-loop sequence) of the MS2 bacteriophage repeated 12 times, this motif being recognized by the Coat protein of the MS2 bacteriophage introduced into the nucleocapsid protein.

The stem-loop motif is advantageously the sequence SEQ ID No.1.

By way of example, such a particle according to the invention is the particle MS2 (NC)-RLP 12X, described below in the Examples.

In this retroviral particle, the encapsidated non-viral RNA comprising as encapsidation sequence the stem-loop motif of the MS2 bacteriophage repeated 12 times is advantageously an RNA coding Cas9, and a second encapsidated non-viral RNA is an RNA corresponding to at least one recognition element of a guide RNA or coding a guide, said encapsidated non-viral RNA comprising, as encapsidation sequence, the stem-loop motif of the MS2 bacteriophage repeated 2 times.

By way of example, such a particle according to the invention is the particle MS2 (NC)-RLP 12X 2X, described below in the Examples.

Alternatively or concomitantly, the retroviral particle according to the invention comprises a nucleocapsid protein, an envelope protein, optionally an integrase and at least two encapsidated non-viral RNAs, the encapsidated non-viral RNAs each comprising an RNA sequence of interest bound to an encapsidation sequence, at least one encapsidation sequence being the stem-loop motif of the PP7 bacteriophage repeated 2 times, this motif being recognized by the Coat protein of the PP7 bacteriophage introduced into the nucleocapsid protein.

Advantageously, the stem-loop motif is the sequence SEQ ID No.2. Alternatively, the stem-loop motif is an alternation of SEQ ID No.2 and SEQ ID No.4, in particular for a coding RNA, or SEQ ID No.5 and SEQ ID No.6, in particular for a non-coding RNA.

By way of example, when the particle according to the invention comprises, as encapsidation sequence, only the stem-loop motif of the PP7 bacteriophage repeated 2 times, such a particle according to the invention is the particle PP7 (NC)-RLP 2X, described below in the Examples.

By way of example, when the particle according to the invention comprises concomitantly, as encapsidation sequences, the stem-loop motif of the MS2 bacteriophage repeated 12 times and the stem-loop motif of the PP7 bacteriophage repeated 2 times, such a particle according to the invention is the particle MS2/PP7 (NC)-RLP 12X 2X, described below in the Examples.

Alternatively, in the retroviral particle according to the invention, the binding domain may be introduced into the integrase, and a second binding domain may be introduced into the nucleocapsid and/or into the integrase.

Advantageously, the retroviral particle according to the invention is a lentiviral particle.

When the retroviral particle is a lentiviral particle, it is possible to express RNAs of interest transiently, without an associated integration event in the genome of the target cells, in particular of the quiescent cells.

In fact, besides its role in the integration reaction itself, the integrase (IN) participates in various steps of the replication cycle of the retroviruses such as morphogenesis of the viral particle, reverse transcription and nuclear import of the pre-integration complex (PIC).

More particularly, in lentiviruses, the integrase contains nuclear localization sequences (NLS) allowing its localization in the nucleus thanks to the PIC. Consequently, when encapsidation of non-viral RNAs is carried out by a binding domain carried by an integrase of a lentivirus, the encapsidated non-viral RNAs will be transported into the nucleus of the target cell. In fact, on bringing a lentiviral particle according to this second embodiment into contact with a target cell, the membrane of the particle and that of the target cell will fuse and allow release of the contents of the capsid in the target cell. The integrase then takes charge of the RNAs and, via the PICs, will allow import of the RNAs into the nucleus. This taking charge is particularly advantageous for certain applications, such as expression in quiescent cells. In the case of retroviral particles, other than the lentiviruses, the integrase does not contain these NLSs and is therefore localized in the cytoplasm. It is, however, possible to add the NLS sequences to this type of integrase, in order to induce nuclear localization of the integrase, and therefore of the RNAs taken in charge by this integrase.

This taking in charge is also particularly useful for a CRISPR system, which employs guide RNAs that will hybridize specifically to the genome of the target cell. Once hybridized, these guide RNAs guide an endonuclease (Cas9), which will allow modification of a specific locus of the genome of the target cell. More particularly, in such a lentiviral particle:
- the binding domain is the "Coat" protein of the MS2 bacteriophage,
- the encapsidation sequence of the non-viral RNAs is a stem-loop sequence of MS2,
- the integrase is a chimeric enzymatic protein the sequence of which is mutated at the level of the C-terminal domain in order to insert the sequence of the "Coat" protein of the MS2 bacteriophage.

Now, more particularly, in such a lentiviral particle:
- the binding domain is the "Coat" protein of the PP7 phage,
- the encapsidation sequence of the non-viral RNAs is a stem-loop sequence of PP7,
- the integrase is a chimeric enzymatic protein the sequence of which is mutated at the level of the C-terminal domain in order to insert the sequence of the "Coat" protein of the PP7 phage.

Optionally, the second binding domain introduced into the nucleocapsid may be the Coat protein of the PP7 phage if the first binding domain is the Coat protein of the MS2 bacteriophage or the second binding domain introduced into the integrase may be the Coat protein of the MS2 bacteriophage if the first binding domain is the Coat protein of the PP7 phage.

In fact, the integrase (IN) is made up of 3 separate functional domains, each indispensable for ensuring a complete integration reaction. The N-terminal domain contains a motif of the zinc finger type that stabilizes the folded structure of the IN and increases the catalytic activity of the enzyme. The central domain of the IN contains the amino acid motif DDE, to which the catalytic activity of the enzyme is attributed. This central domain is also involved in recognition of the nucleotide sequence conserved at each end of the retroviral DNA. The C-terminal domain is the least conserved among the family of the retroviruses. It has DNA binding activity and is indispensable for the reactions of maturation of the 3' ends of strand transfer. Besides its role in the integration reaction itself, IN participates in various steps of the replication cycle of the retroviruses such as morphogenesis of the viral particle, reverse transcription and nuclear import of the pre-integration complex.

As described by Petit et al. (1999; J. Virol. P5079-5088), insertion of an exogenous sequence at C-terminal of IN does not disturb the steps of production and transduction of target cells whereas the same insertion at N-terminal does not allow detection of a transduction event.

The retroviral particle was therefore modified to contain the "Coat" protein of the MS2 bacteriophage fused with the protein of the integrase (see FIG. 1) or the "Coat" protein of the PP7 phage (see FIG. 37). The p8.74 encapsidation plasmid, bearing the pol gene coding the protein of integrase, is modified in order to insert the sequence coding the Coat protein at C-terminal of the integrase by assembly PCR. The p8.74 plasmid is linearized by PCR and then the Coat sequence, previously amplified by PCR, is cloned at the C-terminal level of the integrase, either directly end-to-end or with the addition of a linker.

Advantageously:
- The envelope protein is the VSV-G protein coding the envelope protein of the Vesicular stomatitis virus.
- The encapsidation sequence comprises from 2 to 25 repetitions of the stem-loop sequence of MS2 and/or of PP7, depending on the binding domain introduced, preferably from 2 to 18 repetitions, more preferably from 2 to 18 repetitions, such as from 6 to 18 repetitions of the stem-loop sequence, even more preferably for the stem-loop sequence of MS2, from 10 to 14, for example 12 repetitions.
- Preferably, the stem-loop sequence is as follows: ctagaaaacatgaggatcacccatgtctgcag (SEQ ID No.1) when the binding domain is the Coat protein of MS2 and/or the stem-loop sequence is as follows: ctagaaaggagcagacgatatggcgtcgctccctgcag (SEQ ID No.2) when the binding domain is the Coat protein of PP7.

Several examples of lentiviral particle according to the invention are described below and in more detail for some of them in the examples that follow:
- an MS2RLP or MS2 (NC)-RLP 12X particle is a lentiviral particle formed by encapsidation of RNAs bearing the stem-loop motif of the MS2 bacteriophage, repeated 12 times, by inserting the Coat protein of the MS2 bacteriophage into the nucleocapsid,
- an MS2 (NC)-RLP 2X particle is a lentiviral particle formed by encapsidation of RNAs bearing the stem-loop motif of the MS2 bacteriophage, repeated 2 times, by inserting the Coat protein of the MS2 bacteriophage into the nucleocapsid,
- an MS2RLP 12X 2X or MS2 (NC)-RLP 12X 2X particle is a lentiviral particle formed by encapsidation of at least one first RNA bearing the stem-loop motif of the MS2 bacteriophage, repeated 12 times and of at least one second RNA bearing the stem-loop motif of the MS2 bacteriophage, repeated 2 times, by inserting the Coat protein of the MS2 bacteriophage into the nucleocapsid,
- an MS2 (NC)-RLP 6X particle is a lentiviral particle formed by encapsidation of RNAs bearing the stem-loop motif of the MS2 bacteriophage, repeated 6 times, by inserting the Coat protein of the MS2 bacteriophage into the nucleocapsid,
- an MS2 (IN)-RLP 2X particle is a lentiviral particle formed by encapsidation of RNAs bearing the stem-loop motif of the MS2 bacteriophage, repeated 2 times, by inserting the Coat protein of the MS2 bacteriophage into the integrase,
- an MS2 (IN)-RLP 6X particle is a lentiviral particle formed by encapsidation of RNAs bearing the stem-loop motif of the MS2 bacteriophage, repeated 6 times, by inserting the Coat protein of the MS2 bacteriophage into the integrase, an MS2 (IN)-RLP 12X particle is a lentiviral particle formed by encapsidation of RNAs bearing the stem-loop motif of the MS2 bacteriophage, repeated 12 times, by inserting the Coat protein of the MS2 bacteriophage into the integrase, a PP7RLP or PP7 (NC)-RLP 2X particle is a lentiviral particle formed by encapsidation of RNAs bearing the stem-loop motif of the PP7 phage, repeated 2 times, by inserting the Coat protein of the PP7 phage into the nucleocapsid, a PP7 (NC)-RLP 6X particle is a lentiviral particle formed by encapsidation of RNAs bearing the stem-loop motif of the PP7 phage, repeated 6 times, by inserting the Coat protein of the PP7 phage into the nucleocapsid, a PP7RLP or PP7 (NC)-RLP 12X particle is a lentiviral particle formed by encapsidation of RNAs bearing the stem-loop motif of the PP7 phage, repeated 12 times, by inserting the Coat protein of the PP7 phage into the nucleocapsid, a PP7 (IN)-RLP 2X particle is a lentiviral particle formed by encapsidation of RNAs bearing the stem-loop motif of the PP7 phage, repeated 2 times, by inserting the Coat protein of the PP7 phage into the integrase, a PP7 (IN)-RLP 6X particle is a lentiviral particle formed by encapsidation of RNAs bearing the stem-loop motif of the PP7 phage, repeated 6 times, by inserting the Coat protein of the PP7 phage into the integrase, a PP7 (IN)-RLP 12X particle is a lentiviral particle formed by encapsidation of RNAs bearing the stem-loop motif of the PP7 phage, repeated 12 times, by inserting the Coat protein of the PP7 phage into the integrase.

an MS2/PP7RLP or MS2/PP7(NC)-RLP 12X 2X particle is a lentiviral particle formed by encapsidation of RNAs bearing the stem-loop motif of the MS2 bacteriophage, repeated 12 times, by inserting the Coat protein of the MS2 bacteriophage into the nucleocapsid, and bearing the stem-loop motif of the PP7 phage, repeated 2 times, by inserting the Coat protein of the PP7 phage into the nucleocapsid.

Preferably, the lentiviral particle formed by encapsidation of RNAs bears a stem-loop motif of the MS2 bacteriophage or PP7 phage, repeated from 2 to 25 times, more preferably 2, 6 or 12 times.

Even more preferably, the particle according to the invention is selected from MS2 (NC)-RLP 12X, MS2 (NC)-RLP 12X 2X, PP7 (NC)-RLP 6X, PP7 (NC)-RLP 2X, MS2 (IN)-RLP 12X, PP7 (IN)-RLP 6X and PP7 (IN)-RLP 2X, MS2/PP7 (NC)-RLP 12X 2X.

The invention also relates to compositions comprising particles according to the invention.

More particularly, the compositions according to the invention are concentrated compositions. Advantageously, the compositions are also purified. These compositions may be concentrated and purified by the method described in application WO2013/014537.

Typically, the compositions according to the invention comprise less than 30% of DNA contaminants and less than 45% of protein contaminants with respect to the crude supernatant. More particularly, the compositions according to the invention comprise less than 30% of DNA contaminants and less than 2% of protein contaminants with respect to the crude supernatant.

By "crude supernatant" is meant the supernatant of cell culture(s), comprising retroviral particles according to the invention, after clarification. Such a clarification step is more particularly described below in the methods for producing the particles according to the invention. When recovery of the supernatant is carried out several times, the crude supernatant then corresponds to all of the supernatants collected, combined (or "pooled") and then clarified.

Optionally, the compositions according to the invention comprise less than 1% of DNA contaminants and less than 1% of protein contaminants with respect to the crude supernatant.

The invention also relates to kits for producing particles according to the invention and to the manufacturing methods for these kits.

More particularly, the invention relates to a kit for producing particles according to the invention, comprising:
(i) an expression plasmid comprising at least one sequence of interest, for which an encapsidation sequence is inserted upstream of, downstream of or within this sequence,
(ii) an encapsidation plasmid coding a protein derived from the Gag polyprotein and/or a chimeric integrase, comprising a binding domain allowing recognition of an encapsidation sequence, and,
(iii) an envelope plasmid coding an envelope protein.

Such a kit may also comprise instructions for use of the plasmids contained in the kit.

More specifically, when the kit is for producing particles according to the first embodiment, this kit comprises:
(i) an expression plasmid comprising at least two different non-viral RNA sequences, each RNA sequence comprising a sequence of interest for which an encapsidation sequence is inserted upstream of, downstream of or within this sequence of interest, or alternatively a first and a second expression plasmid each comprising a sequence of interest, upstream or downstream of which an encapsidation sequence is inserted,
(ii) an encapsidation plasmid coding a chimeric nucleocapsid protein comprising a binding domain allowing recognition of the encapsidation sequence, and,
(iii) an envelope plasmid coding an envelope protein.

The at least two non-viral RNA sequences are different because the sequences of interest are different and/or the encapsidation sequences are different.

As a plasmid is a DNA structure, it is well known that by "expression plasmid comprising at least two non-viral RNA sequences" is meant an expression plasmid coding at least two non-viral RNA sequences.

In fact, the expression plasmids of the kits contain all the DNA sequences necessary for obtaining at least one non-viral RNA by transcription. The expression plasmid contains at least one promoter, followed by a DNA sequence of interest (cDNA or DNA that will be transcribed into a non-viral RNA) and an encapsidation sequence (a DNA coding example for MS2 or PP7 repeat motifs) and optionally an RNA stabilizing sequence.

Preferably, the kit for producing the particles according to the first embodiment comprises:
(i) an expression plasmid comprising at least two sequences of interest, for which an encapsidation sequence is inserted upstream of, downstream of or within each of these sequences, or alternatively a first and a second expression plasmid each comprising a sequence of interest, upstream or downstream of which an encapsidation sequence is inserted, the sequences of interest being different and the encapsidation sequences being identical,
(ii) an encapsidation plasmid coding a chimeric nucleocapsid protein comprising a binding domain allowing recognition of the encapsidation sequence, and,
(iii) an envelope plasmid coding an envelope protein.

Advantageously, the kit produces lentiviral particles.

Preferably:

In the expression plasmid, the encapsidation sequence comprises from 2 to 25 repetitions of the stem-loop sequence of MS2, preferably from 6 to 18 repetitions of the stem-loop sequence, even more preferably from 10 to 14, for example 12 repetitions. Advantageously, the stem-loop sequence is as follows: ctagaaaacatgaggatcacccatgtctgcag (SEQ ID No.1).

In the encapsidation plasmid, the nucleocapsid protein is the nucleocapsid (NC) protein of HIV belonging to the Gag polyprotein, said NC is mutated at the level of the second zinc finger in order to insert the sequence of the "Coat" protein of the MS2 bacteriophage.

In the envelope plasmid, the envelope protein is the VSV-G protein coding the envelope protein of the Vesicular stomatitis virus.

Or, preferably:

In the expression plasmid, the encapsidation sequence comprises from 2 to 25 repetitions of the stem-loop sequence of PP7, preferably from 2 to 18 repetitions of the stem-loop sequence, even more preferably from 2 to 12, for example 6 repetitions. Advantageously, the stem-loop sequence is as follows: ctagaaaggagcagacgatatggcgtcgctccctgcag (SEQ ID No.2). Alternatively, the stem-loop sequence is an alternation of SEQ ID No.2 and SEQ ID No.4, in particular for a coding RNA, or SEQ ID No.5 and SEQ ID No.6, in particular for a non-coding RNA.

In the encapsidation plasmid, the nucleocapsid protein is the nucleocapsid (NC) protein of HIV belonging to the Gag polyprotein, said NC is mutated at the level of the second zinc finger in order to insert the sequence of the "Coat" protein of the PP7 phage.

In the envelope plasmid, the envelope protein is the VSV-G protein coding the envelope protein of the Vesicular stomatitis virus.

Optionally, the kit comprises a second encapsidation plasmid coding a chimeric integrase comprising a binding domain allowing recognition of an encapsidation sequence. The second binding domain may be identical to or different from the binding domain of the chimeric nucleocapsid protein.

By way of examples of various binding domains:
the binding domain introduced into the nucleocapsid may be the Coat protein of MS2 and the binding domain introduced into the integrase may be the Coat protein of PP7, or
the binding domain introduced into the nucleocapsid may be the Coat protein of PP7 and the binding domain introduced into the integrase may be the Coat protein of MS2.

Several binding domains may be introduced into each of the chimeric proteins.

Alternatively, when the kit is for producing particles according to the second embodiment, this kit comprises:
(i) an expression plasmid comprising at least one sequence of interest, for which an encapsidation sequence is inserted upstream of, downstream of or within this sequence,
(ii) an encapsidation plasmid coding a chimeric integrase comprising a binding domain allowing recognition of the encapsidation sequence, and,
(iii) an envelope plasmid coding an envelope protein.

Advantageously, the promoters employed in the expression plasmids of the kits according to the invention are EF1, in particular when the sequence of interest is a nuclease, such as Cas9, and U6, in particular when the sequence of interest is at least one recognition element of a guide RNA or is a guide RNA.

Advantageously, the production kits according to the invention may further comprise a second encapsidation plasmid coding:
a protein derived from the wild-type Gag polyprotein, when the first encapsidation plasmid codes a protein derived from the chimeric Gag polyprotein, and/or
a wild-type integrase, when the first encapsidation plasmid codes a chimeric integrase.

Manufacturing methods for the kits according to the invention are also proposed. Typically, a method for manufacturing a kit according to the invention comprises:
(i) preparing an expression plasmid comprising at least one sequence of interest, for which an encapsidation sequence is inserted upstream of, downstream of or within this sequence
(ii) preparing an encapsidation plasmid coding a protein derived from the Gag polyprotein and/or a chimeric integrase, comprising a binding domain allowing recognition of an encapsidation sequence, and
(iii) preparing an envelope plasmid coding an envelope protein.

More specifically, when the method relates to a kit for producing the particles according to the first embodiment, it comprises:
(i) preparing an expression plasmid comprising at least two different non-viral RNA sequences, each RNA sequence comprising a sequence of interest for which an encapsidation sequence is inserted upstream of, downstream of or within this sequence of interest, or alternatively a first and a second expression plasmid each comprising a sequence of interest, upstream or downstream of which an encapsidation sequence is inserted,
(ii) preparing an encapsidation plasmid coding a chimeric nucleocapsid protein comprising a binding domain allowing recognition of the encapsidation sequence, and,
(iii) preparing an envelope plasmid coding an envelope protein.

The at least two non-viral RNA sequences are different because the sequences of interest are different and/or the encapsidation sequences are different.

Preferably, this method comprises:
(i) preparing an expression plasmid comprising at least two sequences of interest, for which an encapsidation sequence is inserted upstream of, downstream of or within each of these sequences, or alternatively a first and a second expression plasmid each comprising a sequence of interest, upstream or downstream of which an encapsidation sequence is inserted,
the sequences of interest being different and the encapsidation sequences being identical,
(ii) preparing an encapsidation plasmid coding a chimeric nucleocapsid protein comprising a binding domain allowing recognition of the encapsidation sequence, and (iii) preparing an envelope plasmid coding an envelope protein.

Alternatively, when the method relates to a kit for producing the particles according to the second embodiment, this method comprises:
  (i) preparing an expression plasmid comprising at least one sequence of interest, for which an encapsidation sequence is inserted upstream of, downstream of or within this sequence,
  (ii) preparing an encapsidation plasmid coding a chimeric integrase comprising a binding domain allowing recognition of the encapsidation sequence, and,
  (iii) preparing an envelope plasmid coding an envelope protein.

The invention also relates to manufacturing methods for particles according to the invention.

Such a method comprises a step of co-transfection of cells with:
  (i) an expression plasmid comprising at least one sequence of interest, for which an encapsidation sequence is inserted upstream of, downstream of or within this sequence,
  (ii) an encapsidation plasmid coding a protein derived from the Gag polyprotein and/or a chimeric integrase comprising a binding domain allowing recognition of an encapsidation sequence, and,
  (iii) an envelope plasmid coding an envelope protein.
  and recovery of the supernatant of the transfected cells comprising the particles.

The cells utilized in the manufacturing methods for particles according to the invention are producer cells, i.e. cells which, once transfected with the plasmids bearing the genetic material necessary for formation of the retroviral particles, allow formation of said particles. By way of example of producer cells, HEK293T may be mentioned.

By "step of co-transfection" is meant a step of transfection during which transfection is carried out by bringing the producer cells into contact with all of the plasmids of the method for manufacturing the particles.

More specifically, when the aim of the manufacturing method is to produce particles according to the first embodiment, it comprises a step of co-transfection of cells with:
  (i) an expression plasmid comprising at least two different non-viral RNA sequences, each RNA sequence comprising a sequence of interest for which an encapsidation sequence is inserted upstream of, downstream of or within this sequence of interest, or alternatively a first and a second expression plasmid each comprising a sequence of interest, upstream or downstream of which an encapsidation sequence is inserted,
  (ii) an encapsidation plasmid coding a chimeric nucleocapsid protein comprising a binding domain allowing recognition of the encapsidation sequence, and,
  (iii) an envelope plasmid coding an envelope protein, and recovery of the supernatant of the transfected cells comprising the particles.

The at least two non-viral RNA sequences are different because the sequences of interest are different and/or the encapsidation sequences are different.

Preferably, this method for manufacturing particles comprises a step of co-transfection of cells with:
  (i) an expression plasmid comprising at least two sequences of interest, for which an encapsidation sequence is inserted upstream of, downstream of or within each of these sequences, or alternatively a first and a second expression plasmid each comprising a sequence of interest, upstream or downstream of which an encapsidation sequence is inserted,
  the sequences of interest being different and the encapsidation sequences being identical,
  (ii) an encapsidation plasmid coding a chimeric nucleocapsid protein comprising a binding domain allowing recognition of the encapsidation sequence, and,
  (iii) an envelope plasmid coding an envelope protein, and recovery of the supernatant of the transfected cells comprising the particles.

Alternatively, when the aim of the manufacturing method is to produce particles according to the second embodiment, this method comprises a step of co-transfection of cells with:
  (i) an expression plasmid comprising at least one sequence of interest, for which an encapsidation sequence is inserted upstream of, downstream of or within this sequence,
  (ii) an encapsidation plasmid coding a chimeric integrase comprising a binding domain allowing recognition of the encapsidation sequence, and,
  (iii) an envelope plasmid coding an envelope protein,
  and recovery of the supernatant of the transfected cells comprising the particles.

Advantageously, in the manufacturing method according to the invention, the expression plasmids represent at least 50% by number of the total plasmids utilized in the co-transfection.

In the manufacturing method according to the invention, the step of co-transfection may in addition be carried out with a second encapsidation plasmid coding:
  a protein derived from the wild-type Gag polyprotein, when the first encapsidation plasmid codes a protein derived from the chimeric Gag polyprotein, and/or
  a wild-type integrase, when the first encapsidation plasmid codes a chimeric integrase.

Advantageously, the ratio of the second encapsidation plasmid to the first encapsidation plasmid is in the range from [10:90] to [60:40], preferably in the range from [20:80] to [50:50].

The advantages associated with the use of a second encapsidation plasmid and more particularly with the ratios defined above are described more fully in Example 13.

Preferably, all the manufacturing methods for the particles according to the invention are carried out by the methods described in application WO2013/014537.

More particularly, these manufacturing methods for the particles are carried out on producer cells cultured in a medium without serum, and no induction with sodium butyrate is carried out.

Advantageously, the supernatant is collected several times, for example between 3 and 6 times, at specific time intervals, such as at time intervals of the order of the half-life of the retroviral particles. Typically, recovery of the supernatant is carried out 4 to 5 times, at time intervals of the order of 6 to 18 h, preferably from 8 to 16 h, such as 8 h, 12 h and/or 16 h. Preferably, said collection is carried out after changing the culture medium of the cells, this changing preferably being carried out at 24 h post-transfection.

The manufacturing methods for the particles according to the invention also comprise a step in which the supernatant is clarified.

Preferably, the supernatant is clarified by centrifugation.

Even more preferably, these manufacturing methods for the particles according to the invention further comprise a step in which the supernatant is concentrated and/or purified.

Preferably, concentration and purification are carried out by frontal ultrafiltration on centrifugation units.

Advantageously, the supernatant undergoes one or more additional purification steps. These purification steps are preferably carried out by tangential ultrafiltration and/or diafiltration. Even more preferably, the supernatant undergoes a step of tangential ultrafiltration followed by a step of diafiltration.

Tangential ultrafiltration is advantageously carried out on polysulphone hollow-fibre cartridges.

Optionally, the composition may then undergo a step of ion exchange chromatography, in particular anion exchange chromatography. The eluate from this chromatography step is recovered and then concentrated again by frontal ultrafiltration on central centrifugation units. A composition resulting from said method comprises less than 1% of DNA contaminants and less than 1% of protein contaminants with respect to the crude supernatant.

The invention also relates to compositions that can be obtained by any one of the manufacturing methods for the particles according to the invention.

Typically, these compositions comprise less than 30% of DNA contaminants and less than 45% of protein contaminants with respect to the crude supernatant. More particularly, the compositions according to the invention comprise less than 30% of DNA contaminants and less than 2% of protein contaminants with respect to the crude supernatant.

Optionally, the compositions according to the invention comprise less than 1% of DNA contaminants and less than 1% of protein contaminants with respect to the crude supernatant.

Finally, the invention relates to the use of a particle according to the invention, or of a composition according to the invention for the transduction of cells.

Use of the particles and compositions according to the invention is particularly advantageous for the transduction of primary cells and immortalized lines, in order to modify them transiently. The cells may be mammalian cells or from other eukaryotes. In particular, the transduction of these cells may be carried out in vivo, in vitro or ex vivo.

The cells may receive one or two successive transductions with the particles according to the invention.

Use of the particles according to the invention for the transduction of cells makes it possible to introduce a mutation into the genome owing to their capacity to induce breaks of the double strand of DNA, to which the cells respond by mechanisms of DNA repair. For example, repair may be carried out by insertion of non-homologues ends for reconnecting two ends of DNA resulting from a double-strand break, of RNA introduced for this purpose or available in the cell.

These genome engineering systems may also be used for carrying out gene knock-out, i.e. knock-out of the expression of a gene, or even induce cell death depending on the genes targeted.

Once the particles according to the invention have been introduced into the cells, they may then be used for modifying the genome in vivo, in vitro or ex vivo.

The invention will be better understood from the examples given hereunder by way of illustration, with reference to the figures, which show respectively:

FIG. 2b is a schematic diagram of the construction of the expression cassette derived from the p8.74ΔZF-MS2-Coat encapsidation plasmid having the second zinc finger substituted by the "Coat" protein of the MS2 bacteriophage, obtained by the strategy presented in FIG. 2a;

Figure 7:
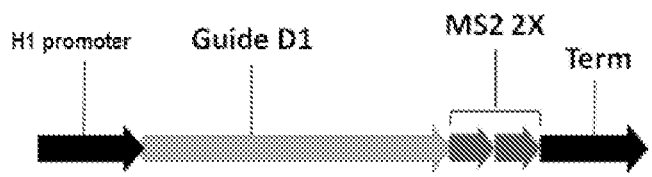
Figure 8:
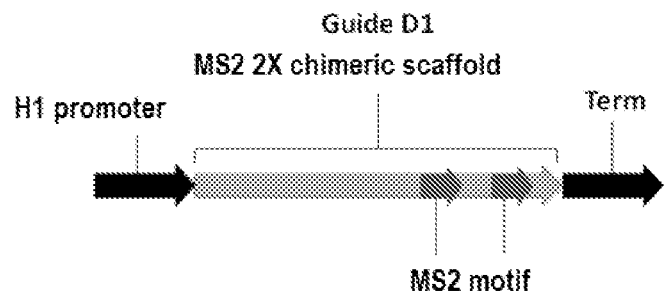
Figure 9:
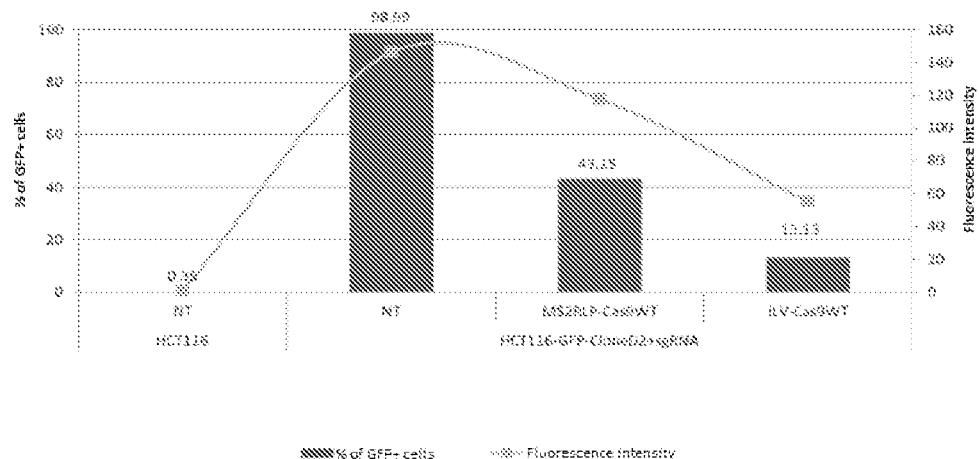
Figure 10:
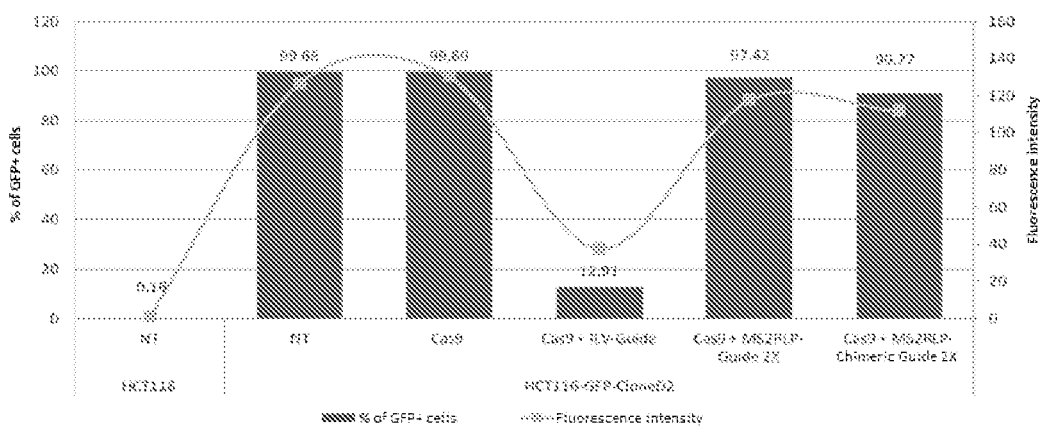
Figure 11:
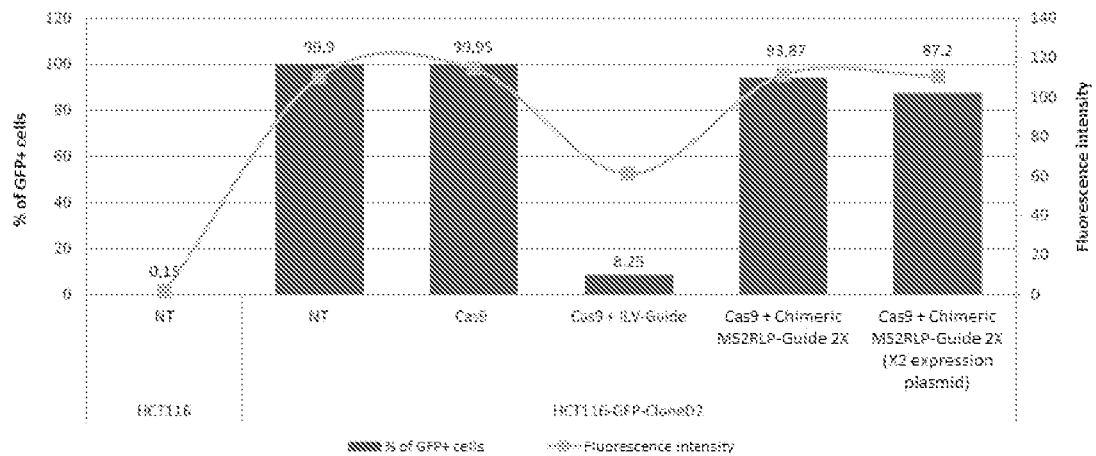
Figure 12:
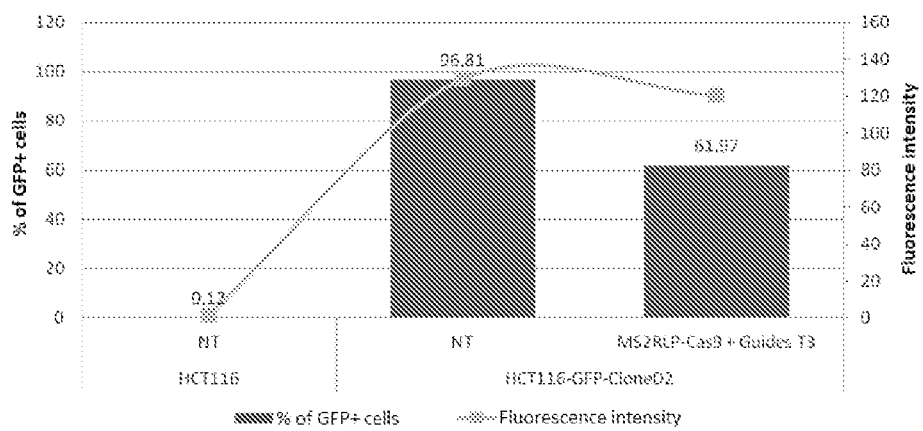
Figure 13A:
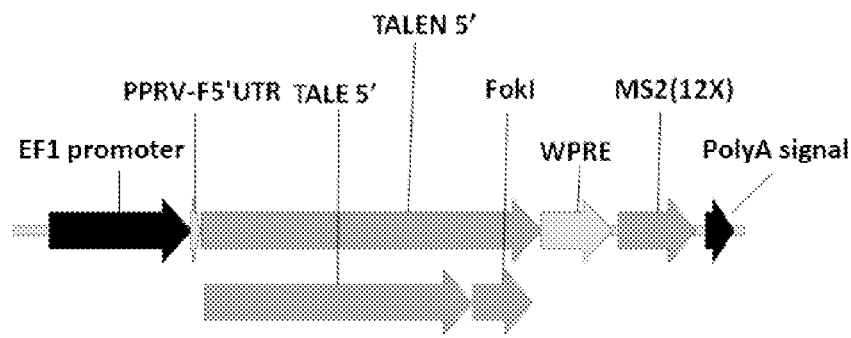
Figure 14A:
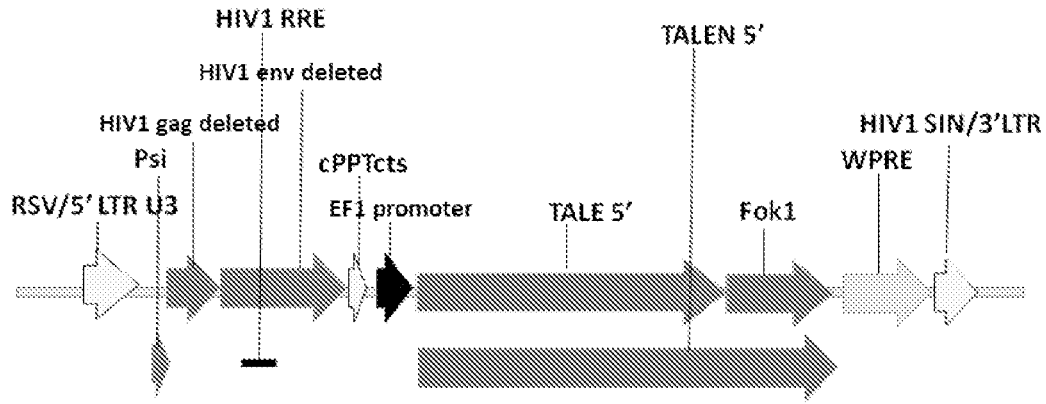
Figure 14B:
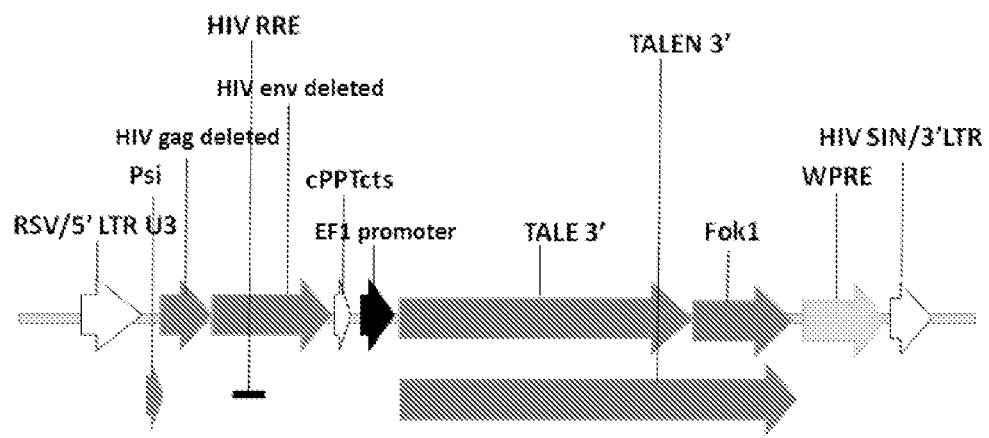
Figure 16A:
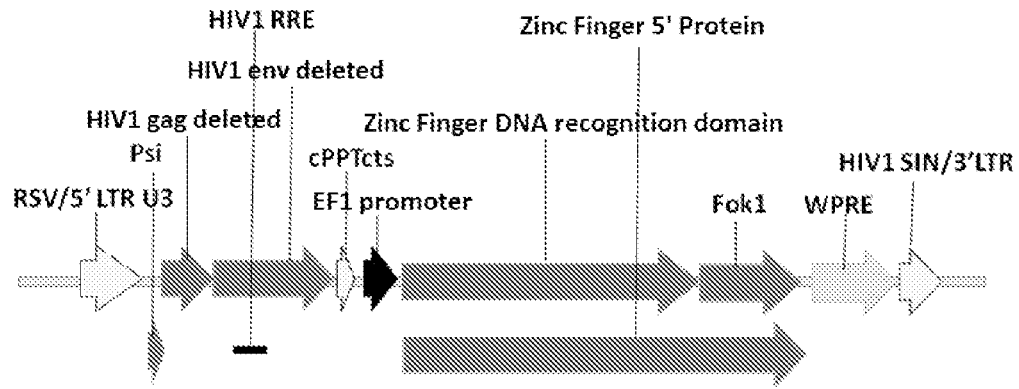
Figure 16B:
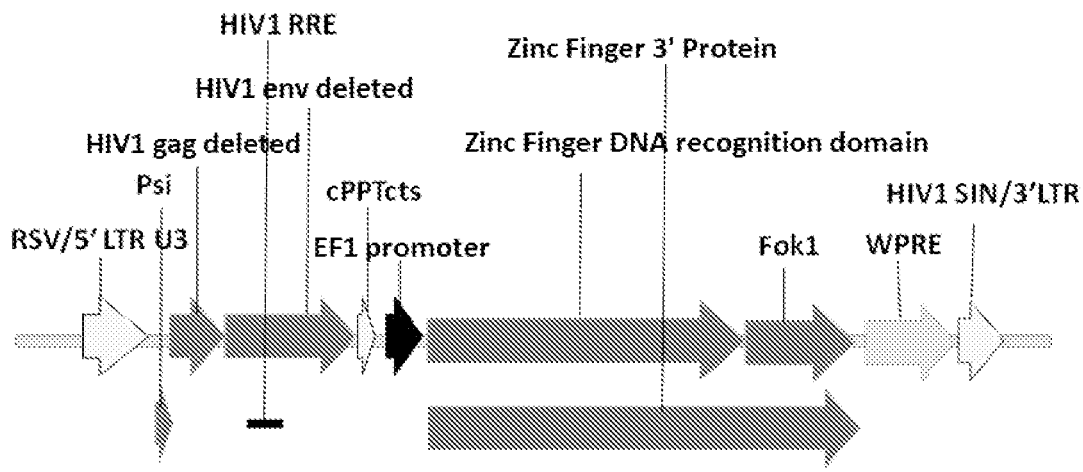
Figure 17:
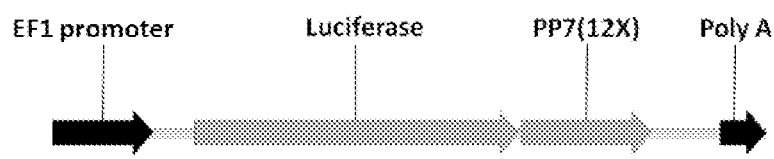
Figure 18:
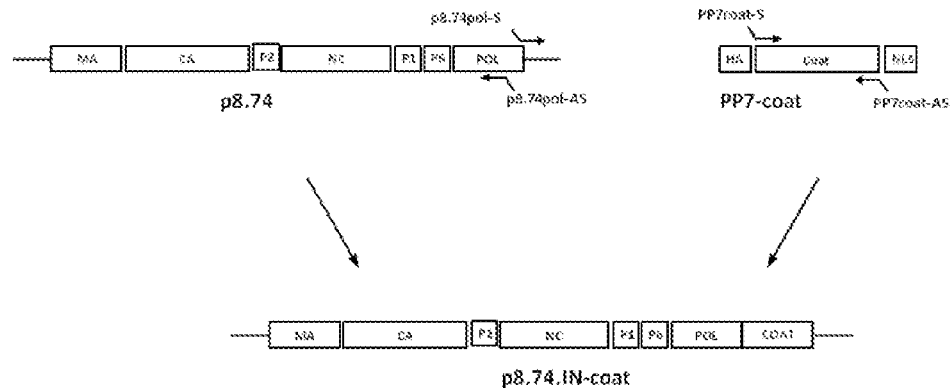
Figure 19:
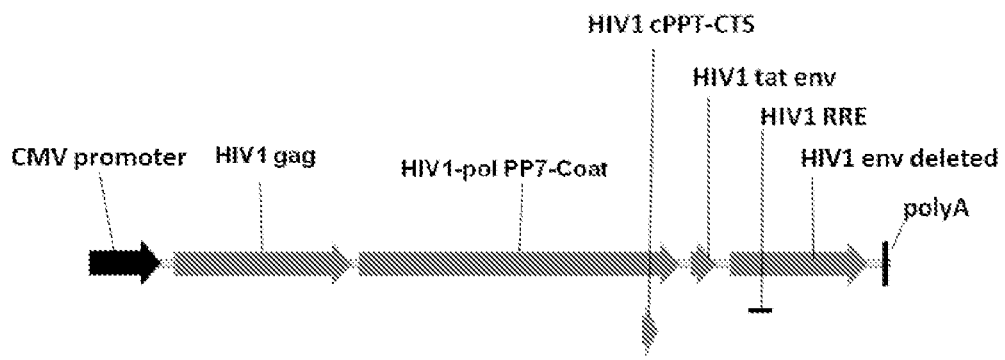
Figure 20:
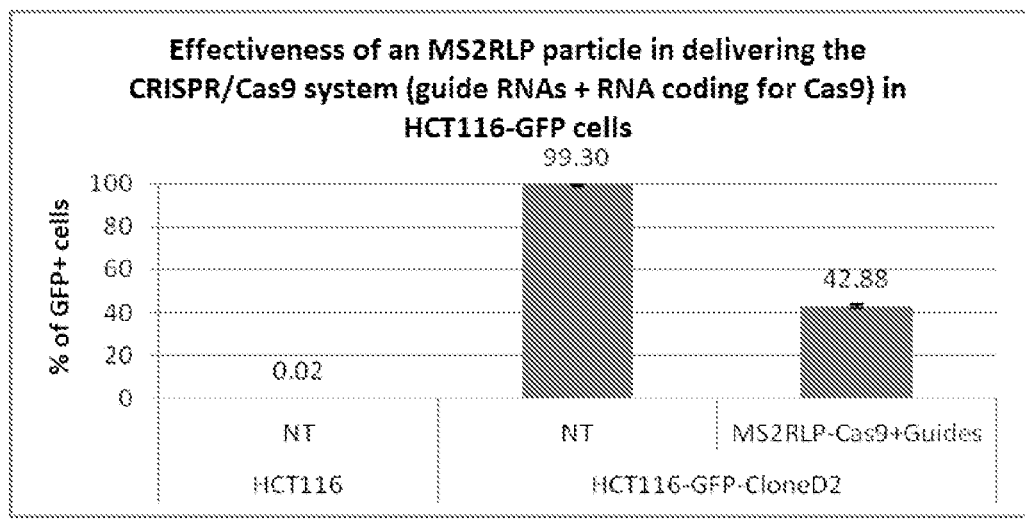
Figure 21:
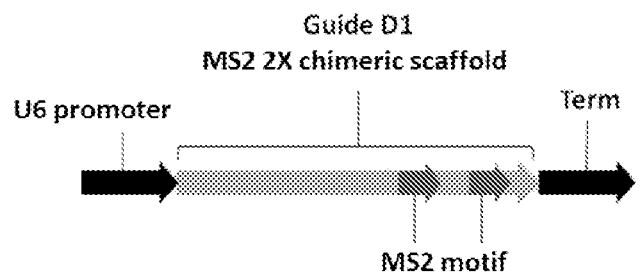
Figure 22:
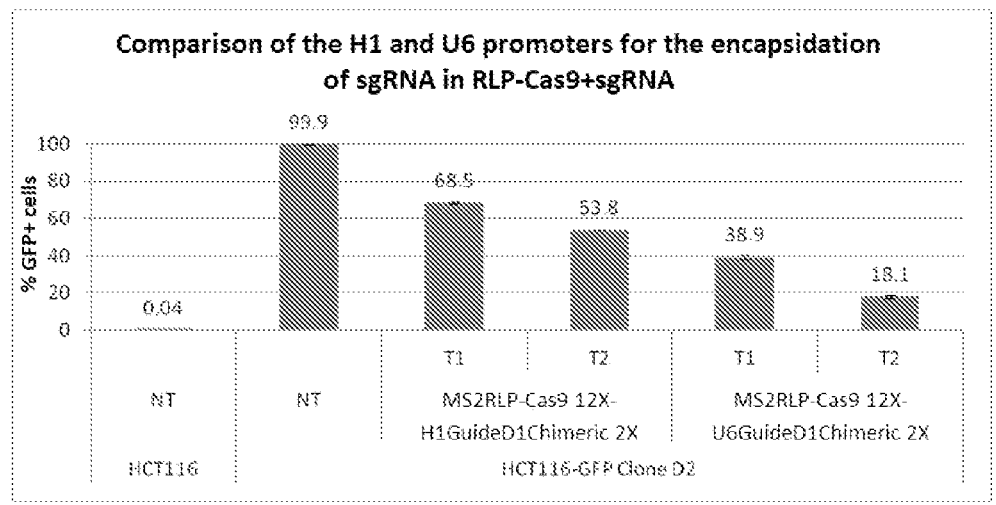
Figure 23:
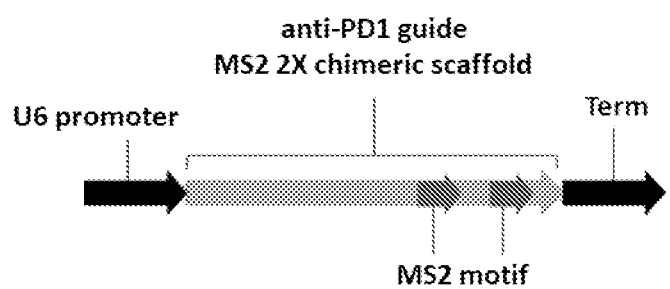
Figure 24:
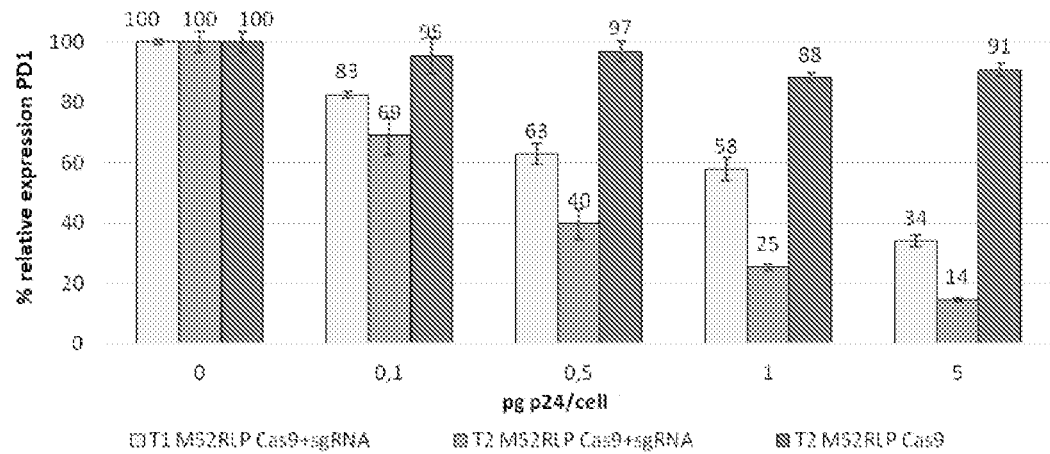
Figure 25:
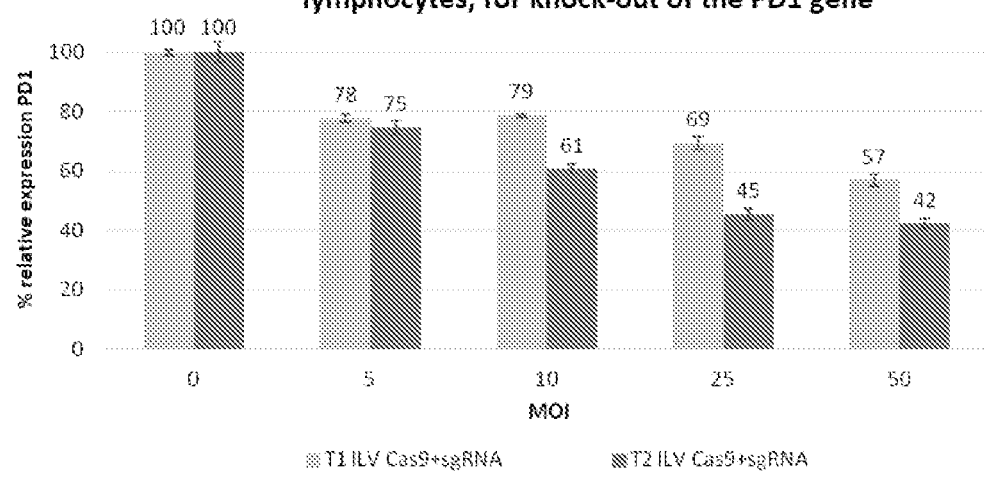
Figure 26:
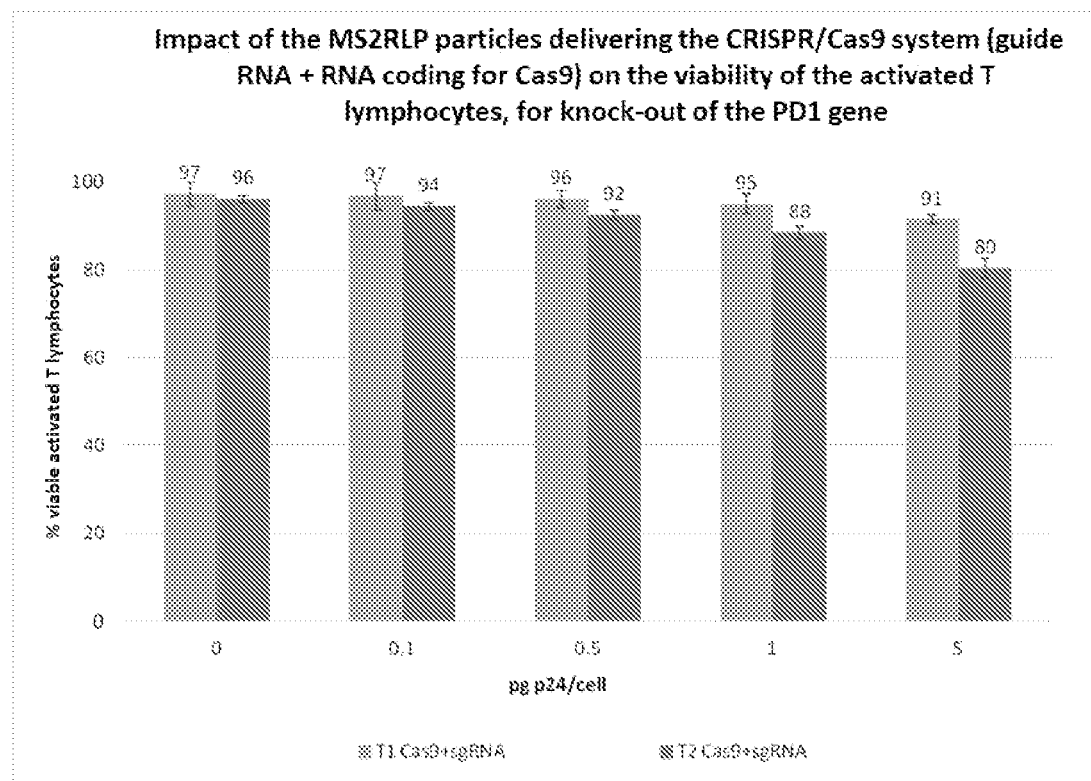
Figure 27:
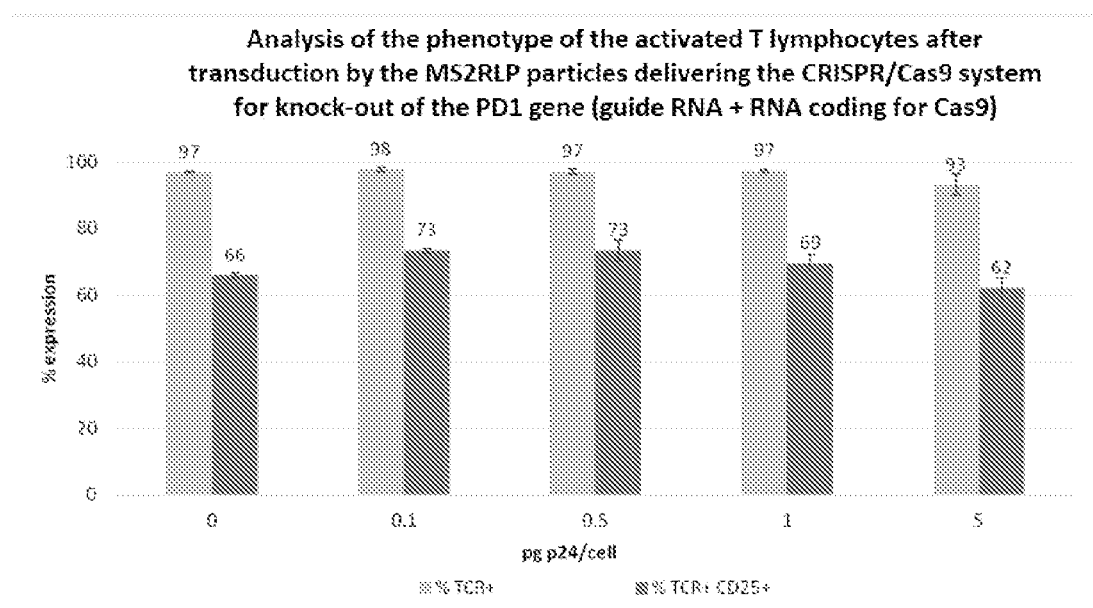
Figure 28:
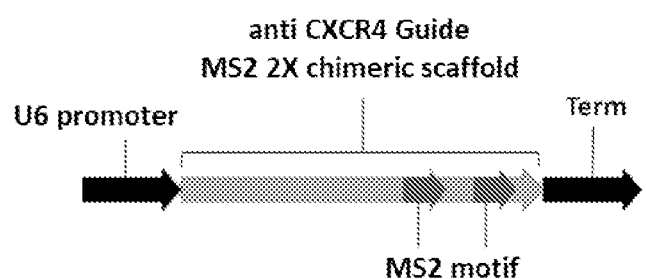
Figure 29:
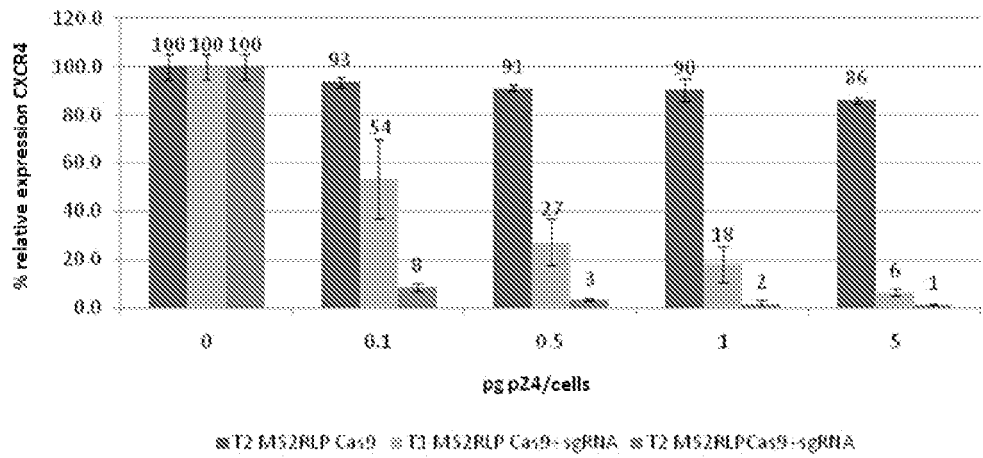
Figure 30:
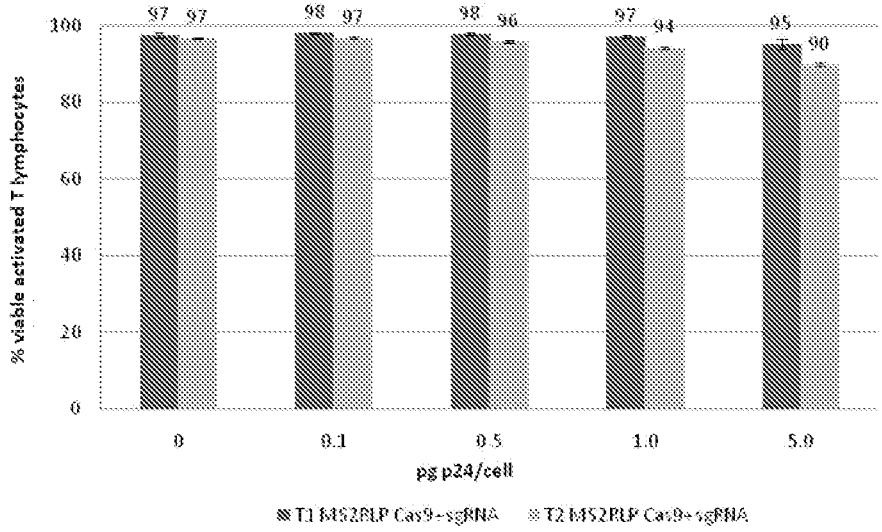
Figure 31:
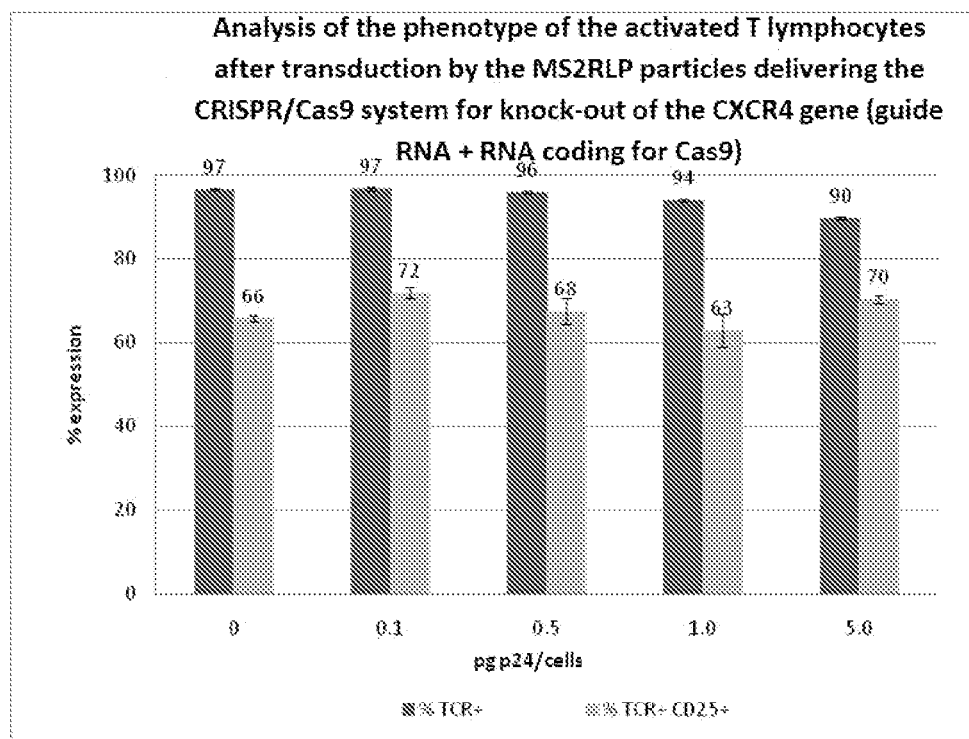

FIG. 7 is a schematic diagram illustrating the expression cassette derived from the pcDNA-H1-GuideD1-MS2 2X expression plasmid bearing a DNA sequence coding a non-coding guide RNA, comprising the scaffold, targeting the sequence of the GFP (sgRNA=guide RNA), in which 2 repetitions of the stem-loop motif of the MS2 RNA (SEQ ID No. 3) were inserted in the expression cassette downstream of the guide RNA;

FIG. 8 is a schematic diagram illustrating the expression cassette derived from the pcDNA-H1-GuideD1Chimeric-MS2 2X expression plasmid bearing a DNA sequence coding a non-coding guide RNA targeting the sequence of the GFP (sgRNA=guide RNA), of a promoter-sequence of interest-Term expression cassette, in which 2 repetitions of the stem-loop motif of the MS2 RNA (SEQ ID No.3) are included in the "scaffold" part of the chimeric guide;

FIG. 9 illustrates the effectiveness of an MS2 (NC)-RLP 12X particle according to the invention in delivering the RNA coding the Cas9 nuclease Nickase during the transduction of HCT119-GFP cells;

FIG. 10 illustrates the impact of the position of the MS2 repeat motifs for the encapsidation of guide RNAs in MS2 (NC)-RLP 12X particles according to the invention, after the transduction of the HCT119-GFP Cas9 cells;

FIG. 11 illustrates the effectiveness of production of MS2RLP particles delivering guide RNA depending on whether they are produced using a single or double quantity of the expression plasmid bearing the guide RNA for the transduction of the HCT116-GFP-Cas9 cells;

FIG. 12 illustrates the effectiveness of an MS2 (NC)-RLP 12X particle according to the invention in delivering the CRISPR/Cas9 system (guide RNA+RNA coding Cas 9), in HCT116-GFP cells;

FIG. 13a is a schematic diagram illustrating the expression cassette derived from the pcDNA.EF1.PPRV.TALEN 5'.WPRE MS2(12X) expression plasmid comprising a DNA sequence coding the RNA of the TALEN nuclease constituted by the FokI nuclease fused with a DNA binding domain, TALE, recognizing the 5' strand of the DNA;

FIG. 13b is a schematic diagram illustrating the expression cassette derived from the pcDNA.EF1.PPRV.TALEN 3'.WPRE MS2(12X) expression plasmid comprising a DNA sequence coding the RNA of the TALEN nuclease constituted by the FokI nuclease fused with a DNA binding domain, TALE, recognizing the 3' strand of the DNA;

FIG. 14a is a schematic diagram illustrating the expression cassette derived from the pILV.EF1.TALEN 5' expression plasmid comprising a DNA sequence coding the RNA of the TALEN nuclease constituted by the FokI nuclease fused with a DNA binding domain, TALE, recognizing the 5' strand of the DNA;

FIG. 14b is a schematic diagram illustrating the expression cassette derived from the pILV.EF1.TALEN 3' expression plasmid comprising a DNA sequence coding the RNA of the TALEN nuclease constituted by the FokI nuclease fused with a DNA binding domain, TALE, recognizing the 3' strand of the DNA;

FIG. 15a is a schematic diagram illustrating the expression cassette derived from the expression plasmid, pcDNA.EF1.PPRV.ZFP 5'.WPRE.MS2 (12X), bearing a DNA recognition domain of the chimeric zinc finger type with the FokI nuclease for recognition of the 5' strand of DNA;

FIG. 15b is a schematic diagram illustrating the expression cassette derived from the pcDNA.EF1.PPRV.ZFP 3'.WPRE.MS2 (12X) expression plasmid, bearing a DNA recognition domain of the chimeric zinc finger type with the FokI nuclease for recognition of the 3' strand of DNA;

FIG. 16a is a schematic diagram of the construction of the expression cassette derived from the pILV.EF1.ZFP 5' expression plasmid bearing a DNA recognition domain of the chimeric zinc finger type with the FokI nuclease for recognition of the 5' strand of DNA;

FIG. 16b is a schematic diagram of the construction of the expression cassette derived from the pILV.EF1.ZFP 3' expression plasmid bearing a DNA recognition domain of the chimeric zinc finger type with the FokI nuclease for recognition of the 3' strand of DNA;

FIG. 17 shows a schematic diagram of the expression cassette derived from the expression plasmid bearing, as RNA sequence of interest, Luciferase used for producing lentiviral particles PP7(NC)-RLP 12X, comprising the stem-loop motif PP7 repeated 12 times, according to the invention;

FIG. 18 shows a schematic diagram of modification of the lentiviral p8.74 encapsidation plasmid in order to insert a binding domain in the sequence of the integrase;

FIG. 19 shows a schematic diagram of the expression cassette derived from the encapsidation plasmid used for producing lentiviral particles PP7 (IN)-RLP according to the invention, obtained by modifying the lentiviral p8.74 encapsidation plasmid shown in FIG. VI;

FIG. 20 illustrates the effectiveness of an MS2 (NC)-RLP 12X particle according to the invention in delivering the CRISPR/Cas9 system (guide RNA+RNA coding Cas 9), in HCT116-GFP cells;

FIG. 21 is a schematic diagram of the construction of the expression cassette derived from the pcDNA-U6-GuideD1Chimeric-MS2 2X-Term expression plasmid comprising an RNA coding a non-coding RNA targeting the sequence of the GFP (sgRNA=guide RNA=Guide D1 in this case), dependent on the U6 promoter;

FIG. 22 illustrates the effectiveness of an MS2RLP particle in delivering the CRISPR/Cas9 system (guide RNA+RNA coding Cas9) in HCT116-GFP cells, as a function of the promoter allowing transcription of the guide RNA in the producer cells;

FIG. 23 is a schematic diagram of the construction of the expression cassette derived from the pcDNA-U6-Guide_antiPD1 Chimeric-MS2 2X-Term expression plasmid comprising an RNA coding a non-coding RNA targeting the PD1 gene (sgRNA=guide RNA=Guide), dependent on the U6 promoter;

FIG. 24 illustrates the effectiveness of an MS2RLP particle in delivering the CRISPR/Cas9 system (guide RNA+RNA coding Cas9) into activated primary T lymphocytes, for knock-out of the PD1 gene;

FIG. 25 shows the effectiveness of an ILV particle in delivering the CRISPR/Cas9 system (guide RNA+RNA coding Cas9) into activated primary T lymphocytes, for knock-out of the PD1 gene;

FIG. 26 shows the impact of the MS2RLP particles in delivering the CRISPR/Cas9 system for knock-out of the PD1 gene (guide RNA+RNA coding Cas9) on the viability of the activated lymphocytes;

FIG. 27 illustrates analysis of the phenotype of the activated lymphocytes after transduction by the MS2RLP particles delivering the CRISPR/Cas9 system for knock-out of the PD1 gene (guide RNA+RNA coding Cas9);

FIG. 28 is a schematic diagram of the construction of the expression cassette derived from the pcDNA-U6-Guide_antiCXCR4Chimeric-MS2 2X expression plasmid comprising an RNA coding a non-coding RNA targeting the CXCR4 gene (sgRNA=guide RNA=Guide), dependent on the U6 promoter;

FIG. 29 shows the effectiveness of an MS2RLP particle in delivering the CRISPR/Cas9 system (guide RNA+RNA coding Cas 9) in activated primary T lymphocytes, for knock-out of the CXCR4 gene;

FIG. 30 shows the impact of the MS2RLP particles delivering the CRISPR/Cas9 system for knock-out of the CXCR4 gene (guide RNA+RNA coding Cas 9) on the viability of the activated primary T lymphocytes; and FIG. 31 illustrates analysis of the phenotype of the activated T lymphocytes after transduction by MS2RLP particles delivering the CRISPR/Cas9 system for knock-out of the CXCR4 gene (guide RNA+RNA coding Cas 9).

Figure 32:
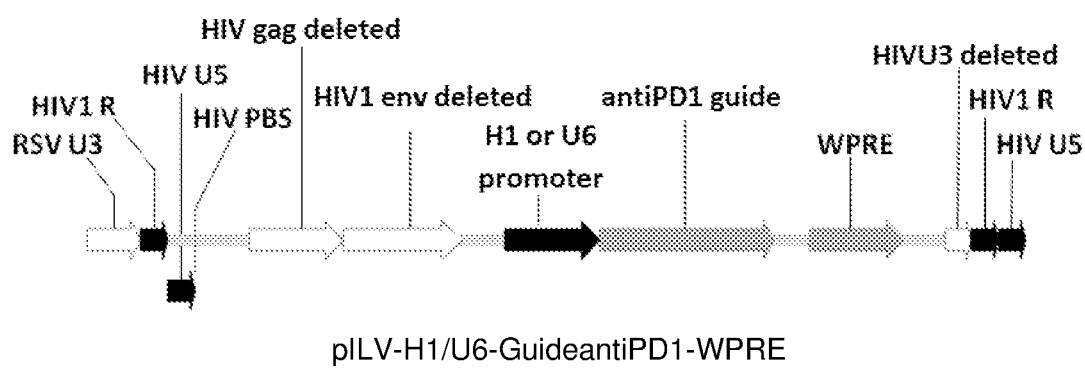
Figure 33:
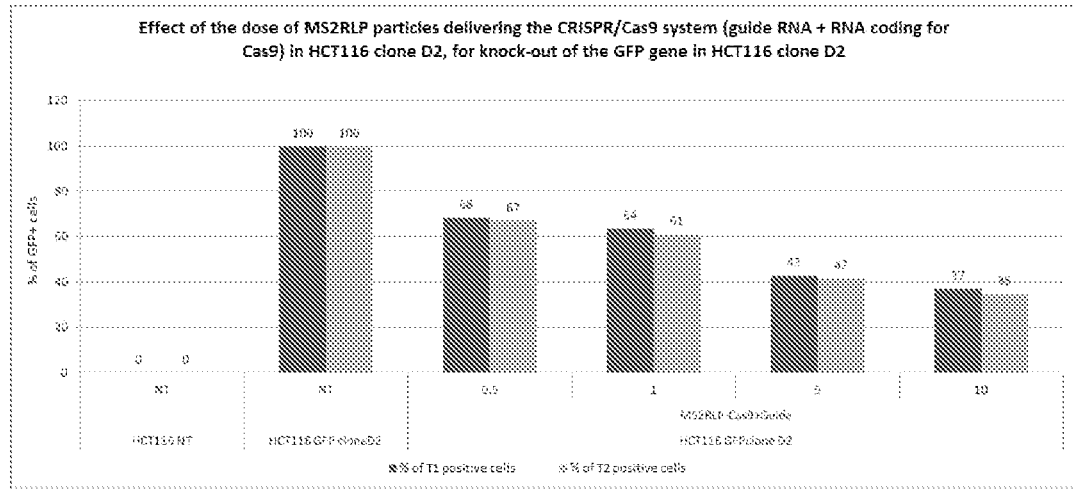
Figure 34:
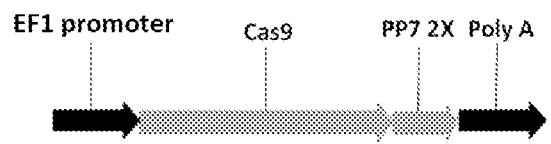
Figure 35:
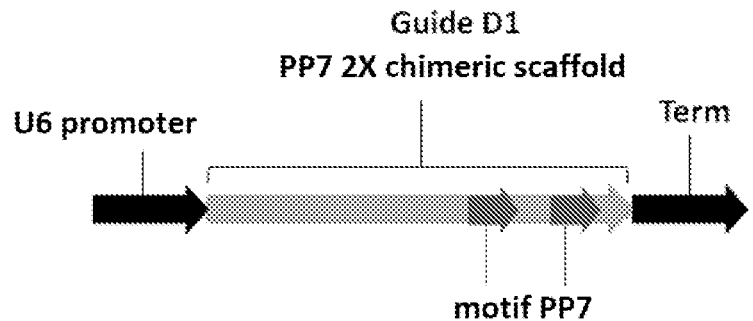
Figure 36A:
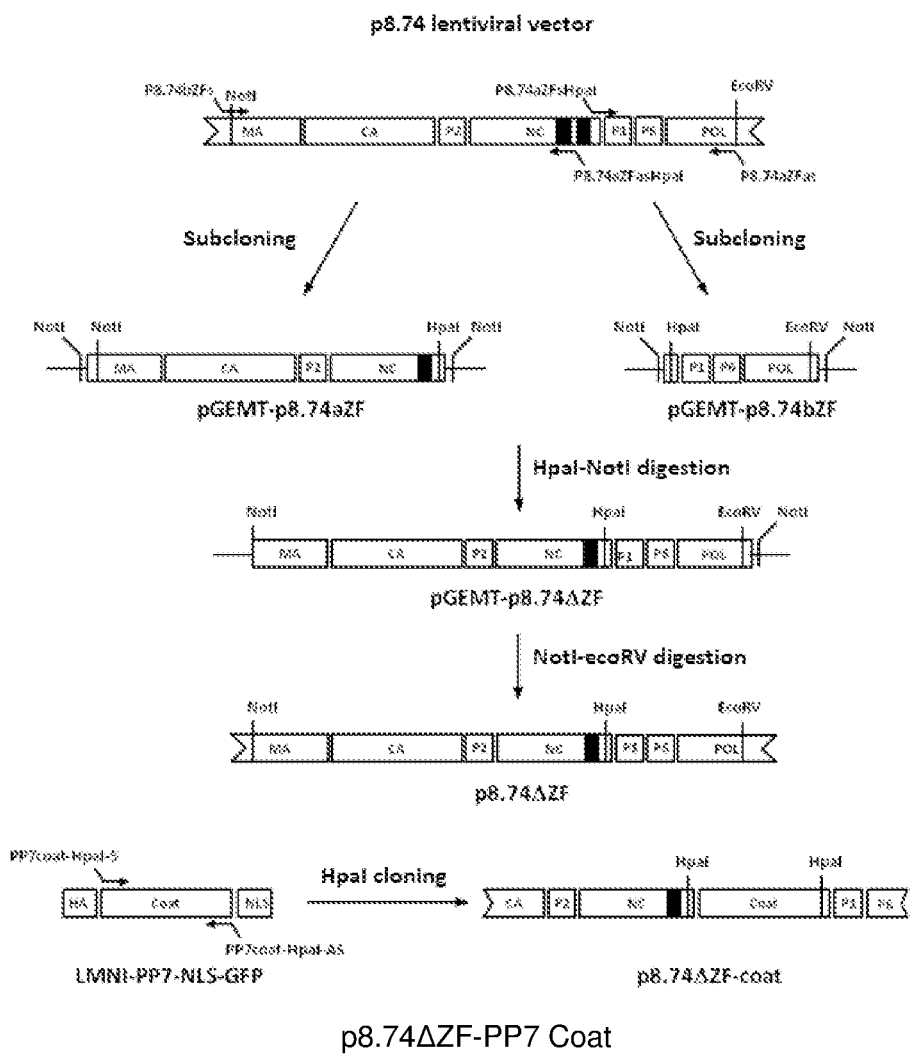
Figure 36B:
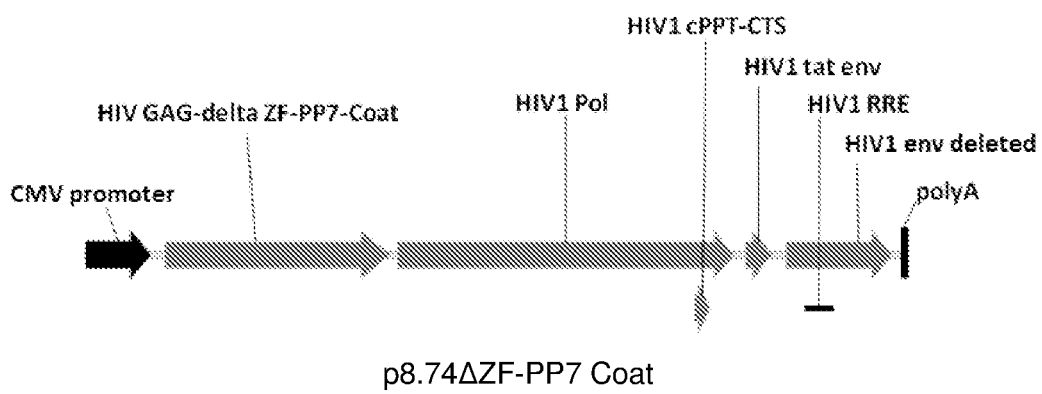
Figure 37:
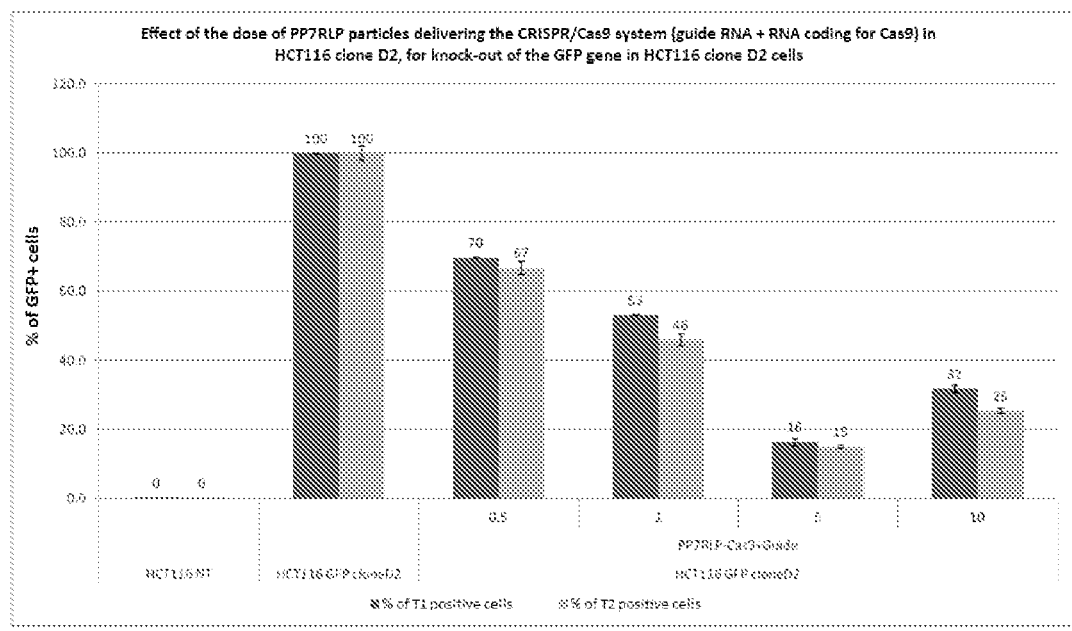
Figure 38:
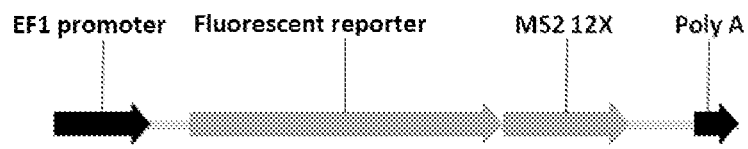
Figure 39:
Figure 40:
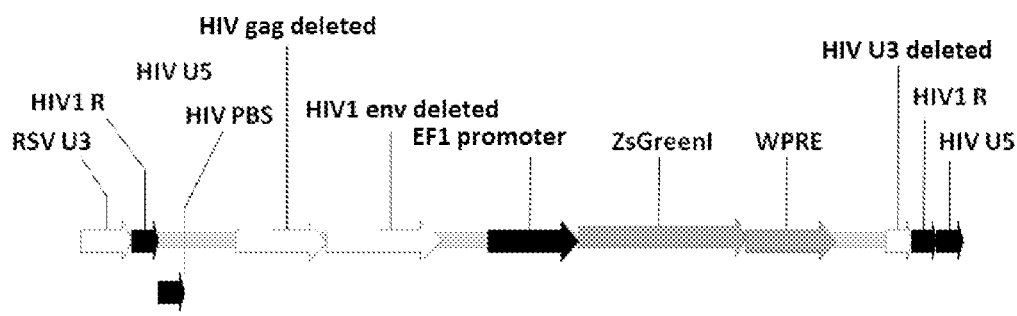
Figure 41:
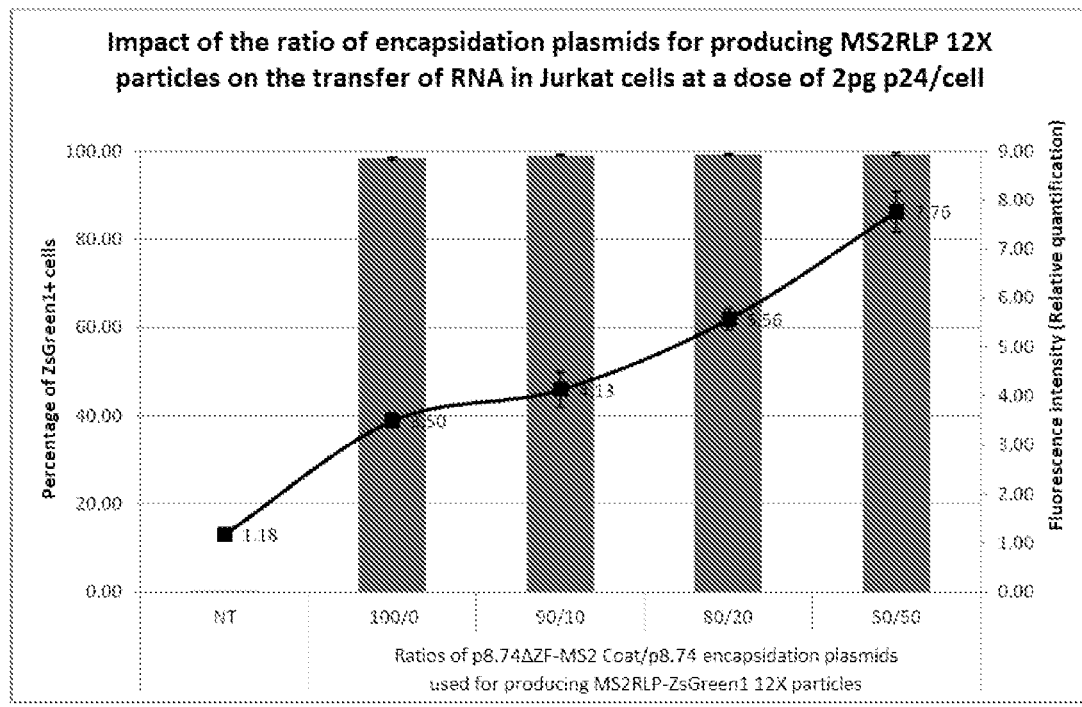
Figure 42:
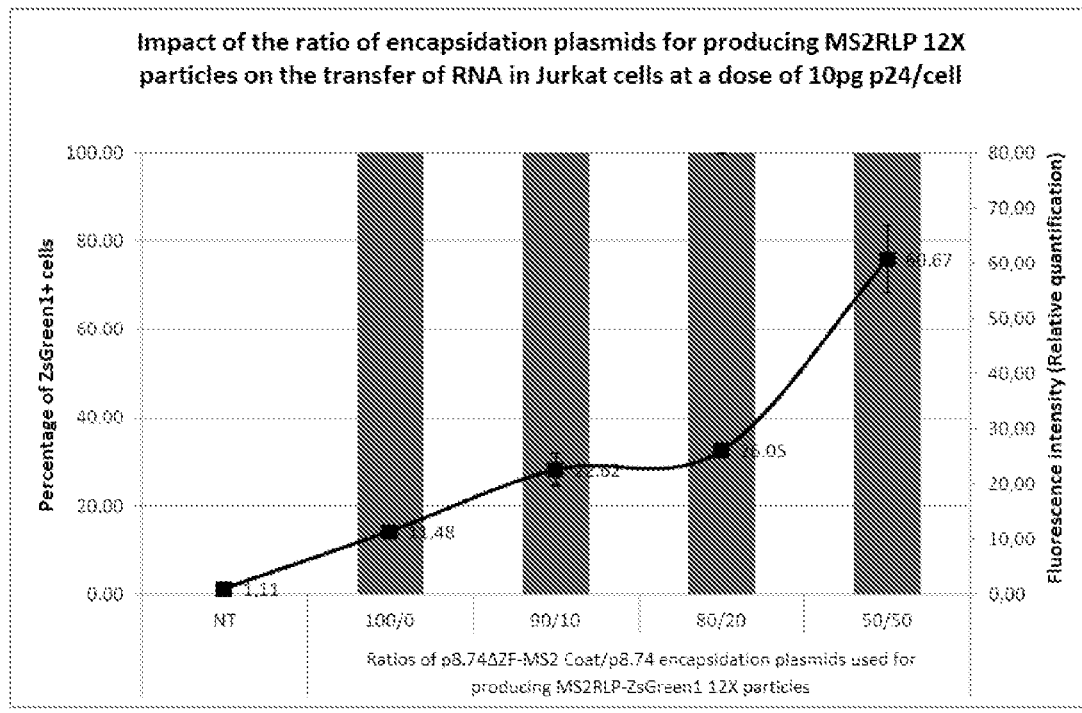
Figure 43A:
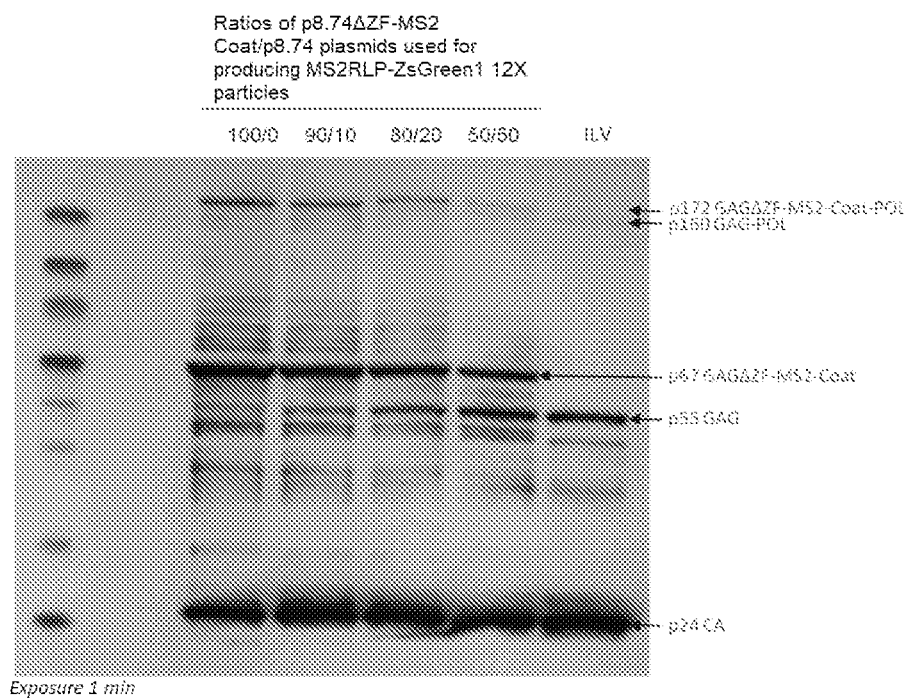
Figure 43B:
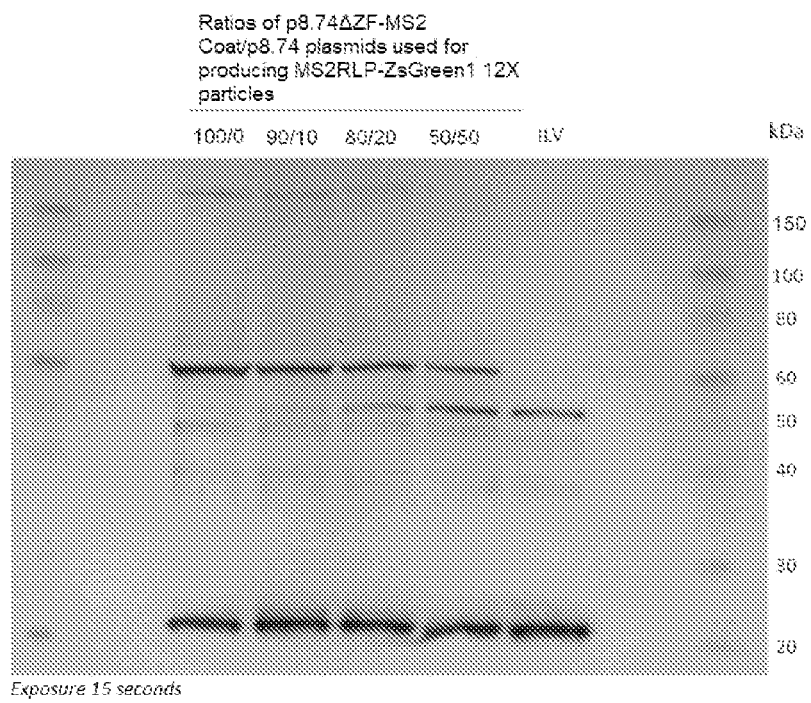
Figure 44:
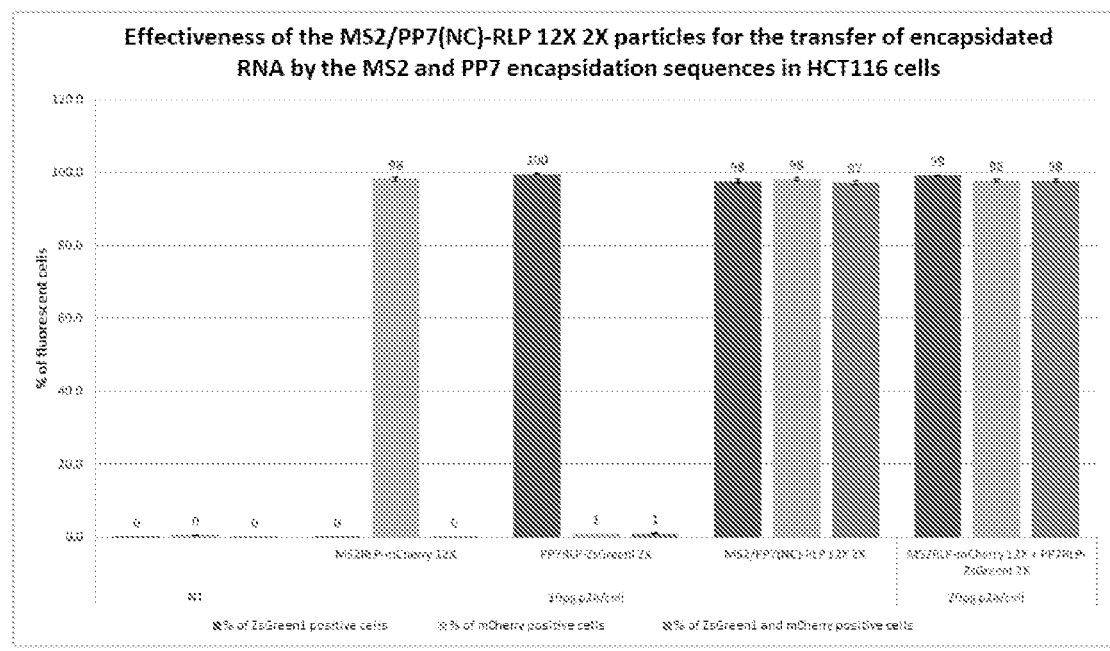

FIG. 32 is a schematic diagram of the construction of the expression cassette derived from the pILV-H1/U6-GuideantiPD1-WPRE plasmid comprising a DNA sequence coding a non-coding RNA targeting the PD1 gene (sgRNA=guide RNA=Guide);

FIG. 33 shows the effect of the dose of MS2RLP particles delivering the CRISPR/Cas9 system (guide RNA+RNA coding Cas 9) for knock-out of the GFP gene in HCT116 cloneD2 target cells;

FIG. 34 is a schematic diagram of the construction of the expression cassette derived from the pcDNA-EF1-Cas9-PP7 2X plasmid comprising a DNA sequence coding the RNA of the Cas9 nuclease;

FIG. 35 is a schematic diagram of the construction of the expression cassette derived from the pcDNA-U6-GuideD1Chimeric-PP7 2X plasmid, comprising a DNA coding a non-coding RNA targeting the sequence of the GFP (sgRNA=guide RNA), of a promoter-sequence of interest-Term expression cassette (sgRNA=guide RNA=Guide), dependent on the U6 promoter, in which 2 repetitions of the stem-loop motif of the PP7 RNA (SEQ ID No.2 and SEQ ID No.4 respectively) are included in the "scaffold" part of the chimeric guide;

FIG. 36a Illustrates the strategy for modifying the p8.74 encapsidation plasmid bearing the genes coding the structural and functional proteins (Gag, Pol) for constructing a p8.74ΔZF-PP7-Coat plasmid;

FIG. 36b is a schematic diagram of the construction of the expression cassette derived from the p8.74ΔZF-PP7-Coat encapsidation plasmid having the second zinc finger replaced with the "Coat" protein of the PP7 bacteriophage, obtained by the strategy shown in FIG. 36a;

FIG. 37 illustrates the effect of the dose of PP7RLP particles delivering the CRISPR/Cas9 system (guide RNA+ RNA coding Cas9) for knock-out of the GFP gene in HCT116 done D2 target cells;

FIG. 38 is a schematic diagram illustrating the expression cassette derived from the pcDNA.EF1.FluorescentReporter. MS2 12X expression plasmid comprising a DNA sequence coding the RNA of a fluorescent reporter, followed by 12 repetitions of the stem-loop motif of the MS2 RNA (SEQ ID No.1);

FIG. 39 is a schematic diagram illustrating the expression cassette derived from the pcDNA.EF1.FluorescentReporter. PP7 2X expression plasmid comprising a DNA sequence coding the RNA of a fluorescent reporter followed by 2 repetitions of the stem-loop motif of the PP7 RNA (SEQ ID No.2);

FIG. 40 is a schematic diagram of the construction of the expression cassette derived from the pILV-EF1-ZsGreenI-WPRE expression plasmid comprising a DNA coding the RNA of ZsGreenI;

FIG. 41 shows the effect of the wild-type GAG-POL precursor for producing MS2RLP 12X particles on the transfer of RNA in Jurkat cells at a dose of 2 pg p24/cell;

FIG. 42 shows the effect of the wild-type GAG-POL precursor for producing MS2RLP 12X particles on the transfer of RNA in Jurkat cells at a dose of 2 pg p24/cell;

FIG. 43 a and b illustrates analysis of the maturation of the MS2RLP viral particles by anti-p24 Western blot after 15 s (43b) and 1 min (43a); and FIG. 44 shows the effectiveness of the MS2/PP7 (NC)-RLP 12X 2X particles for the transfer of encapsidated RNAs by the MS2 and PP7 encapsidation sequences in HCT116 target cells.

EXAMPLE 1: COMPARISON OF TRANSFER OF THE RNA CODING CAS9 AFTER TRANSDUCTION OF A PARTICULAR CLONE OF HCT116 CELLS BY ILVS OR MS2RLP PARTICLES ACCORDING TO THE INVENTION

I. Material & Methods
1. Plasmid Construction

For this example only, the Cas9 used is Cas9 Nickase (in a mutated form).

In the following examples, unless stated otherwise, Cas9 in its wild-type form (WT) is used, the protocol remaining unchanged.

1.1 Plasmids for Producing MS2-(NC)-RLP 12X Lentiviral Particles According to the Invention Expression Plasmid for a Sequence of Interest:

The expression plasmid bears an expression cassette (FIG. 1) with or without an intron sequence or RNA stabilizing sequence. In order to transport the RNAs into the lentiviral particles, 12 repetitions of the stem-loop motif of the MS2 RNA (ctagaaaacatgaggatcacccatgtctgcag, SEQ ID No.1) were inserted in an expression cassette downstream of the sequence of the Cas9 enzyme. The promoter used is the EF1 promoter (FIG. 1) but other promoters may be used. The plasmid sequence of interest is a DNA coding the RNA of the Cas9 protein (FIG. 1), in its wild-type form (WT) or in its mutated form (N), for example Nickase.

Encapsidation Plasmid:

The lentiviral particle was modified to contain the sequence of the "Coat" protein of the MS2 bacteriophage in the nucleocapsid protein, in place of the second Zn finger domain. The p8.74 encapsidation plasmid, bearing the genes coding the structural and functional proteins (Gag, Pol), used for production of the MS2RLP particles, is modified in accordance with the strategy illustrated in FIG. 2a: this p8.74 plasmid is used for generating, by assembly PCR, a plasmid lacking the second zinc finger of the p8.74ΔZF nucleocapsid protein. The second zinc finger is substituted by the "Coat" protein of the MS2 bacteriophage by HpaI cloning, to generate the plasmid p8.74ΔZF-MS2-Coat. This gives the construct illustrated in FIG. 2b. The Pol coding sequence may be deleted or mutated in certain functional elements such as for example the sequence coding reverse transcriptase (RT) or integrase (IN) without altering the function of the MS2RLPs.

Figure 3:
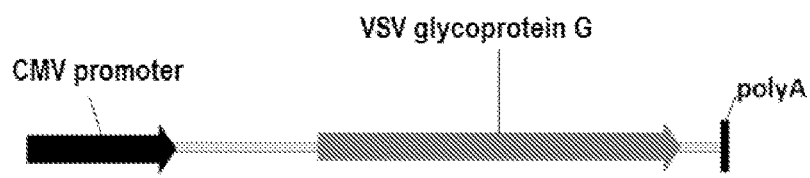
FIG. 3 is a schematic diagram of the construction of the expression cassette derived from the envelope pENV plasmid.

Envelope plasmid (pENV):

This plasmid bears the gene coding an envelope protein, which may be VSV-G coding the envelope protein of the Vesicular stomatitis virus (FIG. 3).

These plasmids are used for producing MS2-(NC)-RLP 12X lentiviral particles according to the invention. More particularly, these plasmids are used for producing MS2RLP-Cas9 12X lentiviral particles.

1.2 Plasmids for Producing Integrative Lentiviral Vectors ILV 1.2.1. Plasmids for Producing Control Integrative Lentiviral Vectors ILVCas9

Figure 4:
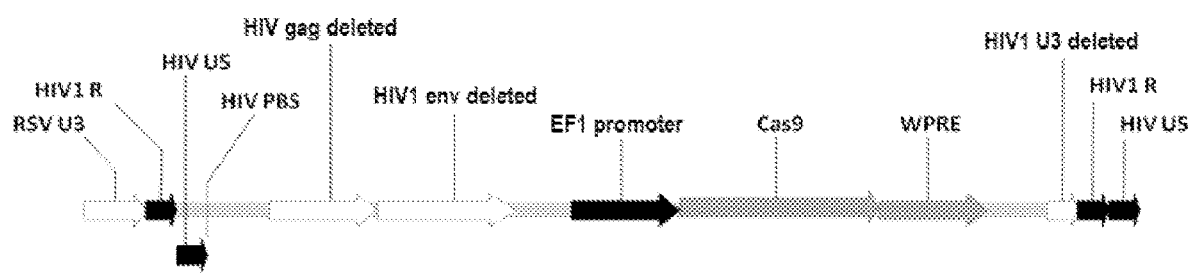
FIG. 4 is a schematic diagram of the construction of the expression cassette derived from the pILV-EF1-Cas9-WPRE expression plasmid comprising a DNA coding the RNA sequence of the Cas9 nuclease, in its wild-type form (WT) or in its mutated form (N)

Expression Plasmid for a Sequence of Interest:

The expression plasmid bears an expression cassette (FIG. 4). This plasmid may contain other elements such as the native sequence WPRE (Woodchuck Hepatitis Virus Posttranscriptional Regulatory Element) or the cPPT/CTS sequence. Viral pathogenicity is eliminated by substitution of regions of the viral genome required for retroviral replication by the transgene. The promoter used is the EF1 promoter, but other promoters may be used. The plasmid sequence of interest is a DNA coding the RNA of the Cas9 protein (FIG. 4), in its wild-type form (WT) or in its mutated form (N).

Figure 6:
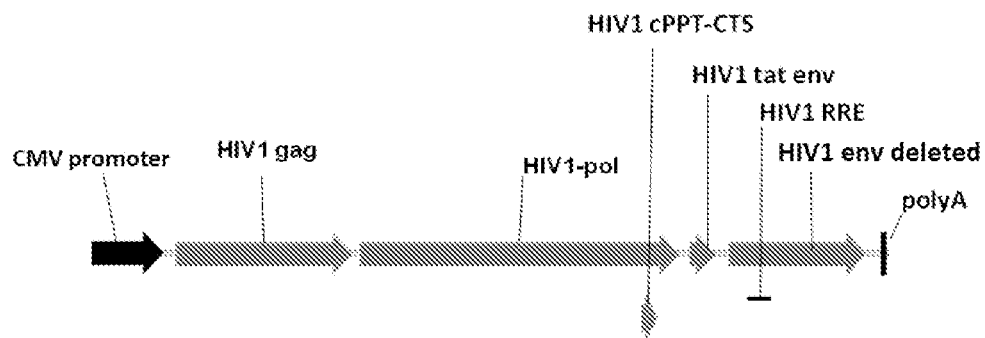
FIG. 6 is a schematic diagram of the construction of the expression cassette derived from the p8.74 encapsidation plasmid bearing the genes coding the structural and functional proteins (Gag, Pol)

Encapsidation Plasmid:

The p8.74 encapsidation plasmid bearing the genes coding the structural and functional proteins (Gag, Pol) is used for production of the integrative lentiviral vectors (FIG. 6).

Envelope Plasmid (pENV):

This plasmid is identical to the envelope plasmid used for producing MS2RLP lentiviral particles (FIG. 3).

Figure 5A:
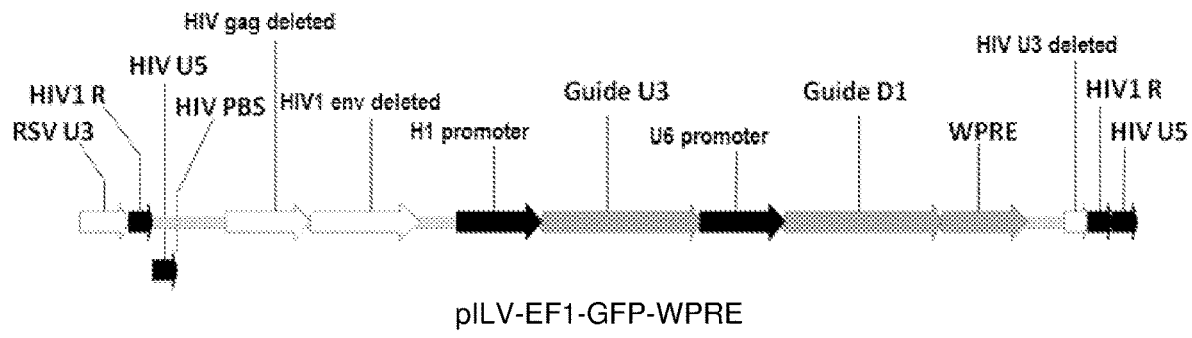
FIG. 5a is a schematic diagram of the construction of the expression cassette derived from the pILV-EF1-GFP-WPRE expression plasmid comprising a DNA coding the RNA of the GFP.

1.2.2. Plasmids for Producing ILV-GFP Integrative Lentiviral Vectors for Generating the HCT116-GFP Clone D2 Target Cells Expression Plasmid for a Sequence of Interest:

The expression plasmid bears an expression cassette (FIG. 5a). This plasmid may contain other elements such as the native sequence WPRE (Woodchuck Hepatitis Virus Posttranscriptional Regulatory Element) or the cPPT/CTS sequence. Viral pathogenicity is eliminated by substitution of regions of the viral genome required for retroviral replication by the transgene. The promoter used is the EF1 promoter, but other promoters may be used. The sequence of interest is the GFP fluorescent protein (FIG. 5a).

Encapsulation Plasmid:

The p8.74 encapsidation plasmid bearing the genes coding the structural and functional proteins (Gag, Pol) is used for production of the integrative lentiviral vectors (FIG. 6).

Envelope Plasmid (pENV):

This plasmid is identical to the envelope plasmid used for producing MS2RLP lentiviral particles (FIG. 3).

1.2.3. Plasmids for Producing Integrative Lentiviral Vectors ILV-H1-GuideU3-U6-GuideD1 for Generating the Target Cells HTC116-GFP Clone D2-H1-GuideU3-U6-GuideD1

Figure 5B:
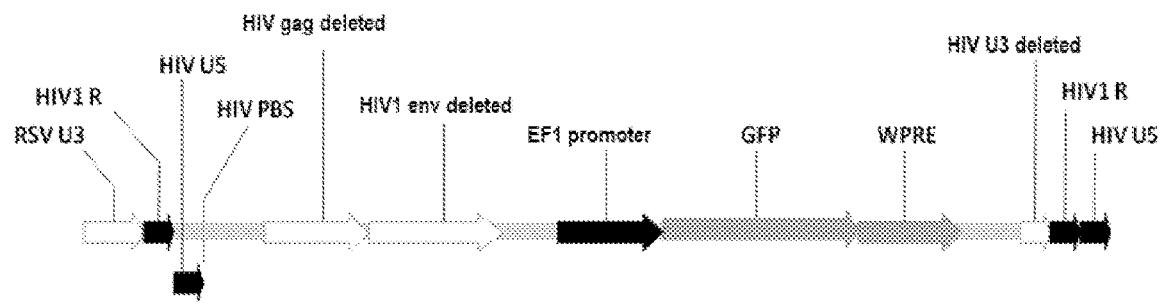
FIG. 5b is a schematic diagram of the construction of the expression cassette derived from the pILV-H1-GuideU3-U6-GuideD1-WPRE expression plasmid comprising a DNA coding two non-coding RNAs targeting the sequence of the GFP (sgRNA=guide RNA=Guide U3 and Guide D1 in this case)

Expression Plasmid for a Sequence of Interest:

The expression plasmid bears an expression cassette as described in FIG. 5b. This plasmid may contain other elements such as the native sequence WPRE (Woodchuck Hepatitis Virus Posttranscriptional Regulatory Element) or the cPPT/CTS sequence. Viral pathogenicity is eliminated by substitution of regions of the viral genome required for retroviral replication by the transgene. The promoters used are H1 and U6, but other promoters may be used. The sequences of interest are two non-coding RNAs targeting the sequence of the GFP, called guide U3 and guide D1 hereinafter (sgRNA=guide RNA) (FIG. 5b).

Encapsulation Plasmid:

The p8.74 encapsidation plasmid bearing the genes coding the structural and functional proteins (Gag, Pol) is used for production of the integrative lentiviral vectors (FIG. 6).

Envelope Plasmid (pENV):

This plasmid is identical to the envelope plasmid used for producing MS2RLP lentiviral particles (FIG. 3)

2. Production of the Batches of Lentiviral Particles and Lentiviral Vectors

After transfection of the plasmids on producer cells, the supernatants are harvested and used crude or concentrated/purified according to one of the methods mentioned hereunder, described in application WO 2013/014537.

2.1 Production of the Lentiviral Particles and Lentiviral Vectors

Production is carried out in a 10-stack CellSTACK (6360 $cm^2$, Corning) with HEK293T producer cells (ATCC, CRL-11268), cultured in Dulbecco's Modified Eagle's Medium (DMEM, Gibco, Paisley, UK) supplemented with 1% penicillin/streptomycin and 1% of ultraglutamine (PAA) at 37° C. in a humid atmosphere at 5% $CO_2$. For each batch (MS2-(NC)RLP 12X and ILV), the transfection mixture consists of the following three plasmids:
One of the expression plasmids described above, depending on whether a particle (MS2-(NC)RLP 12X) or a vector (ILV) is being formed,
p8.74ΔZF Coat (MS2-(NC)-RLP 12X) or p8.74 (ILV)
pENV bearing the envelope VSV-G.

Figure 1:
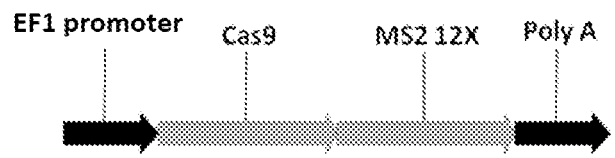
FIG. 1 is a schematic diagram illustrating the expression cassette derived from the pcDNA-EF1-Cas9-MS2 12X expression plasmid comprising a DNA sequence coding the RNA of the Cas9 nuclease, in its wild-type form (WT) or in its mutated form (N)
Figure 2A:
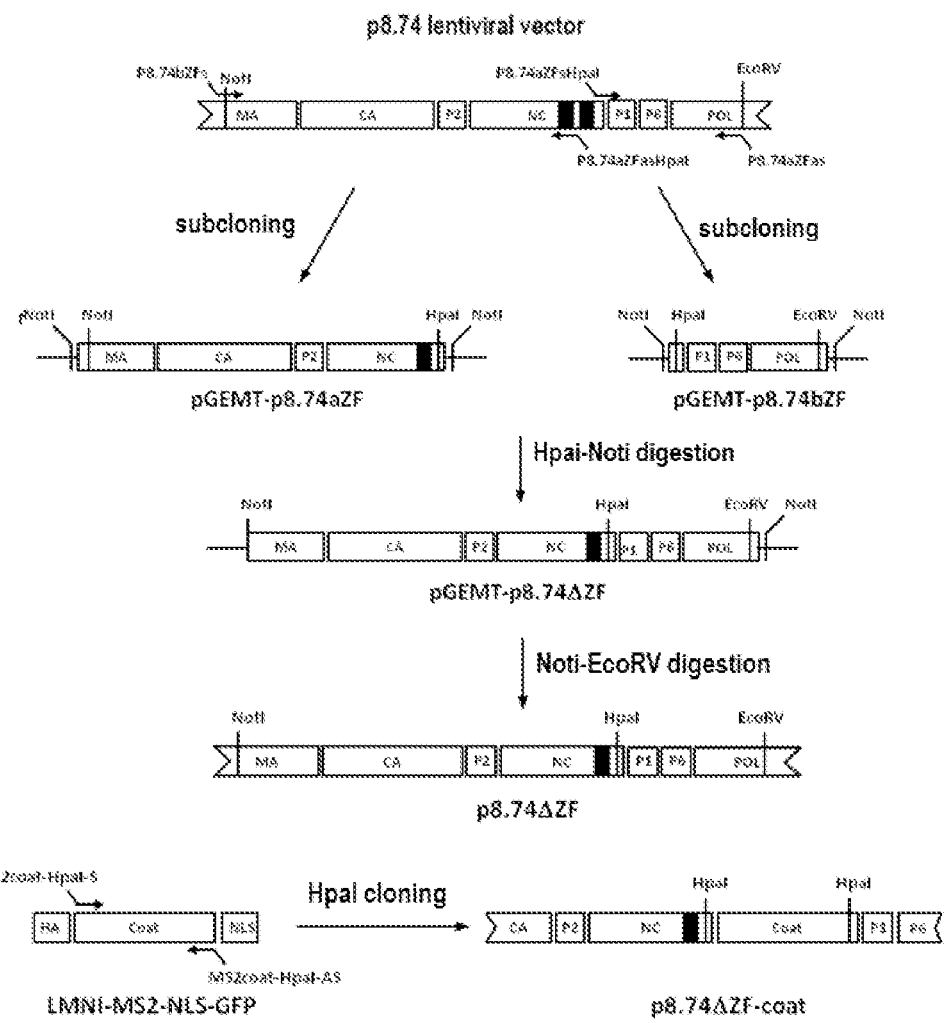
FIG. 2a illustrates the strategy for modifying the p8.74 encapsidation plasmid bearing the genes coding the structural and functional proteins (Gag, Pol) for constructing a p8.74ΔZF-MS2-Coat.
Figure 2B:
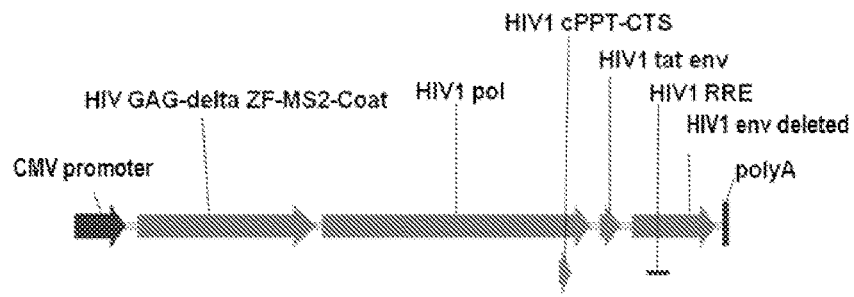

More particularly, for batch MS2RLP-Cas9 12X, the transfection mixture consists of the following three plasmids:
the pcDNA-EF1-Cas9-MS2 12X expression plasmid (the expression cassette of which is illustrated in FIG. 1)
the p8.74ΔZF-MS2 Coat plasmid (the expression cassette of which is illustrated in FIG. 2b)
the pENV plasmid bearing the envelope VSV-G (the expression cassette of which is illustrated in FIG. 3).

More particularly, for the batches ILV-GFP, ILV-H1-GuideU3-U6-GuideD1 or ILV-Cas9, the transfection mixture consists of the following three plasmids:
the expression plasmid pILV-EF1-GFP-WPRE (the expression cassette of which is illustrated in FIG. 5a) or pILV-H1-GuideU3-U6-GuideD1-WPRE (the expression cassette of which is illustrated in FIG. 5b) or pILV-EF1-Cas9-WPRE (the expression cassette of which is illustrated in FIG. 4), respectively
the p8.74 plasmid (the expression cassette of which is illustrated in FIG. 6)
the pENV plasmid bearing the envelope VSV-G (the expression cassette of which is illustrated in FIG. 3).

The respective proportions of the plasmids are as follows: 40% of the expression plasmid, 30% of the p8.74 plasmid (or p8.74ΔZF), 30% of the pENV plasmid.

24 hours after standard transfection with calcium phosphate, the culture supernatant is replaced with fresh unsupplemented DMEM medium. The producer cells are incubated at 37° C./5% $CO_2$. After changing the medium, the supernatant is harvested four times (32 h, 48 h, 56 h and 72 h post-transfection). Each collection is clarified by 5 min centrifugation at 3000 g before being microfiltered on a 0.45 μm filter (Stericup®, Millipore). All the collections are then pooled to compose the crude supernatant.

2.2 Concentration and Purification of the Lentiviral Vectors and Lentiviral Particles The vectors and particles are concentrated and purified by one of the following two methods:
Method P1 envisages frontal ultrafiltration of the supernatant on central centrifugation units.
Method P2 envisages tangential ultrafiltration and then diafiltration of the supernatant. The crude supernatant is concentrated and purified by tangential ultrafiltration using polysulphone hollow-fibre cartridges. The supernatant is treated by diafiltration for 20 diavolumes in continuous mode against DMEM or TSSM buffer. After diafiltration, the retentate is recovered and then concentrated again by frontal ultrafiltration on central centrifugation units.

For Example 1, the supernatants are harvested and used concentrated/purified according to method P1.

3. Titration of the Batches of Lentiviral Particles and Lentiviral Vectors 3.1 Titration of the functional particles by qPCR The HCT116 titration cells (ATCC, CCL-247) are seeded in a 96-well plate in 100 μL of DMEM supplemented with 10% FCS, 100 μg/mL streptomycin, 100 U/mL penicillin and 2 mM L-Gln (L-glutamine) and then incubated for 24 h at 37° C./5% $CO_2$. Six serial dilutions are carried out for each vector as well as for an internal standard. The titration cells are transduced with these serial dilutions in the presence of Polybrene® 8 μg/mL (Sigma) and then incubated for three days at 37° C./5% $CO_2$. For each series of samples, a well of cells that have not been transduced is added as a control. The titration cells are then trypsinized and the titre (Transduction Unit/mL) is determined by qPCR after extraction of the genomic DNA using the Nucleospin tissue gDNA extraction kit (Macherey-Nagel). The titre obtained (TU/mL) by qPCR is normalized with the internal standard, of which titre was determined beforehand by FACS.

3.2 Quantification of the Physical Particles by ELISA D24 Assay

The p24 capsid protein is detected directly on the viral supernatant using, and following the recommendations of, the HIV-1 p24 ELISA kit (Perkin Elmer). The p24 protein captured is complexed with a biotinylated polydonal antibody, and then detected by a streptavidin conjugated with horseradish peroxidase (HRP). The resultant complex is detected by spectrophotometry after incubation with the ortho-phenylenediamine-HCl substrate (OPD) producing a yellow coloration that is directly proportional to the quantity of p24 protein captured. The absorbance of each well is quantified with the Synergy H1 Hybrid plate reader (Biotek) and calibrated against the absorbance of a standard range of p24 protein. The viral titre expressed as physical particles per ml is calculated from the concentration of p24 protein obtained, knowing that 1 µg of p24 protein corresponds to $10^4$ physical particles.

4. Generation of Target Cells and Transduction by MS2-(NC)-RLP 12X Lentiviral Particles According to the Invention This example aims to show that it is possible to transfer RNA coding the Cas9 nuclease via non-integrative MS2RLP particles, and that at the end of this RNA transfer, for generating double-stranded DNA breaks allowing knock-out of a target gene.

4.1 HCT116-GFP Clone D2 Target Cells

The HCT116-GFP Clone D2 target cells are obtained by transduction of HCT116 cells (ATCC, CCL 247) at MOI120 in the presence of 8 µg/mL of Polybrene® with an integrative lentiviral vector (ILV) expressing GFP. The HCT116-GFP Clone D2 target monoclonal line only containing a single copy of DNA coding GFP was obtained by limit dilution of the HCT116-GFP polyclonal line (prepared from the expression plasmid in FIG. 5a) and screening of the clones by quantification of the number of integrated copies of the GFP sequence by quantitative PCR.

4.2 HCT116-GFP CloneD2-H1-GuideU3-U6-GuideD1 Target Cells and Transduction by MS2-NC)-RLP 12X Lentiviral Particles According to the Invention The HCT116-GFP Clone D2 target cells are seeded in a 24-well plate at 25000 cells/cm² and incubated for 24 h at 37° C./5% $CO_2$. Firstly the cells are transduced by the ILV-H1-GuideU3-U6-GuideD1 vectors (prepared from the expression plasmid in FIG. 5b) at MOI40, in the presence of 8 µg/mL Polybrene®. The transduction supernatant is removed 4 hours later and replaced with fresh supplemented culture medium.

One week after transduction with ILV-H1-GuideU3-U6-GuideD1, the HCT116-GFP CloneD2-H1-GuideU3-U6-GuideD2 target cells are transduced by the ILV-EF1-Cas9 vectors at MOI140 (prepared from the expression plasmid in FIG. 4) or the MS2RLP-Cas9 particles at a dose of 10 pg p24/cell, in the presence of 8 µg/mL Polybrene®. A cell defence mechanism inhibitor, BX795 (Invivogen), is used at a concentration of 6 µM in the case of the MS2RLP particles. The transduction supernatant is removed 4 hours later and replaced with fresh supplemented culture medium. At D14 post-transduction, the cells are recovered and the percentage of cells expressing GFP is quantified by cytometry (Macs Quant VYB, Miltenyi Biotec).

II. Results

The purpose of this experiment is to compare the effectiveness of transfer of RNA coding Cas9 by the transduction of HCT116-GFP-CloneD2-H1-GuideU3-U6-GuideD1 target cells with ILV-Cas9 vectors or MS2RLP-Cas9 12X particles. Firstly, the results presented in FIG. 9 show that the non-transduced (NT) HCT116 cells are not fluorescent (<0.4% of GFP positive cells), whereas 99% of the HCT116-GFP-CloneD2-H1-GuideU3-U6-GuideD1 target cells are fluorescent. Only 13% of the HCT116-GFP-CloneD2-H1-GuideU3-U6-GuideD1 target cells transduced by the ILV-Cas9 vector are still fluorescent. When the HCT116-GFP-CloneD2-H1-GuideU3-U6-GuideD1 target cells are transduced by the MS2RLP-Cas9 12X particles, a decrease in the number of fluorescent cells of the order of 57% is observed. This shows that 57% of the cells have undergone knock-out of the GFP sequence in their genome. The MS2-(NC)-RLP 12X particles containing 12 repetitions of stem-loop sequences are therefore effective for transfer of the mRNA coding the Cas9 nuclease, and therefore for performing editing of the genome.

EXAMPLE 2: COMPARISON OF THE POSITION OF THE MS2 REPEAT MOTIFS FOR ENCASPIDATION OF GUIDE RNAS IN MS2 (NC)-RLP 2X PARTICLES AFTER TRANSDUCTION OF A SECOND PARTICULAR CLONE OF HCT116 CELLS

I. Material & Methods

1. Plasmid Construction 1.1 Plasmids for Producing MS2 (NC)-RLP 2X Lentiviral Particles According to the Invention Expression Plasmid for a Sequence of Interest:

The expression plasmid bears an expression cassette as described in FIG. 7 or 8, with or without an intron sequence or RNA stabilizing sequence. In order to transport the RNAs into the lentiviral particles, 2 repetitions of the stem-loop motif of the MS2 RNA (ctagaaaacatgaggatcacccatgtctgcag, SEQ ID No.1 for the conventional guide D1, ggccaacatgag-gatcacccatgtctgcagggcc SEQ ID No.3 for the chimeric guide D1) were inserted in an expression cassette either downstream of the guide RNA (conventional guide D1, FIG. 7), or included in the part of the scaffold of the guide (chimeric guide D1, FIG. 8). The promoter used is the H1 promoter but other promoters may be used such as the U6 promoter. Use of a promoter of the RNA pol III dependent type, such as H1 or U6, requires the presence of a transcription termination signal (Term). The sequence of interest is a non-coding RNA targeting the sequence of the GFP (sgRNA=guide RNA).

Encapsidation Plasmid:

The lentiviral particle was modified to contain the sequence of the "Coat" protein of the MS2 bacteriophage in the nucleocapsid protein, in place of the second Zn finger domain. The p8.74 encapsidation plasmid bearing the genes coding the structural and functional proteins (Gag, Pol) used for production of the MS2RLP 2X particles is modified in accordance with the strategy illustrated in FIG. 2a: this p8.74 plasmid is used for generating, by assembly PCR, a plasmid lacking the second zinc finger of the p8.74ΔZF nucleocapsid protein. The second zinc finger is substituted by the "Coat" protein of the MS2 bacteriophage by HpaI cloning, to generate the plasmid p8.74ΔZF-MS2-Coat. This gives the construct illustrated in FIG. 2b. The Pol coding sequence may be deleted or mutated in certain functional elements such as for example the sequence coding reverse transcriptase (RT) or integrase (IN) without altering the function of the MS2RLP 2X.

Envelope Plasmid (pENV):

This plasmid bears the gene coding an envelope protein, which may be VSV-G coding the envelope protein of the Vesicular stomatitis virus (FIG. 3).

These plasmids are used for producing MS2-(NC)-RLP 12X lentiviral particles according to the invention. More particularly, these plasmids are used for production of the lentiviral particles MS2RLP-GuideD1Classical 2X and MS2RLP-GuideD1 Chimeric 2X.

1.2 Plasmids for Producing Integrative Lentiviral Vectors ILV 1.2.1. Plasmids for Producing Control Integrative Lentiviral Vectors ILV-GuideD1

Figure 5C:
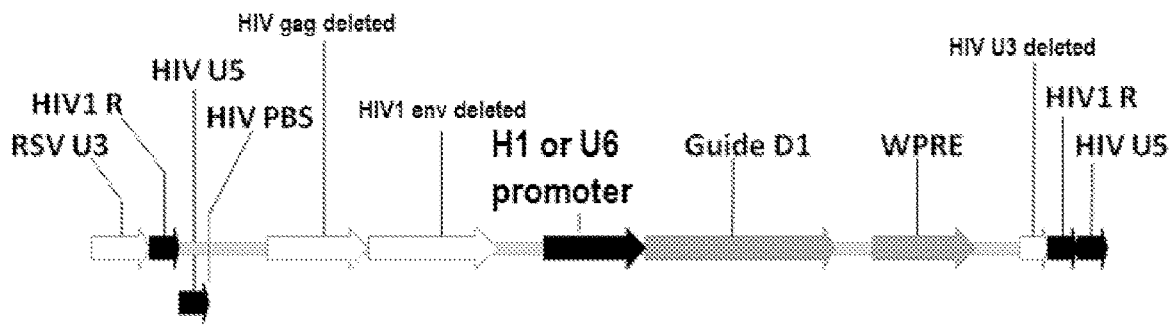
FIG. 5c is a schematic diagram of the construction of the expression cassette derived from the pILV-H1/U6-Guide-WPRE expression plasmid comprising a DNA coding a non-coding RNA targeting the sequence of the GFP (sgRNA=guide RNA=Guide)

Expression Plasmid for a Sequence of Interest:

The expression plasmid bears an expression cassette as described in FIG. 5c. This plasmid may contain other elements such as the native sequence WPRE (Woodchuck Hepatitis Virus Post-transcriptional Regulatory Element) or the cPPT/CTS sequence. Viral pathogenicity is eliminated by substitution of regions of the viral genome required for retroviral replication by the transgene. The promoters used are H1 and U6, but other promoters may be used. The sequence of interest is a guide (FIG. 5c).

Encapsidation Plasmid:

The p8.74 encapsidation plasmid bearing the genes coding the structural and functional proteins (Gag, Pol) is used for production of the integrative lentiviral vectors (FIG. 6).

Envelope Plasmid (pENV):

This plasmid is identical to the envelope plasmid used for producing MS2RLP lentiviral particles (FIG. 3).

1.2.2. Plasmids for Producing ILV-GFP Integrative Lentiviral Vectors for Generating the HCT116-GFP Clone D2 Target Cells These plasmids are prepared by a method identical to that in Example 1.

1.2.3 Plasmids for Producing ILV-Cas9 Integrative Lentiviral Vectors for Preparing the HCT116-GFP Clone D2-EF1-Cas9WT Target Cells These plasmids are prepared by a method identical to that in Example 1.

2. Production of Batches of Lentiviral Particles and Lentiviral Vectors

The lentiviral particles and the lentiviral vectors are produced as described in Example 1 and are concentrated and purified according to method P1 as described in Example 1.

More particularly, for the batch MS2RLP-GuideD1 Classical 2X and MS2RLP-GuideD1Chimeric 2X, the transfection mixture consists of the following three plasmids:

the pcDNA-H1-GuideD1-MS2 2X expression plasmid (the expression cassette of which is illustrated in FIG. 7) or the pcDNA-H1-GuideD1Chimeric-MS2 2X plasmid (the expression cassette of which is illustrated in FIG. 8)

the p8.74ΔZF-MS2 Coat plasmid (the expression cassette of which is illustrated in FIG. 2b)

the pENV plasmid bearing the envelope VSV-G (the expression cassette of which is illustrated in FIG. 3).

The proportion of plasmids used is identical to that in Example 1.

3. Titration of the Batches of Lentiviral Particles and Lentiviral Vectors

The lentiviral particles and the lentiviral vectors are titrated as described in Example 1.

4. Generation of Target Cells and Transduction by MS2-NC)-RLP 2X Lentiviral Particles According to the Invention This example aims to determine whether the position of the MS2 repeated stem-loop motifs for encapsidation of guide RNA in MS2RLP particles has an impact on the effectiveness of the particles for knock-out of a target gene.

4.1 HCT116-GFP CloneD2 Target Cells

This clone is prepared by a method identical to that in Example 1.

4.2 HCT116-GFP CloneD2-Cas9 Target Cells and Transduction by MS2-(NC)-RLP 2X Lentiviral Particles According to the Invention The HCT116-GFP Clone D2 cells are seeded in a 24-well plate at 25000 cells/cm$^2$ and incubated for 24 h at 37° C./5% $CO_2$. Firstly the cells are transduced by the ILV-Cas9 vectors, at MOI140, in the presence of 8 µg/mL Polybrene®. The transduction supernatant is removed 4 hours later and replaced with fresh supplemented culture medium. One week after transduction with the ILV-Cas9 vectors, the HCT116-GFP CloneD2-Cas9 target cells are transduced by the MS2 (NC)-RLP 2X particles delivering the anti-GFP guide RNAs (classical or chimeric) at a dose of 10 pg p24/cell, or by the ILV-GuideD1 vectors at MOI40, in the presence of 8 µg/mL Polybrene®. A cell defence mechanism inhibitor, BX795 (Invivogen), is used at a concentration of 6 µM in the case of the MS2RLP particles. The transduction supernatant is removed 4 hours later and replaced with fresh supplemented culture medium. At D14 post-transduction by the MS2RLP-guides-MS2 2X, the cells are recovered and the percentage of cells expressing GFP is quantified by cytometry (Macs Quant VYB, Miltenyi Biotec).

II. Results

The purpose of this experiment is to compare the position of the MS2 repeat motifs for encapsidation of guide RNAs in the MS2RLP 2X particles after transduction. Firstly, the results presented in FIG. 10 show that the non-transduced (NT) HCT116 cells are not fluorescent (<0.16% of GFP positive cells), whereas more than 99% of the HCT116-GFP CloneD2 target cells are fluorescent. Just 13% of the HCT116-GFP CloneD2-Cas9 target cells transduced by the ILV-GuideD1 vectors are still fluorescent. When the HCT116-GFP doneD2-Cas9 target cells are transduced by the MS2RLP 2X-Guide particles, a very slight decrease in the number of fluorescent cells of 2% is observed for the MS2RLP-GuideD1 Classical 2X transporting the classical guides and a larger decrease of the order of 10% for the MS2RLP-GuideD1Chimeric 2X transporting the chimeric guides. The position of the MS2 repeat motifs therefore impacts the effectiveness of the MS2RLP 2X particles. Although the percentage extinction remains moderate, the results show that the MS2RLP 2X particles allow transfer of guide RNA, and therefore genome editing.

EXAMPLE 3: IMPACT OF THE SINGLE OR DOUBLE QUANTITY OF THE EXPRESSION PLASMID BEARING THE GUIDE RNA IN THE MS2 (NC)-RLP 2X PARTICLES FOR TRANSDUCTION OF THE SECOND CLONE OF HCT116 CELLS

I. Material & Methods

1. Plasmid Construction 1.1 Plasmids for Producing Integrative Lentiviral Vectors ILV 1.1.1 Plasmids for Producing ILV-Cas9 Integrative Lentiviral Vectors for Preparing the HCT116-GFP Clone D2-EF1-Cas9 Target Cells These plasmids are prepared by a method identical to that in Example 1.

1.1.2 Plasmids for producing ILV-GFP integrative lentiviral vectors for Generating the HCT116-GFP Clone D2 Target Cells These plasmids are prepared by a method identical to that in Example 1.

1.1.3 Plasmids for Producing Control Integrative Lentiviral Vectors ILV for the Guides (ILV-GuideD1)

These plasmids are prepared by a method identical to that in Example 2.

1.2 Plasmids for Producing MS2 (NC)-RLP 2X Lentiviral Particles According to the Invention.

These plasmids are prepared by a method identical to that in Example 1. More particularly, the plasmids employed for producing MS2RLP-GuideD1Chimeric 2X lentiviral particles are used.

2. Production of Batches of Lentiviral Particles and Lentiviral Vectors 2.1 Production of the Lentiviral Particles and Lentiviral Vectors Production is carried out in a 10-stack CellISTACK (6360 cm$^2$, Corning) with HEK293T producer cells (ATCC, CRL-11268), cultured in Dulbecco's Modified Eagle's Medium (DMEM, Gibco, Paisley, UK) supplemented with 1% penicillin/streptomycin and 1% of ultraglutamine (PAA) at 37° C. in a humid atmosphere at 5% $CO_2$. The MS2RLP 2X particles are produced by transfection of the following three plasmids:

One of the expression plasmids described above, used in single or double quantity depending on whether a particle is being formed (MS2-(NC)-RLP 2X) or in single quantity for an integrative vector (ILV), p8.74ΔZF Coat (MS2-(NC)-RLP 2X) or p8.74 (ILV);

pENV bearing the envelope VSV-G.

More particularly, the MS2RLP-GuideD1Chimeric 2X lentiviral particles are produced by transfection of the following three plasmids:

the pcDNA-H1-GuideD1Chimeric-MS2 2X expression plasmid (the expression cassette of which is illustrated in FIG. 8) used in single or double quantity p8.74ΔZF Coat-MS2 Coat (the expression cassette of which is illustrated in FIG. 2*b*)

pENV bearing the envelope VSV-G (the expression cassette of which is illustrated in FIG. 3).

The proportions of the plasmids are as follows: 40% of the expression plasmid, 30% of the p8.74 or p8.74ΔZF plasmid, 30% of the pENV plasmid, 60% of the expression plasmid, 20% of the p8.74 or p8.74ΔZF plasmid, 20% of the pENV plasmid, for the case when production comprises a single expression plasmid, the quantity of which is doubled.

24 hours after standard transfection with calcium phosphate, the culture supernatant is replaced with fresh unsupplemented DMEM medium. The producer cells are incubated at 37° C./5% $CO_2$. After changing the medium, the supernatant is harvested four times (32 h, 48 h, 56 h and 72 h post-transfection). Each collection is clarified by 5 min centrifugation at 3000 g before being microfiltered on a 0.45 µm filter (Stericup®, Millipore). All the collections are then pooled to compose the crude supernatant.

The ILV-Cas9 lentiviral vectors are produced as described in Example 1.

The ILV-GFP lentiviral vectors are produced as described in Example 1.

The ILV-GuideD1 lentiviral vectors are produced as described in Example 2.

2.2 Concentration and Purification of the Lentiviral Particles and Lentiviral Vectors The vectors and particles are concentrated and purified according to method P1, described in Example 1.

3. Titration of the Batches of Lentiviral Particles and Lentiviral Vectors

The lentiviral particles and the lentiviral vectors are titrated as described in Example 1.

4. Generation of Target Cells and Transduction by MS2-(NC)-RLP 2X Lentiviral Particles According to the Invention This example aims to compare the effectiveness of MS2 (NC)-RLP 2X particles for knock-out of a target gene with particles produced with a single or double quantity of the expression plasmid bearing the guideD1Chimeric RNA, targeting the sequence coding GFP contained in the HCT116-GFP cloneD2-EF1-Cas9 cells expressing the Cas9 enzyme constitutively.

4.1 HCT116-GFP cloneD2 Target Cells

This done is prepared by a method identical to that in Example 1.

4.2 HCT116-GFP cloneD2-Cas9 Target Cells and Transduction by MS2-(NC)-RLP 2X Lentiviral Particles According to the Invention The HCT116-GFP Clone D2 cells are seeded in a 24-well plate at 25000 cells/cm$^2$ and incubated for 24 h at 37° C./5% $CO_2$. Firstly the cells are transduced by the ILV-Cas9 vectors at MOI40, these vectors being as prepared in Example 2, in the presence of 8 µg/mL Polybrene®. The transduction supernatant is removed 4 hours later and replaced with fresh supplemented culture medium. One week after transduction with ILV-Cas9, the HCT116-GFP CloneD2-Cas9 cells are transduced by the MS2RLP particles delivering the chimeric guides D1 (produced with a single or double dose of expression plasmid) or by the vector ILV-GuideD1, at a dose of 10 pg p24/cell, in the presence of 8 µg/mL Polybrene®. A cell defence mechanism inhibitor, BX795 (Invivogen), is used at a concentration of 6 µM in the case of the MS2 (NC)-RLP 2X particles. The transduction supernatant is removed 4 hours later and replaced with fresh supplemented culture medium. At D14 post-transduction, the cells are recovered and the percentage of cells expressing GFP as well as the fluorescence intensity are quantified by cytometry (Macs Quant VYB®, Miltenyi Biotec).

II. Results

The purpose of this experiment is to compare production of MS2RLP particles delivering guide RNA produced using a single or double quantity of the expression plasmid. Firstly, the results presented in FIG. 11 show that the non-transduced (NT) HCT116 cells are not fluorescent (<0.2% of GFP positive cells), whereas more than 99% of the HCT116-GFP CloneD2 target cells are fluorescent. Less than 9% of the HCT116-GFP CloneD2-Cas9 target cells transduced by the vector ILV-GuideD1 are still fluorescent. When the HCT116-GFP CloneD2-Cas9 target cells are transduced by the MS2RLP-GuideD1Chimeric 2X, a 6% decrease in the number of fluorescent cells is observed for the MS2RLP 2X particles transporting the chimeric guides produced in a single dose of the expression plasmid. This decrease is doubled (13% of HCT116-GFP CloneD2-Cas9 negative target cells) for the MS2RLP 2X particles transporting the chimeric guides produced with a double dose of expression plasmid. It is probable that the double dose of expression plasmid used for production of the MS2RLP 2X particles therefore improves the degree of encapsidation of the guideD1 RNAs, hence better effectiveness in knock-out of the GFP sequence.

EXAMPLE 4: EFFECTIVENESS OF AN MS2RLP PARTICLE IN DELIVERING THE CRISPR/CAS9 SYSTEM (GUIDE RNA+RNA CODING CAS9) IN HCT116-GFP CELLS

I. Material & Methods

1. Plasmid Construction 1.1 Plasmids for producing MS2 (NC)-RLP 12X 2X lentiviral particles according to the invention Expression Plasmid for a Sequence of Interest:

The expression plasmids of which the expression cassette is described in Example 1 (FIG. 1, pcDNA-EF1-Cas9-MS2

12X) and in example 2 (FIG. 8, pcDNA-H1-GuideD1 Chimeric-MS2 2X) were used for co-encapsidating, in the same MS2RLP12X-2X particle, both the RNA coding Cas9 and the guide RNA targeting the sequence of the GFP integrated into the genome of the target cells (HCT116-GFP CloneD2).

Encapsidation Plasmid:

The lentiviral particle was modified to contain the sequence of the "Coat" protein of the MS2 bacteriophage in the nucleocapsid protein, in place of the second Zn finger domain. The p8.74 encapsidation plasmid bearing the genes coding the structural and functional proteins (Gag, Pol) used for production of the MS2RLP 12X-2X particles is modified in accordance with the strategy illustrated in FIG. 2a: this p8.74 plasmid is used for generating, by assembly PCR, a plasmid lacking the second zinc finger of the p8.74ΔZF nucleocapsid protein. The second zinc finger is substituted by the "Coat" protein of the MS2 bacteriophage by HpaI cloning, to generate the plasmid p8.74ΔZF-MS2-Coat. This gives the construct illustrated in FIG. 2b. The Pol coding sequence may be deleted or mutated in certain functional elements such as for example the sequence coding reverse transcriptase (RT) or integrase (IN) without altering the function of the MS2RLPs.

Envelope Plasmid (pENV):

This plasmid bears the gene coding an envelope protein, which may be VSV-G coding the envelope protein of the Vesicular stomatitis virus (FIG. 3).

These plasmids are used for producing MS2(NC)-RLP 12X and 2X (or MS2RLP 12X 2X) lentiviral particles according to the invention. More particularly, these plasmids are used for producing MS2RLP-Cas9 12X—GuideD1Chimeric 2X lentiviral particles.

1.2. Plasmids for Producing ILV-GFP Integrative Lentiviral Vectors for Generating the HCT116-GFP Clone D2 Target Cells These plasmids are prepared by a method identical to that in Example 1.

2. Production of Batches of Lentiviral Particles and Lentiviral Vectors

After transfection of the plasmids on producer cells, the supernatants are harvested and used crude or concentrated/purified according to one of the aforementioned methods P1 or P2, described in application WO 2013/014537.

2.1 Production of the Lentiviral Particles

Production is carried out in a 10-stack CellISTACK (6360 cm$^2$, Corning) with HEK293T producer cells (ATCC, CRL-11268), cultured in Dulbecco's Modified Eagle's Medium (DMEM, Gibco, Paisley, UK) supplemented with 1% penicillin/streptomycin and 1% of ultraglutamine (PAA) at 37° C. in a humid atmosphere at 5% $CO_2$.

The MS2 (NC)-RLP 12X-2X particles are produced by transfection of the following four plasmids:

The two expression plasmids described above, of which the pcDNA-H1-GuideD1 Chimeric-MS2 2X plasmid (FIG. 8) is used in double the quantity of the pcDNA-EF1-Cas9-MS212X plasmid;
p8.74ΔZF-MS2-Coat;
pENV bearing the envelope VSV-G.

More particularly, the MS2RLP-Cas9 12X-GuideD1Chimeric 2X lentiviral particles are produced by transfection of the following four plasmids:

The two expression plasmids described above, of which the plasmid pcDNA-H1-GuideD1Chimeric-MS2 2X (the expression cassette of which is illustrated in FIG. 8) is used in double the quantity of the plasmid pcDNA-EF1-Cas9-MS212X (the expression cassette of which is illustrated in FIG. 1);

p8.74ΔZF-MS2-Coat (the expression cassette of which is illustrated in FIG. 2b);
pENV bearing the envelope VSV-G (the expression cassette of which is illustrated in FIG. 3).

24 hours after standard transfection with calcium phosphate, the culture supernatant is replaced with fresh unsupplemented DMEM medium. The producer cells are incubated at 37° C./5% $CO_2$. After changing the medium, the supernatant is harvested four times (32 h, 48 h, 56 h and 72 h post-transfection). Each collection is clarified by 5 min centrifugation at 3000 g before being microfiltered on a 0.45 μm filter (Stericup®, Millipore). All the collections are then pooled to compose the crude supernatant.

This production therefore comprises two expression plasmids, an encapsidation plasmid and an envelope plasmid. The proportion of plasmids used is:

33% of the expression plasmid coding the guide,
17% of the expression plasmid coding Cas9 (the quantity of expression plasmid coding the guide is doubled with respect to that of the expression plasmid coding Cas9),
25% of the p8.74ΔZF plasmid, and
25% of the pENV plasmid.

The ILV-GFP lentiviral vectors are produced as described in Example 1.

2.2 Concentration and Purification of the Lentiviral Particles and Lentiviral Vectors The particles and the vectors are concentrated and purified according to method P1 described in Example 1.

3. Titration of the Physical Particles by ELISA p24 Assay

The p24 capsid protein is detected directly on the viral supernatant using, and following the recommendations of, the HIV-1 p24 ELISA kit (Perkin Elmer). The p24 protein captured is complexed with a biotinylated polyclonal antibody, and then detected by a streptavidin conjugated with horseradish peroxidase (HRP). The resultant complex is detected by spectrophotometry after incubation with the ortho-phenylenediamine-HCl substrate (OPD) producing a yellow coloration that is directly proportional to the quantity of p24 protein captured. The absorbance of each well is quantified on the Synergy H1 Hybrid® plate reader (Biotek) and calibrated against the absorbance of a standard range of p24 protein. The viral titre expressed as physical particles per ml is calculated from the concentration of p24 protein obtained, knowing that 1 μg of p24 protein corresponds to $10^4$ physical particles.

The lentiviral particles and the lentiviral vectors are titrated as described in Example 1.

4. Generation of Target Cells and Transduction by MS2 (NC)-RLP 12X 2X Lentiviral Particles According to the Invention This example aims to show that it is possible to co-encapsidate, in the same MS2RLP 12X-2X particle, both the RNA coding Cas9 and the guide RNA targeting the sequence of the GFP, integrated into the genome of the target cells, and then transfer these different RNAs via the MS2RLP-Cas9 12X-GuideD1Chimeric 2X particles into the target cells, HCT116-GFP doneD2. At the end of this transfer of RNA, the CRISPR/Cas9 system should be functional and generate breaks of double-stranded DNA allowing knock-out of the target gene, and thus transform the GFP+ cells into GFP− cells, using one and the same tool for transfer of the 2 constituents of the CRISPR/Cas9 system.

4.1 HCT116-GFP cloneD2 Target Cells

This clone is prepared by a method identical to that in Example 1.

4.2 Transduction of the HCT116-GFP CloneD2 Target Cells by MS2 (NC)-RLP 12X 2X Lentiviral Particles According to the Invention The HCT116-GFP Clone D2 cells are seeded in a 24-well plate at 25000 cells/cm$^2$ and incubated for 24 h at 37° C./5% $CO_2$. The HCT116-GFP CloneD2 cells are transduced by the MS2RLP 12X-2X particles delivering both Cas9 and the chimeric guide D1, at a dose of 10 pg p24/cell in the presence of 8 μg/mL Polybrene®. A cell defence mechanism inhibitor, BX795 (Invivogen), is used at a concentration of 6 μM in the case of the MS2RLP 12X-2X particles. The transduction supernatant is removed 4 hours later and replaced with fresh supplemented culture medium. A second transduction was carried out under the same conditions (FIG. 20), 6 days after the first transduction. Finally, a third transduction was carried out under the same conditions 12 days after the first transduction (FIG. 12). 14 days after the last transduction, the cells are recovered and the percentage of cells expressing GFP is quantified by cytometry (Macs Quant VYB, Miltenyi Biotec).

II. Results

The purpose of this experiment is to study the possibility of simultaneously transferring RNAs coding Cas9 and guide RNAs via MS2RLP 12X 2X particles by measuring the functionality of the CRISPR/Cas9 system in target cells. Firstly, the results presented in FIG. 12 show that the non-transduced (NT) HCT116 cells are not fluorescent (<0.2% of GFP+ cells), whereas the HCT116-GFP CloneD2 target cells are fluorescent at more than 96%. When the target cells are transduced with the MS2 (NC)-RLP 12X-2X particles delivering the complete CRISPR/Cas9 system, 14 days after the third transduction of the cells, a 38% decrease is noted in the number of fluorescent cells. There is therefore knock-out of the GFP gene of the order of 38% with MS2RLP 12X 2X particles delivering both Cas9 nuclease and the anti-GFP guides. Extinction of the target gene by the CRISPR/Cas9 system is therefore 3 times more effective when the target cells are transduced by a single batch of MS2RLP particles that have been produced by co-transfection of two species of expression plasmids expressing a nuclease and guide RNAs respectively, than when two batches of particles transporting respectively the RNA of the Cas9 nuclease and guide RNAs are added at the moment of transduction (FIG. 12 and FIG. 1). The CRISPR Cas9 system is therefore more efficient with particles transporting the multiple RNAs coding Cas9 and the guide RNAs, respectively.

The results presented in FIG. 20 show that the non-transduced (NT) HCT116 cells are not fluorescent (<0.2% of GFP+ cells), whereas the HCT116-GFP cloneD2 target cells are fluorescent at more than 99%. When the target cells are transduced with the MS2 (NC)-RLP 12X 2X particles delivering the complete CRISPR/Cas9 system, 14 days after the second transduction of the cells, a 57% decrease is noted in the number of fluorescent cells. There is therefore knock-out of the GFP gene of the order of 57% with MS2RLP 12X-2X particles delivering the RNAs coding both for the Cas9 nuclease and the anti-GFP guides. As a reminder, it is found that the percentage of cells expressing the GFP decreases by 12.8% when Cas9 is expressed constitutively and the guide RNA is supplied by the MS2RLP particles (FIG. 11). The percentage of cells expressing the GFP is therefore five times lower when the MS2RLP particles deliver both the RNA coding Cas9 and the guide RNA after two transductions (FIG. 20). Analysis of the cells still expressing GFP after two transductions versus three transductions by the MS2RLP-Cas9 12X-GuideD1Chimeric 2X particles shows that the CRISPR system seems more effective after two transductions (57% effectiveness, FIG. 20) than after three transductions (38% effectiveness, FIG. 12). This difference could be explained by the fact that when the CRISPR system is delivered into the target cell (HCT116-GFP CloneD2), it will generate a break of double-stranded DNA at the level of the target sequence, i.e. the sequence coding the protein GFP, but also on other sequences non-specifically. In fact, the CRISPR system has a certain level of non-specific cleavage, called "off-target effect", allowing the generation of double-stranded DNA breaks that also undergo the DNA repair system (NHEJ system, for Non Homologous End Joining), just like the double-stranded DNA breaks generated specifically. The more the CRISPR system is delivered into the target cell, the more it will display "off-target effects", there will be double-stranded DNA breaks generated in the same target cell. This system reaches a limit for which the NHEJ system becomes saturated, and the DNA is no longer repaired. In this case, non-repair of the genomic DNA induces death of the transduced cell. This is what is observed in the cells transduced 3 times by the MS2RLP-Cas9 12X-GuideD1Chimeric 2X particles. In fact, the cells transduced three times eventually die in the culture flask. Thus, the cells that have not been transduced, and therefore have not been affected by the CRISPR system allowing extinction of the protein GFP, have a proliferative advantage with respect to the cells transduced three times, explaining why the level of cells expressing the GFP is higher after three transductions by the MS2RLP-Cas9 12X-GuideD1Chimeric 2X particles than after two transductions.

In conclusion, these MS2RLP 12X 2X particles mark themselves out as being the best tool for co-delivering the CRISPR/Cas9 system, using just one batch of particles, after one or two transductions, according to the effectiveness of genome editing, and according to the cellular type as well.

EXAMPLE 5: LENTIVIRAL PARTICLES ACCORDING TO THE INVENTION FOR THE TALEN SYSTEM

The use of the TALEN system in a genome editing strategy requires the use of a first TALEN that is fixed upstream of the site of cleavage of the double-stranded DNA generated (TALEN 5'), as well as a second TALEN that is fixed downstream of the site of cleavage of the double-stranded DNA generated (TALEN 3').

FIG. 13a shows the expression plasmid allowing production of MS2RLP 12X particles expressing a TALEN that is fixed upstream (5' side) of the cleavage of double-stranded DNA generated.

FIG. 13b shows the expression plasmid allowing production of MS2RLP 12X particles expressing a TALEN that is fixed downstream (3' side) of the cleavage of double-stranded DNA generated.

FIG. 14a shows the expression plasmid allowing production of integrative particles ILV expressing a TALEN that is fixed upstream (5' side) of the cleavage of double-stranded DNA generated.

FIG. 14b shows the expression plasmid allowing production of integrative particles ILV expressing a TALEN that is fixed downstream (3' side) of the cleavage of double-stranded DNA generated.

EXAMPLE 6: LENTIVIRAL PARTICLES ACCORDING TO THE INVENTION FOR THE ZN FINGER NUCLEASE SYSTEM

Use of the Zn Finger Nuclease system in a genome editing strategy requires the use of a first Zn Finger that is fixed upstream of the site of cleavage of the double-stranded DNA generated (ZFP 5'), as well as a second Zn Finger that is fixed downstream of the site of cleavage of the double-stranded DNA generated (ZFP 3').

FIG. 15a shows the expression plasmid allowing production of MS2RLP 12X particles expressing a Zn Finger that is fixed upstream (5' side) of the cleavage of double-stranded DNA generated.

FIG. 15b shows the expression plasmid allowing production of MS2RLP 12X particles expressing a Zn Finger that is fixed downstream (3' side) of the cleavage of double-stranded DNA generated.

FIG. 16a shows the expression plasmid allowing production of integrative particles ILV expressing a Zn Finger that is fixed upstream (5' side) of the cleavage of double-stranded DNA generated.

FIG. 16b shows the expression plasmid allowing production of integrative particles ILV expressing a Zn Finger that is fixed downstream (3' side) of the cleavage of double-stranded DNA generated.

EXAMPLE 7: CONSTRUCTION OF PP7(IN)-RLP LENTIVIRAL PARTICLES BY MODIFICATION OF INTEGRASE

I. Material & Methods
1. Plasmid Construction
Expression Plasmid for a Sequence of Interest:

The expression plasmid bears an expression cassette (see FIG. 17) with or without an intron sequence or RNA stabilizing sequence. In order to transport the mRNAs into the lentiviral particles, 12 repetitions of the stem-loop motif of the PP7 RNA (ctagaaaggagcagacgatatggcgtcgctccctgcag SEQ ID No.2) were inserted in an expression cassette downstream of the reporter gene (FIG. 17).

The promoter used may be the CMV or EF1 promoter (FIG. 17) but other promoters may be used. The sequence of interest may be a DNA coding a reporter protein such as native Firefly Luciferase (FIG. 17), a green (ZsGreenI), red (mCherry) or blue (mtBFP) fluorescent protein, or a cDNA coding a protein, for example the CRE protein. The sequence of interest may also be that of an shRNA, an miRNA, an sgRNA, an LncRNA or a circRNA.

Encapsidation Plasmid:
The lentiviral particle was modified to contain the sequence of the "Coat" protein of the bacteriophage PP7 in the integrase. The p8.74 encapsidation plasmid bearing the genes coding the structural and functional proteins (Gag, Pol) used for production of the PP7(IN)-RLP particles is modified in accordance with the strategy illustrated in FIG. 18: this p8.74 plasmid is used for generating, by assembly PCR, a plasmid on which the protein Coat of the PP7 phage is fused with the C terminal domain of the integrase. This fusion, obtained by HpaI cloning, makes it possible to generate the P8.74-POL-PP7 Coat plasmid. This gives the construct illustrated in FIG. 19. The Pol coding sequence may be deleted or mutated in certain functional elements such as for example the sequence coding reverse transcriptase (RT).

Envelope Plasmid (pENV):
This plasmid bears the gene coding an envelope protein, which may be VSV-G coding the envelope protein of the Vesicular stomatitis virus (FIG. 3).

2. Production, Concentration/Purification and Titration of the Lentiviral Particles The lentiviral particles are produced as described in Example 1, according to method P1.

3. Luciferase Expression Kinetics

The HCT116 cells (ATCC, CCL-247) are seeded in a 96-well plate and incubated for 24 h at 37° C./5% $CO_2$. Transduction by the PP7(IN)-RLP-Luc 12X particles produced according to method P1 is carried out at a dose of 2.8 µg p24/cell, in the presence of 8 µg/mL Polybrene. The transduction supernatant is removed 4 hours later and replaced with fresh supplemented culture medium. At 4 h, 8 h, 24, 32, and 48 h post-transduction, the cells are recovered and luciferase expression is analysed using the OneGlo Luciferase assay kit (Promega) following the supplier's recommendations and using the Synergy H1 Hybrid plate reader (Biotek). This assay is carried out in triplicate. HCT116 cells that have not been transduced are used as a control.

II. Results

It is possible to transport RNAs into the lentiviral particles with PP7-Coat in integrase. Maximum luciferase expression is reached at 8 h. After 8 h, luciferase activity decreases. The PP7(IN)-RLP particles therefore make it possible to deliver RNAs.

EXAMPLE 8: EFFECTIVENESS OF AN MS2RLP PARTICLE IN DELIVERING THE CRISPR/CAS9 SYSTEM (GUIDE RNA+RNA CODING CAS9) INTO HCT116-GFP CELLS, AS A FUNCTION OF THE PROMOTER ALLOWING TRANSCRIPTION OF THE GUIDE RNA IN THE PRODUCER CELLS

I. Material & Methods
1. Plasmid Construction
1.1 Plasmids for Producing MS2 (NC)-RLP 12X and 2X Lentiviral Particles
Expression Plasmid for a Sequence of Interest:

The expression plasmids described in Example 1 (FIG. 1, pcDNA-EF1-Cas9-MS2 12X) and in FIG. 21, pcDNA-U6-GuideD1 Chimeric-MS2 2X were used for co-encapsidating, in the same MS2RLP 12X-2X particle, both the RNA coding Cas9 and the guide RNA D1 under the control of the U6 promoter, targeting the sequence of the GFP integrated into the genome of the target cells (HCT116-GFP CloneD2).

Encapsidation Plasmid:
The lentiviral particle was modified to contain the sequence of the "Coat" protein of the MS2 bacteriophage in the nucleocapsid protein, in place of the second Zn finger domain. The p8.74 encapsidation plasmid bearing the genes coding the structural and functional proteins (Gag, Pol) used for production of the MS2RLP 12X-2X particles is modified in accordance with the strategy illustrated in FIG. 2a: this p8.74 plasmid is used for generating, by assembly PCR, a plasmid lacking the second zinc finger of the p8.74ΔZF nucleocapsid protein. The second zinc finger is substituted by the "Coat" protein of the MS2 bacteriophage by HpaI cloning, to generate the p8.74ΔZF-MS2-Coat plasmid. This gives the construct illustrated in FIG. 2b. The Pol coding sequence may be deleted or mutated in certain functional elements such as for example the sequence coding reverse transcriptase (RT) or integrase (IN) without altering the function of the MS2RLPs.

Envelope Plasmid (pENV):
This plasmid bears the gene coding an envelope protein, which may be VSV-G coding the envelope protein of the Vesicular stomatitis virus (FIG. 3).

More particularly, these plasmids are used for producing MS2RLP-Cas9 12X-GuideD1Chimeric 2X lentiviral particles.

1.2. Plasmids for Producing ILV-GFP Integrative Lentiviral Vectors for Generating the HCT116-GFP Clone D2 Target Cells These plasmids are prepared by a method identical to that in Example 1.

2. Production of Batches of Lentiviral Particles and Lentiviral Vectors

After transfection of the plasmids on producer cells, the supernatants are harvested and used crude or concentrated/purified according to one of the aforementioned methods P1 or P2, described in application WO 2013/014537.

2.1 Production of the Lentiviral Particles and Lentiviral Vectors

Production is carried out in a 10-stack CellISTACK (6360 cm$^2$, Corning) with HEK293T producer cells (ATCC, CRL-11268), cultured in Dulbecco's Modified Eagle's Medium (DMEM, Gibco, Paisley, UK) supplemented with 1% penicillin/streptomycin and 1% of ultraglutamine (PAA) at 37° C. in a humid atmosphere at 5% $CO_2$.

The MS2 (NC)-RLP 12X 2X particles are produced by transfection of the following four plasmids:

The two expression plasmids described above of which pcCDNA-U6-GuideD1Chimeric-MS2 2X plasmid (the expression cassette of which is illustrated in FIG. 21) is used in double the quantity of the pcDNA-EF1-Cas9-MS2 12X plasmid (the expression cassette of which is illustrated in FIG. 1);
p8.74ΔZF-MS2-Coat;
pENV bearing the envelope VSV-G.

24 hours after standard transfection with calcium phosphate, the culture supernatant is replaced with fresh unsupplemented DMEM medium. The producer cells are incubated at 37° C./5% $CO_2$. After changing the medium, the supernatant is harvested four times (32 h, 48 h, 56 h and 72 h post-transfection). Each collection is clarified by 5 min centrifugation at 3000 g before being microfiltered on a 0.45 µm filter (Stericup®, Millipore). All the collections are then pooled to compose the crude supernatant.

The MS2 (NC)-RLP 12X 2X lentiviral particles are produced as described in Example 4.

The ILV-GFP lentiviral vectors are produced as described in Example 1.

2.2 Concentration and Purification of the Lentiviral Particles

The particles are concentrated and purified according to method P1 described in Example 1.

3. Titration of the Physical Particles by ELISA p24 Assay

The p24 capsid protein is detected directly on the viral supernatant using, and following the recommendations of, the HIV-1 p24 ELISA kit (Perkin Elmer). The p24 protein captured is complexed with a biotinylated polyclonal antibody, and then detected by a streptavidin conjugated with horseradish peroxidase (HRP). The resultant complex is detected by spectrophotometry after incubation with the ortho-phenylenediamine-HCl substrate (OPD) producing a yellow coloration that is directly proportional to the quantity of p24 protein captured. The absorbance of each well is quantified on the Synergy H1 Hybrid® plate reader (Biotek) and calibrated against the absorbance of a standard range of p24 protein. The viral titre expressed as physical particles per ml is calculated from the concentration of p24 protein obtained, knowing that 1 µg of p24 protein corresponds to $10^4$ physical particles.

The lentiviral particles and the lentiviral vectors are titrated as described in Example 1.

4. Generation of Target Cells and Transduction by MS2 (NC)-RLP 12X 2X Lentiviral Particles According to the Invention This example aims to show that it is possible to co-encapsidate, in the same MS2RLP 12X-2X particle, both the RNA coding Cas9 and the guideD1 RNAs targeting the sequence of the GFP integrated into the genome of the target cells, and then transfer these different RNAs via the MS2 (NC)-RLP 12X-2X particles into the target cells, HCT116-GFP cloneD2. At the end of this transfer of RNA, the CRISPR/Cas9 system should be functional and generate breaks of double-stranded DNA allowing knock-out of the target gene, and thus transform the GFP+ cells into GFP− cells, using one and the same tool for transfer of the 2 constituents of the CRISPR/Cas9 system.

4.1 HCT116-GFP cloneD2 Target Cells

This done is prepared by a method identical to that in Example 1.

4.2 Transduction of the HCT116-GFP CloneD2 Target Cells by MS2 (NC)-RLP 12X 2X Lentiviral Particles According to the Invention The HCT116-GFP Clone D2 cells are seeded in a 24-well plate at 25000 cells/cm$^2$ and incubated for 24 h at 37° C./5% $CO_2$. The HCT116-GFP CloneD2 cells are transduced by the MS2RLP 12X 2X particles delivering both Cas9 and the guide D1, at a dose of 10 pg p24/cell, in the presence of 8 µg/mL Polybrene®. A cell defence mechanism inhibitor, BX795 (Invivogen), is used at a concentration of 6 µM in the case of the MS2RLP 12X 2X particles. The transduction supernatant is removed 4 hours later and replaced with fresh supplemented culture medium. At D14 post-transduction, the cells are recovered and the percentage of cells expressing GFP is quantified by cytometry (Macs Quant VYB, Miltenyi Biotec).

II. Results

The purpose of this experiment is to evaluate the effect of the promoter allowing expression of the guide RNA for generating MS2RLP particles simultaneously delivering RNAs coding Cas9 and guide RNAs.

In this example, two promoters are tested: H1 and U6.

Firstly, the results presented in FIG. 22 show that the non-transduced (NT) HCT116 cells are not fluorescent (<0.1% of GFP+ cells), whereas the HCT116-GFP doneD2 target cells are fluorescent at more than 99%. When the target cells are transduced with the MS2 (NC)-RLP 12X 2X particles delivering the complete CRISPR/Cas9 system, 14 days after the second transduction of the cells, a decrease is noted in the number of fluorescent cells of 46.2% in the case of the particles generated starting from the plasmid bearing the H1 promoter, and 81.9% in the case of the particles generated starting from the plasmid bearing the U6 promoter. Thus, the strongest knock-out of the GFP gene of the order of 81.9% is observed with MS2RLP 12X 2X particles generated starting from the plasmid bearing the U6 promoter after two transductions. The percentage of cells expressing the GFP is therefore almost 2 times lower when the particles are generated starting from the plasmid bearing the U6 promoter than when the particles are generated starting from the plasmid bearing the H1 promoter. In conclusion, the nature of the promoter used for generating the guide RNAs to be encapsidated in the MS2RLP particles has an impact on the effectiveness of the MS2RLP particle delivering the CRISPR/Cas9 system.

EXAMPLE 9: EFFECTIVENESS OF AN MS2RLP PARTICLE IN DELIVERING THE CRISPR/CAS9 SYSTEM (GUIDE RNA+RNA CODING CAS9) INTO ACTIVATED PRIMARY T LYMPHOCYTES, FOR KNOCK-OUT OF THE PD1 GENE

I. Material & Methods

1. Plasmid Construction 1.1 Plasmids for Producing MS2 (NC)-RLP 12X 2X Lentiviral Particles According to the Invention Expression Plasmid for a Sequence of Interest:

The expression plasmid described in Example 1 (the expression cassette of which is illustrated in FIG. 1, pcDNA-EF1-Cas9-MS2 12X) and the expression plasmid of which the expression cassette is illustrated in FIG. 23, pcDNA-U6-Guide_antiPD1Chimeric-MS2 2X were used for co-encapsidating, in the same MS2RLP 12X-2X particle, both the RNA coding Cas9 and the guide RNA under the control of the U6 promoter, targeting the sequence of the PD1 gene integrated into the genome of the primary T lymphocytes.

Encapsidation Plasmid:

The lentiviral particle was modified to contain the sequence of the "Coat" protein of the MS2 bacteriophage in the nucleocapsid protein, in place of the second Zn finger domain. The p8.74 encapsidation plasmid bearing the genes coding the structural and functional proteins (Gag, Pol) used for production of the MS2RLP 12X-2X particles is modified in accordance with the strategy illustrated in FIG. 2a: this p8.74 plasmid is used for generating, by assembly PCR, a plasmid lacking the second zinc finger of the p8.74ΔZF nucleocapsid protein. The second zinc finger is substituted by the "Coat" protein of the MS2 bacteriophage by HpaI cloning, to generate the p8.74ΔZF-MS2-Coat plasmid. This gives the construct illustrated in FIG. 2b. The Pol coding sequence may be deleted or mutated in certain functional elements such as for example the sequence coding reverse transcriptase (RT) or integrase (IN) without altering the function of the MS2RLPs.

Envelope Plasmid (pENV):

This plasmid bears the gene coding an envelope protein, which may be VSV-G coding the envelope protein of the Vesicular stomatitis virus (FIG. 3).

These plasmids are used for producing MS2 (NC)-RLP 12X 2X lentiviral particles according to the invention. More particularly, these plasmids are used for producing MS2RLP-Cas9 12X-GuideantiPD1 Chimeric 2X lentiviral particles.

1.2 Plasmids for Producing Control MS2-(NC)-RLP 12X Lentiviral Particles According to the Invention These plasmids are prepared by a method identical to that in Example 1. More particularly, these plasmids are used for producing MS2RLP-Cas9 12X lentiviral particles, as described in paragraph 1.1 of Example 1.

1.3 Plasmids for producing control ILVCas9+GuideantiPD1 integrative lentiviral vectors Expression Plasmid for a Sequence of Interest:

The expression plasmids bear an expression cassette as described in FIG. 4 and an expression cassette as described in FIG. 32. These plasmids may contain other elements such as the native sequence WPRE (Woodchuck Hepatitis Virus Posttranscriptional Regulatory Element) or the cPPT/CTS sequence. Viral pathogenicity is eliminated by substitution of regions of the viral genome required for retroviral replication by the transgene. For the first plasmid, the promoter used is the EF1 promoter, but other promoters may be used. The plasmid sequence of interest is a DNA coding the RNA of the Cas9 protein (FIG. 4), in its wild-type form (WT) or in its mutated form (N).

For the second plasmid, the promoters used are U6 or H1, but other promoters may be used. The sequence of interest is an antiPD1 guide (FIG. 32).

Encapsidation Plasmid:

The p8.74 encapsidation plasmid bearing the genes coding the structural and functional proteins (Gag, Pol) is used for production of the integrative lentiviral vectors (FIG. 6).

Envelope Plasmid (pENV):

This plasmid is identical to the envelope plasmid used for producing MS2RLP lentiviral particles (FIG. 3).

2. Production of Batches of Lentiviral Particles and Lentiviral Vectors After transfection of the plasmids on cells, the supernatants are harvested and used crude or concentrated/purified according to one of the aforementioned methods P1 or P2, described in application WO 2013/014537.

2.1 Production of the Lentiviral Particles and Lentiviral Vectors

Production is carried out in a 10-stack CellSTACK (6360 $cm^2$, Corning) with HEK293T producer cells (ATCC, CRL-11268), cultured in Dulbecco's Modified Eagle's Medium (DMEM, Gibco, Paisley, UK) supplemented with 1% penicillin/streptomycin and 1% of ultraglutamine (PAA) at 37° C. in a humid atmosphere at 5% $CO_2$.

The MS2 (NC)-RLP 12X 2X particles are produced by transfection of the following four plasmids:

The two expression plasmids described above of which
  pcDNA-U6-Guide_antiPD1 Chimeric-MS2 2X plasmid (the expression cassette of which is illustrated in FIG. 23) is used in double the quantity of the pcDNA-EF1-Cas9-MS2 12X plasmid (the expression cassette of which is illustrated in FIG. 1);
p8.74ΔZF-MS2-Coat;
pENV bearing the envelope VSV-G.

The MS2 (NC)-RLP 12X 2X particles are produced by the method described in Example 4.

More particularly, these plasmids are used for producing the MS2RLP-Cas9 12X-GuideantiPD1 Chimeric 2X lentiviral particles.

24 hours after standard transfection with calcium phosphate, the culture supernatant is replaced with fresh unsupplemented DMEM medium. The producer cells are incubated at 37° C./5% $CO_2$. After changing the medium, the supernatant is harvested four times (32 h, 48 h, 56 h and 72 h post-transfection). Each collection is clarified by 5 min centrifugation at 3000 g before being microfiltered on a 0.45 µm filter (Stericup®, Millipore). All the collections are then pooled to compose the crude supernatant.

The control MS2 (NC)-RLP 12X lentiviral particles are produced as described in Example 4.

Production, purification and titration of the control lentiviral vectors ILV, expressing the CRISPR/Cas9 system (guide RNA+Cas9), are carried out under the same conditions as in Example 1, according to method P2.

2.2 Concentration and Purification of the Lentiviral Particles

The particles are concentrated and purified according to method P2 described in Example 1.

3. Titration of the Physical Particles by ELISA p24 Assay

The p24 capsid protein is detected directly on the viral supernatant using, and following the recommendations of, the HIV-1 p24 ELISA kit (Perkin Elmer). The p24 protein captured is complexed with a biotinylated polydonal antibody, and then detected by a streptavidin conjugated with horseradish peroxidase (HRP). The resultant complex is detected by spectrophotometry after incubation with the ortho-phenylenediamine-HCl substrate (OPD) producing a yellow coloration that is directly proportional to the quantity of p24 protein captured. The absorbance of each well is quantified on the Synergy H1 Hybrid® plate reader (Biotek) and calibrated against the absorbance of a standard range of p24 protein. The viral titre expressed as physical particles per ml is calculated from the concentration of p24 protein obtained, knowing that 1 µg of p24 protein corresponds to $10^4$ physical particles.

The lentiviral particles and the lentiviral vectors are titrated as described in Example 1.

4. Preparation of the Target Cells and Transduction by MS2 (NC)-RLP 12X 2X Lentiviral Particles According to the Invention This example aims to show that it is possible to co-encapsidate, in the same MS2RLP 12X 2X particle, both the RNA coding Cas9 and the guide RNA targeting the sequence of the PD1 gene, and then transfer these different RNAs via the MS2 (NC)-RLP 12X 2X particles into the target cells, the activated primary T lymphocytes. At the end of this transfer of RNA, the CRISPR/Cas9 system should be functional and generate breaks of double-stranded DNA allowing knock-out of the target PD1 gene using one and the same tool for transfer of the 2 constituents of the CRISPR/Cas9 system.

4.1 Preparation of the Target Cells, Activated Primary T Lymphocytes

The target cells, the T lymphocytes, are prepared from a peripheral blood sample. The mononuclear cells from the peripheral blood are isolated by Ficoll gradient centrifugation, and then undergo adherence for 2 hours at 37° C./5% $CO_2$ in a T75 flask. The cells in suspension are recovered, and the T lymphocytes are purified by negative selection using magnetic beads (Pan T cell isolation kit, Miltenyi Biotec). The purified T lymphocytes are activated for 24 hours (Dynabeads® Human T-Activator CD3/CD28, ThermoFisher) at 37° C./5% $CO_2$.

4.2 Transduction of the Target Cells, Activated Primary T Lymphocytes

The target cells, activated primary T lymphocytes, are seeded in a 96-well plate at 1 000 000 cells/mL and transduced by the MS2RLP 12X 2X particles delivering both Cas9 and the guide, or by the MS2RLP 12X particles delivering only Cas9 (negative control), in the presence of 8 µg/mL Polybrene®, at different doses (0.1; 0.5; 1 or 5 pg p24/cell), or by the ILV particles delivering both Cas9 and the guide (positive control), at different doses (MOI 5, 10, 25, 50). A cell defence mechanism inhibitor, BX795 (Invivogen), is used at a concentration of 6 µM in the case of the MS2RLP 12X 2X and MS2RLP 12X particles.

The transduction supernatant is removed 4 hours later and replaced with fresh supplemented culture medium. 48 hours later, a second transduction is carried out under the same conditions as the first. Four days after the second transduction, the cells are recovered and the percentage of cells expressing PD1 is quantified by cytometry (Macs Quant VYB, Miltenyi Biotec) after immunolabelling of the cells with the antiPD1 antibody (Miltenyi Biotec).

Viability is analysed by adding Viobility™ Fixable Dyes (Miltenyi Biotec) just before FACS analysis of the cells, and the phenotyping of the lymphocytes is carried out by immunolabelling of the cells with the anti-TCR and antiCD25 antibodies (Miltenyi Biotec).

II. Results

The purpose of this experiment is to evaluate the effectiveness of the CRISPR/Cas9 system delivered by the MS2RLP particles for knock-out of an endogenous gene of primary cells, for example the PD1 gene in activated primary T lymphocytes (FIG. 24).

The PD1 gene receives particular attention in the tumoral context since extinction of expression of PD1 allows recognition of tumour cells by the immune system.

When the cells are transduced with the MS2 (NC)-RLP 12X 2X particles delivering the complete CRISPR/Cas9 system, four days after the second transduction, a decrease is noted in the number of cells expressing the protein PD1 of 31% in the case of the first dose (0.1 pg p24/cell), 60% in the case of the second dose (0.5 pg p24/cell), 75% in the case of the third dose (1 pg p24/cell) and 86% in the case of the fourth dose (5 pg p24/cell). In parallel, MS2RLP expressing only Cas9 is used as negative control of knock-out of the PD1 gene. The results show that the percentage of cells expressing the PD1 protein is stable, whatever the dose of MS2RLP 12X 2X particles delivering the CRISPR/Cas9 system used.

FIG. 25 shows the effectiveness of the ILV particle in delivering the CRISPR/Cas9 system for knock-out of the PD1 gene under conditions comparable to those used for delivering the CRISPR/Cas9 system using the MS2RLP 12X 2X particles. At the highest MOI used (MOI 50), 42% of the cells express the PD1 gene whereas at the highest dose of MS2RLP (5 pg p24/cell), there only remain 14% of cells expressing the PD1 gene. The MS2RLP particle is therefore the best tool for delivering the CRISPR/Cas9 system and allowing effective knock-out of an endogenous target.

FIGS. 24 and 25 were obtained from transduction of activated human T lymphocytes, which are primary cells, and are therefore sensitive and delicate for any manipulation. FIG. 26 illustrates measurement of the viability of the T lymphocytes, after the first and the second transduction with the MS2RLP 12X-2X particles delivering the CRISPR/Cas9 system. FIG. 26 allows determination of the optimum dose of MS2RLP 12X 2X particles delivering the CRISPR/Cas9 system, corresponding to 1 pg p24/cell, in order to obtain effective knock-out of the PD1 gene (FIG. 24, 75% knock-out of the PD1 gene) without affecting the viability of the activated T lymphocytes.

FIG. 27 illustrates analysis of the phenotype of the T lymphocytes, after the second transduction with the MS2RLP 12X-2X particles delivering the CRISPR/Cas9 system, by measuring the expression of the TCR and the CD25 activation marker. The results show that the percentage of cells expressing TCR and CD25 is stable, whatever the dose of MS2RLP particles used.

In conclusion, FIGS. 24, 26 and 27 show that the MS2RLP particles are the best tool for delivering the CRISPR/Cas9 system (guide RNA+RNA coding Cas9) while preserving the viability and the phenotype of the T lymphocytes transduced.

EXAMPLE 10: EFFECTIVENESS OF AN MS2RLP PARTICLE IN DELIVERING THE CRISPR/CAS9 SYSTEM (GUIDE RNA+RNA CODING CAS9) INTO ACTIVATED PRIMARY T LYMPHOCYTES, FOR KNOCK-OUT OF THE CXCR4 GENE

I. Material & Methods
1. Plasmid Construction
1.1 Plasmids for Producing MS2 (NC)-RLP 12X 2X Lentiviral Particles According to the Invention Expression Plasmid for a Sequence of Interest:
The expression plasmids described in Example 1 (the expression cassette of which is illustrated in FIG. 1, pcDNA- EF1-Cas9-MS2 12X) and in FIG. 28, pcDNA-U6-Guide_antiCXCR4Chimeric-MS2 2X, were used for co-encapsidating, in the same MS2RLP 12X 2X particle, both the RNA coding Cas9 and the guide RNA under the control of the U6 promoter, targeting the sequence of the CXCR4 gene integrated into the genome of the primary T lymphocytes.

Encapsidation Plasmid:

The lentiviral particle was modified to contain the sequence of the "Coat" protein of the MS2 bacteriophage in the nucleocapsid protein, in place of the second Zn finger domain. The p8.74 encapsidation plasmid bearing the genes coding the structural and functional proteins (Gag, Pol) used for production of the MS2RLP 12X-2X particles is modified in accordance with the strategy Illustrated in FIG. 2a: this p8.74 plasmid is used for generating, by assembly PCR, a plasmid lacking the second zinc finger of the p8.74ΔZF nucleocapsid protein. The second zinc finger is substituted by the "Coat" protein of the MS2 bacteriophage by HpaI cloning, to generate the p8.74ΔZF-MS2-Coat plasmid. This gives the construct illustrated in FIG. 2b. The Pol coding sequence may be deleted or mutated in certain functional elements such as for example the sequence coding reverse transcriptase (RT) or integrase (IN) without altering the function of the MS2RLPs.

Envelope Plasmid (pENV):

This plasmid bears the gene coding an envelope protein, which may be VSV-G coding the envelope protein of the Vesicular stomatitis virus (FIG. 3).

These plasmids are used for producing MS2 (NC)-RLP 12X 2X lentiviral particles according to the invention. More particularly, these plasmids are used for producing MS2RLP-Cas9 12X-GuideantiCXCR4Chimeric 2X lentiviral particles.

1.2 Plasmids for Producing Control MS2-(NC)-RLP 12X Lentiviral Particles According to the Invention These plasmids are prepared by a method identical to that in Example 1. More particularly, these plasmids are used for producing MS2RLP-Cas9 12X lentiviral particles, as described in paragraph 1.1 of Example 1.

2. Production of the Batches of Lentiviral Particles

After transfection of the plasmids on producer cells, the supernatants are harvested and used crude or concentrated/purified according to one of the aforementioned methods P1 or P2, described in application WO 20131014537.

2.1 Production of the Lentiviral Articles

Production is carried out in a 10-stack CellSTACK (6360 cm², Corning) with HEK293T producer cells (ATCC, CRL-11268), cultured in Dulbecco's Modified Eagle's Medium (DMEM, Gibco, Paisley, UK) supplemented with 1% penicillin/streptomycin and 1% of ultraglutamine (PAA) at 37° C. in a humid atmosphere at 5% $CO_2$.

The MS2 (NC)-RLP 12X-2X particles are produced by transfection of the following four plasmids:

The two expression plasmids described above of which pcDNA-U6-Guide_antiCXCR4Chimeric-MS2 2X plasmid (the expression cassette of which is illustrated in FIG. 28) is used in double the quantity of the pcDNA-EF1-Cas9-MS2 12X plasmid (the expression cassette of which is illustrated in FIG. 1);

p8.74ΔZF-MS2-Coat;

pENV bearing the envelope VSV-G.

The proportion of plasmids used is identical to that in Example 4.

More particularly, these plasmids are used for producing the MS2RLP-Cas9 12X-GuideantiCXCR4Chimeric 2X lentiviral particles.

24 hours after standard transfection with calcium phosphate, the culture supernatant is replaced with fresh unsupplemented DMEM medium. The producer cells are incubated at 37° C./5% $CO_2$. After changing the medium, the supernatant is harvested four times (32 h, 48 h, 56 h and 72 h post-transfection). Each collection is clarified by 5 min centrifugation at 3000 g before being microfiltered on a 0.45 μm filter (Stencup®, Millipore). All the collections are then pooled to compose the crude supernatant.

The control MS2-(NC)RLP 12X lentiviral particles are produced as described in Example 1.

2.2 Concentration and Purification of the Lentiviral Particles

The particles are concentrated and purified according to method P2 described in Example 1.

3. Titration of the Physical Particles by ELISA p24 Assay

The p24 capsid protein is detected directly on the viral supernatant using, and following the recommendations of, the HIV-1 p24 ELISA kit (Perkin Elmer). The p24 protein captured is complexed with a biotinylated polydonal antibody, and then detected by a streptavidin conjugated with horseradish peroxidase (HRP). The resultant complex is detected by spectrophotometry after incubation with the ortho-phenylenediamine-HCl substrate (OPD) producing a yellow coloration that is directly proportional to the quantity of p24 protein captured. The absorbance of each well is quantified on the Synergy H1 Hybrid® plate reader (Biotek) and calibrated against the absorbance of a standard range of p24 protein. The viral titre expressed as physical particles per ml is calculated from the concentration of p24 protein obtained, knowing that 1 μg of p24 protein corresponds to $10^4$ physical particles.

4. Preparation of the Target Cells and Transduction by MS2 (NC)-RLP 12X 2X Lentiviral Particles According to the Invention This example aims to show that it is possible to co-encapsidate, in the same MS2RLP 12X-2X particle, both the RNA coding Cas9 and the guide RNA targeting the sequence of the CXCR4 gene, and then transfer these different RNAs via the MS2 (NC)-RLP 12X-2X particles into the target cells, activated primary T lymphocytes. At the end of this transfer of RNA, the CRISPR/Cas9 system should be functional and generate breaks of double-stranded DNA allowing knock-out of the target CXCR4 gene using one and the same tool for transfer of the 2 constituents of the CRISPR/Cas9 system.

4.1 Preparation of the Target Cells, Activated Primary T Lymphocytes

The T lymphocyte target cells are prepared from a peripheral blood sample. The mononuclear cells of the peripheral blood are isolated by Ficoll gradient centrifugation, and then undergo adherence for 2 hours at 37° C./5% $CO_2$ in a T75 flask. The cells in suspension are recovered, and the T lymphocytes are purified by negative selection using magnetic beads (Pan T cell isolation kit, Miltenyi Biotec). The purified T lymphocytes are activated for 24 hours (Dynabeads® Human T-Activator CD3/CD28, ThermoFisher) at 37° C./5% $CO_2$.

4.2 Transduction of the Target Cells. Activated Primary T Lymphocytes

The target cells, activated primary T lymphocytes, are seeded in a 96-well plate at 1 000 000 cells/mL and transduced by the MS2RLP 12X 2X particles delivering both Cas9 and the guide, or by the MS2RLP 12X particles delivering only Cas9 (negative control), in the presence of 8 μg/mL Polybrene®, at different doses (0.1; 0.5; 1 or 5 pg p24/cell). A cell defence mechanism inhibitor, BX795 (Invivogen), is used at a concentration of 6 µM in the case of the MS2RLP 12X 2X and MS2RLP 12X particles.

The transduction supernatant is removed 4 hours later and replaced with fresh supplemented culture medium. 48 hours later, a second transduction is carried out under the same conditions as the first. Four days after the second transduction, the cells are recovered and the percentage of cells expressing CXCR4 is quantified by cytometry (Macs Quant VYB, Miltenyi Biotec) after immunolabelling of the cells with the antiCXCR4 antibody (Miltenyi Biotec).

Viability is analysed by adding Viobility™ Fixable Dyes (Miltenyi Biotec) just before FACS analysis of the cells, and phenotyping of the lymphocytes is carried out by immunolabelling of the cells with the anti-TCR and antiCD25 antibodies (Miltenyi Biotec).

II. Results

The purpose of this experiment is to evaluate the effectiveness of the CRISPR/Cas9 system delivered by the MS2RLP particles for knock-out of an endogenous gene of primary cells, for example the CXCR4 gene in activated primary T lymphocytes (FIG. 29).

The CXCR4 gene is a target of interest since extinction of its expression in CD4+ T lymphocytes allows blocking of infection by the HIV-1 virus.

When the cells are transduced with the MS2 (NC)-RLP 12X 2X particles delivering the complete CRISPR/Cas9 system, four days after the second transduction, a decrease is noted in the number of cells expressing the CXCR4 protein of 92% in the case of the first dose (0.1 pg p24/cell), 97% in the case of the second dose (0.5 pg p24/cell), 98% in the case of the third dose (1 µg p24/cell) and 99% in the case of the fourth dose (5 pg p24/cell).

In parallel, MS2RLP expressing only Cas9 is used as negative control of knock-out of the CXCR4 gene. The results show that the percentage of cells expressing the CXCR4 protein is stable, whatever the dose of MS2RLP 12X particles delivering only the Cas9 protein.

FIGS. 30 and 31 were obtained from transduction of activated human T lymphocytes, which are primary cells, and are therefore sensitive and delicate for any manipulation. FIG. 30 illustrates measurement of the viability of the T lymphocytes, after the first and the second transduction with the MS2RLP 12X-2X particles delivering the CRISPR/Cas9 system. It is observed that the viability of the T lymphocytes is not altered by the transduction(s) with the MS2RLP 12X 2X particles, whatever the dose used.

The optimum dose of MS2RLP 12X 2X particles delivering the CRISPR/Cas9 system corresponds to 5 pg p24/cell, and makes it possible to obtain effective knock-out of the CXCR4 gene (FIG. 29, 99% knock-out of the CXCR4 gene) without affecting the viability of the activated T lymphocytes.

FIG. 31 illustrates analysis of the phenotype of the T lymphocytes, after the second transduction with the MS2RLP 12X 2X particles delivering the CRISPR/Cas9 system for knock-out of the CXCR4 gene, by measuring the expression of the TCR and the CD25 activation marker. The results show that the percentage of cells expressing TCR and CD25 is stable, whatever the dose of MS2RLP particles used.

In conclusion, FIGS. 29, 30 and 31 show that the MS2RLP particles are the best tool for delivering the CRISPR/Cas9 system (guide RNA+RNA coding Cas9) while preserving the viability and the phenotype of the T lymphocytes transduced.

EXAMPLE 11: DOSE EFFECT OF AN MS2RLP PARTICLE DELIVERING THE CRISPR/CAS9 SYSTEM (GUIDE RNA+RNA CODING CAS91 IN HCT116-GFP CELLS

I. Material & Methods
1. Plasmid Construction
1.1 Plasmids for Producing MS2 (NC)-RLP 12X 2X Lentiviral Particles According to the Invention These plasmids are prepared by a method identical to that in Example 8. More particularly, these plasmids are used for producing MS2RLP-Cas9 12X-GuideD1Chimeric 2X lentiviral particles.

1.2 Plasmids for Producing ILV-GFP Integrative Lentiviral Vectors for Generating the HCT116-GFP Clone D2 Target Cells These plasmids are prepared by a method identical to that in Example 1.

2. Production of Batches of Lentiviral Particles and Lentiviral Vectors

After transfection of the plasmids on producer cells, the supernatants are harvested and used crude or concentrated/purified according to one of the aforementioned methods P1 or P2 as described in application WO 2013/014537.

2.1 Production of the Lentiviral Particles and Lentiviral Vectors

The MS2RLP 12X 2X lentiviral particles are produced by the method described in Example 4.

The ILV-GFP lentiviral vectors are produced as described in Example 1.

2.2 Concentration and Purification of the Lentiviral Particles and Lentiviral Vectors The lentiviral particles and the lentiviral vectors are concentrated and purified according to method P1 described in Example 1.

3. Titration of the Batches of Lentiviral Particles and Lentiviral Vectors

The lentiviral particles and the lentiviral vectors are titrated by the method described in Example 1.

4. Generation of Target Cells and Transduction by MS2 (NC)-RLP 12X 2X Lentiviral Particles According to the Invention This example aims to show that an MS2RLP 12X 2X particle delivering the CRISPR Cas9 system in target cells has a dose effect on the effectiveness of genome editing. At the end of this transfer of RNA, the CRISPR/Cas9 system should be functional and generate breaks of double-stranded DNA allowing knock-out of the target gene, and thus transform the GFP+ cells into GFP− cells, using one and the same tool for transfer of the 2 constituents of the CRISPR/Cas9 system.

4.1 HCT116-GFP cloneD2 Target Cells

This done is prepared by a method identical to that in Example 1.

4.2 Transduction of the HCT116-GFP CloneD2 Target Cells by the MS2 (NC)-RLP 12X 2X Lentiviral Particles According to the Invention The HCT116-GFP CloneD2 target cells are seeded in a 24-well plate at 25000 cells/cm$^2$ and incubated for 24 h at 37° C./5% $CO_2$. The HCT116-GFP CloneD2 target cells are transduced by the MS2RLP-Cas9 12X-GuideD1Chimeric 2X particles, delivering both Cas9 and the chimeric guide D1, at different doses (0.5; 1; 5 or 10 pg p24/cell) in the presence of 8 µg/mL Polybrene®. A cell defence mechanism inhibitor, BX795 (Invivogen), is used at a concentration of 6 µM in the case of the MS2RLP 12X 2X particles. The transduction supernatant is removed 5 hours later and replaced with fresh supplemented culture medium. A second transduction was carried out under the same conditions 6 days after the first transduction (FIG. 33). 7 days after the last transduction, the cells are recovered and the percentage of cells expressing GFP is quantified by cytometry (Macs Quant VYB, Miltenyi Biotec).

II. Results

The purpose of this experiment is to study the ability of the MS2RLP 12X 2X particles according to the invention to induce a dose effect on genome editing, by simultaneously transferring RNAs coding Cas9 and guide RNAs at various concentrations and measuring the extinction of the GFP in HCT116-GFP CloneD2's, with a first transduction (FIG. 33, % of T1 positive cells) and a second transduction (FIG. 33, % of T2 positive cells).

Firstly, the results presented in FIG. 33 show that the HCT116-GFP CloneD2 target cells are 100% fluorescent whereas the non-transduced (NT) HCT116 cells are not fluorescent. When the cells are transduced with the MS2RLP 12X 2X particles delivering the complete CRISPR/Cas9 system, 7 days after the second transduction of the cells (FIG. 33, % of T2 positive cells), a decrease is noted in the number of fluorescent cells following a dose effect. Stronger extinction of the GFP is observed after the second transduction than after the first transduction whatever the dose of pg p24/cell (0.5, 1, 5 or 10).

After the second transduction, there is knock-out of the GFP gene of the order of 33% for a dose of 0.5 pg p24/cell, knock-out of the GFP gene of the order of 39% for 1 pg p24/cell, knock-out of the GFP gene of the order of 58% for 5 pg p24/cell and finally knock-out of the GFP gene of the order of 65% at 10 µg p24/cell. A second transduction therefore allows the effectiveness of knock-out of the GFP to be increased with respect to the first transduction. The higher the dose of MS2RLP 12X 2X particles, the greater the knock-out of the GFP.

EXAMPLE 12: EFFECTIVENESS OF A PP7RLP PARTICLE IN DELIVERING THE CRISPR/CAS9 SYSTEM (GUIDE RNA+RNA CODING CAS91 IN HCT116-GFP CELLS

I. Material & Methods

1. Plasmid Construction 1.1. Plasmids for Producing PP7 (NC)-RLP 2X Lentiviral Particles According to the Invention In this Example, the PP7 (NC)-RLP 2X particles will be called PP7 (NC)-RLP 2X 2X as they comprise two different series of stem-loop motifs of PP7 (1st series of motifs: SEQ ID No.2 followed by SEQ ID No.4 and 2nd series of motifs: SEQ ID No.5 followed by SEQ ID No.6).

Expression Plasmids for a Sequence of Interest:

The first expression plasmid bears an expression cassette as described in FIG. 34 (pcDNA-EF1-Cas9-PP7 2X), with or without an intron sequence or RNA stabilizing sequence. In order to transport the mRNAs into the lentiviral particles, 2 repetitions of the stem-loop motif of the PP7 RNA (ctagaaaggagcagacgatatggcgtcgctccctgcag SEQ ID No.2 and ctagaaaccagcagagcatatgggctcgctggctgcag SEQ ID No.4) were inserted in an expression cassette downstream of the sequence of the Cas9 enzyme (FIG. 34). The promoter used is the EF1 promoter (FIG. 34) but other promoters may be used. The plasmid sequence of interest is a DNA coding the RNA of the Cas9 protein (FIG. 34), in its wild-type form (WT) or in its mutated form (N).

The second expression plasmid bears an expression cassette as described in FIG. 35 (pcDNA-U6-GuideD1Chimeric-PP7 2X), with or without an intron sequence or RNA stabilizing sequence. In order to transport the guide RNAs into the lentiviral particles, 2 repetitions of the stem-loop motif of the PP7 RNA (ggagcagacga-tatggcgtcgctcc SEQ ID No.5 and ccagcagag-catatgggctcgctgg SEQ ID No.6) were inserted in an expression cassette in the part of the scaffold of the guide (chimeric guide, FIG. 35). The promoter used is U6 but other promoters may be used, such as promoter H1. Use of a promoter of the RNA pol III dependent type, such as H1 or U6, requires the presence of a transcription termination signal (Term). The sequence of interest is a non-coding RNA targeting the sequence of the GFP (sgRNA=guide RNA).

These expression plasmids were used for co-encapsidating, in the same PP7RLP 2X particle, both the RNA coding Cas9 and the guide RNA targeting the sequence of the GFP integrated into the genome of the target cells (HCT116-GFP CloneD2).

Encapsidation Plasmid:

The lentiviral particle was modified to contain, in the nucleocapsid protein, in place of the second Zn finger domain, the sequence of the "Coat" protein of the bacteriophage PP7. The p8.74 encapsidation plasmid bearing the genes coding the structural and functional proteins (Gag, Pol) used for production of the PP7RLP 2X particles is modified in accordance with the strategy illustrated in FIG. 36a: this p8.74 plasmid is used for generating, by assembly PCR, a plasmid lacking the second zinc finger of the p8.74ΔZF nucleocapsid protein. The second zinc finger is substituted by the "Coat" protein of the PP7 bacteriophage by HpaI cloning, to generate the p8.74ΔZF-PP7-Coat plasmid. This gives the construct illustrated in FIG. 36b. The Pol coding sequence may be deleted or mutated in certain functional elements such as for example the sequence coding reverse transcriptase (RT) or integrase (IN) without altering the function of the PP7RLP 2X 2X.

Envelope Plasmid (pENV):

This plasmid bears the gene coding an envelope protein, which may be VSV-G coding the envelope protein of the Vesicular stomatitis virus (FIG. 3).

More particularly, these plasmids are used for producing PP7RLP Cas9 2X-GuideD1Chimeric 2X lentiviral particles.

1.2. Plasmids for Producing ILV-GFP Integrative Lentiviral Vectors for Generating the HCT116-GFP Clone D2 Target Cells These plasmids are prepared by a method identical to that in Example 1.

2. Production of Batches of Lentiviral Particles and Lentiviral Vectors

After transfection of the plasmids on producer cells, the supernatants are harvested and used crude or concentrated/purified according to one of the aforementioned methods P1 or P2 as described in application WO 2013/014537.

2.1 Production of the Lentiviral Particles and Lentiviral Vectors

Production is carried out in a 10-stack CellSTACK (6360 cm², Corning) with HEK293T producer cells (ATCC, CRL-11268), cultured in Dulbecco's Modified Eagle's Medium (DMEM, Gibco, Paisley, UK) supplemented with 1% penicillin/streptomycin and 1% of ultraglutamine (PAA) at 37° C. in a humid atmosphere at 5% $CO_2$.

The PP7 (NC)-RLP 2X 2X particles, preferably PP7RLP-Cas9 2X-GuideD1Chimeric 2X, are produced by transfection of the following four plasmids:

The two expression plasmids described above, of which pcDNA-U6-GuideD1Chimeric-PP7 2X plasmid (the expression cassette of which is illustrated in FIG. 35) is used in double the quantity of the pcDNA-EF1-Cas9-PP7 2X plasmid (the expression cassette of which is illustrated in FIG. 34);

p8.74ΔZF-PP7-Coat (the expression cassette of which is illustrated in FIG. 36b);

pENV bearing the envelope VSV-G (the expression cassette of which is illustrated in FIG. 3).

The PP7 (NC)-RLP 2X 2X particles are produced by the method described in Example 4. 24 hours after standard transfection with calcium phosphate, the culture supernatant is replaced with fresh unsupplemented DMEM medium. The producer cells are incubated at 37° C./5% $CO_2$. After changing the medium, the supernatant is harvested four times (32 h, 48 h, 56 h and 72 h post-transfection). Each collection is clarified by 5 min centrifugation at 3000 g before being microfiltered on a 0.45 µm filter (Stericup®, Millipore). All the collections are then pooled to compose the crude supernatant.

The ILV-GFP lentiviral vectors are produced as described in Example 1.

2.2 Concentration and Purification of the Lentiviral Particles and Lentiviral Vectors The lentiviral particles and the lentiviral vectors are concentrated and purified according to method P1 described in Example 1.

3. Titration of the Batches of Lentiviral Particles and Lentiviral Vectors

The lentiviral particles and the lentiviral vectors are titrated as described in Example 1.

4. Generation of Target Cells and Transduction by PP7 (NC)-RLP 2X 2X Lentiviral Particles According to the Invention This example aims to show that a PP7RLP particle delivering the CRISPR Cas9 system to target cells has a dose effect on the effectiveness of genome editing. At the end of this transfer of RNA, the CRISPR/Cas9 system should be functional and generate breaks of double-stranded DNA allowing knock-out of the target gene, and thus transform the GFP+ cells into GFP− cells, using one and the same tool for transfer of the 2 constituents of the CRISPR/Cas9 system.

4.1 HCT116-GFP cloneD2 Target Cells

This done is prepared by a method identical to that in Example 1.

4.2 Transduction of the HCT116-GFP CloneD2 Target Cells by PP7 (NC)-RLP 2X 2X Lentiviral Particles According to the Invention The HCT116-GFP CloneD2 target cells are seeded in a 24-well plate at 25000 cells/cm² and incubated for 24 h at 37° C./5% $CO_2$. The HCT116-GFP CloneD2 target cells are transduced by the PP7RLP 2X 2X particles delivering both Cas9 and the guide D1Chimeric at different doses (0.5; 1; 5 or 10 µg p24/cell) in the presence of 8 µg/mL Polybrene®. A cell defence mechanism inhibitor, BX795 (Invivogen), is used at a concentration of 6 µM in the case of the PP7RLP 2X 2X particles. The transduction supernatant is removed 17 hours later and replaced with fresh supplemented culture medium. A second transduction was carried out under the same conditions 6 days after the first transduction (FIG. 37). 7 days after the last transduction, the target cells are recovered and the percentage of cells expressing GFP is quantified by cytometry (Macs Quant VYB, Miltenyi Biotec).

II. Results

The purpose of this experiment is to study the ability of the PP7RLP particles to induce a dose effect on genome editing, by simultaneously transferring an RNA coding Cas9 and a guide RNA targeting the sequence coding the protein GFP at different concentrations and by measuring the extinction of the GFP in HCT116-GFP CloneD2's by cytometry, with a first transduction (FIG. 37, % of T1 positive cells) and a second transduction (FIG. 37, % of T2 positive cells).

Firstly, the results presented in FIG. 37 show that the non-transduced (NT) HCT116 cells are not fluorescent, whereas the HCT116-GFP cloneD2 target cells are 100% fluorescent. When the HCT116-GFP doneD2 cells are transduced with the PP7RLP 2X particles delivering the complete CRISPR/Cas9 system, 7 days after the first and the second transduction of the target cells (FIG. 37, % of T2 positive cells), a decrease is noted in the number of fluorescent cells following a dose effect. Just as for the MS2RLP particles, a stronger extinction of the GFP is observed after the second transduction than after the first transduction whatever the number of pg p24/cell (0.5, 1, 5 or 10).

After the second transduction, there is knock-out of the GFP gene of the order of 33% for a dose of 0.5 pg p24/cell, of the order of 54% for 1 pg p24/cell, of the order of 85% for 5 pg p24/cell and finally of the order of 75% at 10 pg p24/cell. A second transduction therefore allows the effectiveness of knock-out of the GFP to be increased with respect to the first transduction. The higher the dose of PP7RLP particles, the greater the knock-out of the GFP, reaching a maximum effectiveness of extinction at a dose of 5 pg p24/cell. Moreover, the PP7RLP particles have an "off-target effect" as described in Example 4, between the doses of PP7RLP particles 5 pg p24/cell and 10 pg p24/cell. The dose and the number of transductions used are therefore important factors to be taken into account for the effectiveness of the PP7RLP particles in delivering the complete CRISPR/Cas9 system.

The PP7RLP particles give a higher percentage extinction of the GFP in the HCT116-GFP cloneD2 target cells than the MS2RLP particles (FIG. 37 and FIG. 22 respectively). At the optimum dose of each particle, knock-out of the GFP gene of the order of 85% for 5 pg p24/cell of PP7RLP particles vs. 82% for 10 pg p24/cell of MS2RLP particles is noted, or a twice higher dose than for the PP7RLP particles. The effectiveness of the PP7RLP particles makes it possible to optimize CRISPR/Cas9 RNA transfer, in particular in delicate primary cells, which may be sensitive to several transductions. In conclusion, these PP7RLP particles mark themselves out as being the best tool for co-delivering the CRISPR/Cas9 system, with the use of a single type of particles.

EXAMPLE 13: IMPACT OF THE WILD-TYPE GAG-POL PRECURSOR FOR PRODUCTION OF THE MS2RLP-ZSGREEN1 12X PARTICLES WITH A VIEW TO OPTIMIZATION OF THE EFFECTIVE MS2RLP-CRISPR/CAS9 PARTICLES (GUIDE RNA+RNA CODING CAS9)

I. Material & Methods

1. Plasmid Construction 1.1 Plasmid for Producing an MS2RLP 12X Lentiviral Particle According to the Invention Expression Plasmid for a Sequence of Interest:

The expression plasmid bears an expression cassette (as described in FIG. 38) with or without an intron sequence or RNA stabilizing sequence. In order to transport the RNAs into the lentiviral particles, 12 repetitions of the stem-loop motif of the MS2 RNA (ctagaaaacatgaggatcacccatgtctgcag, SEQ ID No.1) were inserted in an expression cassette downstream of the sequence of the ZsGreenI protein. The promoter used is the EF1 promoter but other promoters may be used. The plasmid sequence of interest is a DNA coding the RNA of the ZsGreenI protein.

Encapsidation Plasmids:

The first encapsidation plasmid is the p8.74ΔZF plasmid of which expression cassette is described in FIG. 2b, obtained by modification of the p8.74 encapsidation plasmid to contain, in the nucleocapsid protein, in place of the second Zn finger domain, the sequence of the "Coat" protein of the MS2 bacteriophage, according to the strategy Illustrated in FIG. 2a and as described in Example 1.

The second encapsidation plasmid is the p8.74 plasmid, bearing the genes coding the wild-type structural and functional proteins (Gag, Pol), as presented in FIG. 6.

Envelope Plasmid (pENV):

This plasmid bears the gene coding an envelope protein, which may be VSVG coding the envelope protein of the Vesicular stomatitis virus (FIG. 3).

More particularly, these plasmids are used for producing MS2RLP-ZsGreenI12X lentiviral particles.

1.2 Plasmid for Producing Control Integrative Lentiviral Vectors ILV-ZsGreenI

Expression Plasmid for a Sequence of Interest:

The expression plasmid bears an expression cassette as described in FIG. 41. This plasmid may contain other elements such as the native sequence WPRE (Woodchuck Hepatitis Virus Posttranscriptional Regulatory Element) or the cPPT/CTS sequence. Viral pathogenicity is eliminated by substitution of regions of the viral genome required for retroviral replication by the transgene. The promoter used is the EF1 promoter, but other promoters may be used. The plasmid sequence of interest is a DNA coding the RNA of the ZsGreenI protein.

Encapsidation Plasmid:

The p8.74 encapsidation plasmid, bearing the genes coding the structural and functional proteins (Gag, Pol), is used for production of the integrative lentiviral vectors (FIG. 6).

Envelope Plasmid (pENV):

This plasmid is identical to the envelope plasmid used for producing MS2RLP lentiviral particles (FIG. 3).

2. Production of Batches of Lentiviral Particles and Lentiviral Vectors 2.1 Production of the Lentiviral Particles Production is carried out in a 10-stack CellSTACK (6360 cm², Corning) with HEK293T producer cells (ATCC, CRL-11268), cultured in Dulbecco's Modified Eagle's Medium (DMEM, Gibco, Paisley, UK) supplemented with 1% penicillin/streptomycin and 1% of ultraglutamine (PAA) at 37° C. in a humid atmosphere at 5% $CO_2$.

The MS2RLP 12X particles are produced by transfection of the following four plasmids:

The expression plasmid described above, of which the expression cassette is illustrated in FIG. 38;

p8.74ΔZF-MS2-Coat (the expression cassette of which is illustrated in FIG. 2b) and the p8.74 plasmid (the expression cassette of which is illustrated in FIG. 6), using four different ratios of the two encapsidation plasmids, [100%-0%]; [90%-10%]; [80%-20%] and [50%-50%], respectively;

pENV bearing the envelope VSV-G (the expression cassette of which is illustrated in FIG. 3).

The MS2RLP-ZsGreenI 12X lentiviral particles are produced as described in Example 1, i.e. with the following respective proportions of the plasmids: 40% of the expression plasmid, 30% of the p8.74 plasmid (or p8.74ΔZF), 30% of the pENV plasmid (ratio [100%-0%]).

More particularly, the respective proportions of the plasmids are as follows:

ratio [90%-10%]:40% of the expression plasmid, 27% of the p8.74ΔZF plasmid, 3% of the p8.74 plasmid, 30% of the pENV plasmid;

ratio [80%-20%]:40% of the expression plasmid, 24% of the p8.74ΔZF plasmid, 6% of the p8.74 plasmid, 30% of the pENV plasmid;

ratio [50%-50%]:40% of the expression plasmid, 15% of the p8.74ΔZF plasmid, 15% of the p8.74 plasmid, 30% of the pENV plasmid.

In the case of the production of an MS2 (NC)-RLP 12X 2X particle for transferring the complete CRISPR/Cas9 system, the particles are produced by the method as described in Example 8. More particularly, the respective proportions of the plasmids are as follows: 33% of the expression plasmid coding the guide, 17% of the expression plasmid coding Cas9 (the quantity of expression plasmid coding the guide is doubled with respect to that of the expression plasmid coding Cas9), 25% of the p8.74ΔZF plasmid, 25% of the pENV plasmid (ratio [100%-0%]), More particularly, the respective proportions of the plasmids are as follows:

ratio [90%-10%]:40% of the expression plasmid, 22.5% of the p8.74ΔZF plasmid, 2.5% of the p8.74 plasmid, 30% of the pENV plasmid;

ratio [80%-20%]:40% of the expression plasmid, 20% of the p8.74ΔZF plasmid, 5% of the p8.74 plasmid, 30% of the pENV plasmid ratio [50%-50%]:40% of the expression plasmid, 12.5% of the p8.74ΔZF plasmid, 12.5% of the p8.74 plasmid, 30% of the pENV plasmid More particularly, these plasmids are used for producing the MS2RLP-ZsGreenI 12X lentiviral particles.

The integrative lentiviral vectors ILV-ZsGreenI containing the EF1-ZsGreenI expression cassette are produced as a control.

For the ILV-ZsGreenI batches, the transfection mixture consists of the following three plasmids:

the expression plasmid of which the expression cassette is illustrated in FIG. 40 the p8.74 plasmid (of which the expression cassette is illustrated in FIG. 6)

the pENV plasmid bearing the envelope VSV-G (of which the expression cassette is illustrated in FIG. 3).

24 hours after standard transfection with calcium phosphate, the culture supernatant is replaced with fresh unsupplemented DMEM medium. The producer cells are incubated at 37° C./5% $CO_2$. After changing the medium, the supernatant is harvested four times (32 h, 48 h, 56 h and 72 h post-transfection). Each collection is clarified by 5 min centrifugation at 3000 g before being microfiltered on a 0.45 μm filter (Stericup®, Millipore). All the collections are then pooled to compose the crude supernatant.

2.2 Concentration and Purification of the Lentiviral Particles

The lentiviral particles and the lentiviral vectors are concentrated and purified according to method P1 described in Example 1.

3. Titration of the Batches of Lentiviral Particles and Lentiviral Vectors

The lentiviral particles and the lentiviral vectors are titrated as described in Example 1.

4. Preparation of the Target Cells and Transduction by MS2RLP 12X Lentiviral Particles According to the Invention Jurkat target cells (ATCC TIB-152) are seeded at 200000 cells/mL in a 96-well plate, transduced by the MS2RLP 12X particles at two doses (2 and 10 µg p24/cell), or by control ILV-ZsGreenI lentiviral vectors at MOI40, in the presence of 4 µg/mL Polybrene® and then incubated at 37° C./5% $CO_2$. A cell defence mechanism inhibitor, BX795 (Invivogen), is used at a concentration of 6 µM in the case of the MS2RLP 12X particles. The transduction supernatant is removed 5 hours later and replaced with fresh supplemented culture medium. 24 h post-transduction, the target cells are recovered and the percentage of cells expressing ZsGreenI is quantified by cytometry (Macs Quant VYB, Miltenyi Biotec).

5. Analysis of Maturation of the MS2RLP Viral Particles by Anti-p24 Western Blot 48 h after transfection of the producer cells (HEK293T) with the plasmids for producing the MS2RLP 12X particles, the culture supernatants are recovered and then concentrated according to method P1, as described in Example 1, and titrated by quantification of the p24 protein, as described in Example 1. The equivalent of 15 ng of p24 is loaded for each condition of ratio of the plasmids p8.74ΔZF-MS2-Coat/ p8.74 on an SDS-PAGE 4/12% denaturing gel and then migrated for 1 h at 200V in MOPS1X buffer. After transfer onto a nylon membrane, the proteins are hybridized with an anti-p24 antibody [clone 39/5.4 A, Abcam]. The Western blot is developed using the Pierce™ Fast Western Blot Kit, ECL Substrate (Pierce). The bands are visualized by chemiluminescence on autoradiography film.

II. Results

This example aims to show that it is possible to improve the functionality of the MS2RLP particles by improving the maturation of the GAG precursor during production of the particles, demonstrated by the proof of concept on the production of MS2RLP 12X particles. The p8.74ΔZF-MS2 plasmid allows expression of a GAG precursor comprising the Coat protein of the bacteriophage in place of the second zinc finger of the Nucleocapsid protein. This Coat protein is likely to disturb the maturation of the GAG precursor, when it is cleaved into three proteins: the Matrix protein, the Capsid protein and the Nucleocapsid protein. These three proteins are indispensable to the structure of the viral particles.

Supply of the wild-type GAG precursor by the p8.74 plasmid in addition to the p8.74ΔZF-MS2-Coat encapsidation plasmid during production of the MS2RLP-ZsGreenI 12X particles might allow enhancement of the maturation of the GAG precursor when it is expressed owing to the p8.74ΔZF-MS2 plasmid, and thus increase the functionality of the MS2RLP particles.

The purpose of this experiment is to evaluate the impact of the p8.74 plasmid when it is co-transfected, in the producer cells of the MS2RLP 12X particles, at the same time as the p8.74ΔZF-MS2-Coat encapsidation plasmid making it possible to improve the maturation of the GAG precursor, and thus make the final particles more functional for the transduction of target cells.

In this example, four ratios of p8.74ΔZF-MS2-Coat/p8.74 encapsidation plasmids are tested:100/0; 90/10; 80/20 and 50/50. An integrative vector ILV expressing ZsGreenI is used as a control. The cells are transduced at two quantities of p24/ml:2 pg p24/cell (FIG. 41) and 10 pg p24/cell (FIG. 42).

Firstly, the results presented in FIG. 41 show that for the cells that were not transduced, the percentage of fluorescent cells is very dose to 0, whereas the cells transduced by the MS2RLP-ZsGreenI 12X particles are fluorescent at more than 99% whatever ratio of encapsidation plasmids is used. It is important to note that the fluorescence intensity of ZsGreenI increases as a function of the increase in the quantity of p8.74 plasmid. The cells transduced by the MS2RLP-ZsGreenI 12X particles produced with 50% of the p8.74ΔZF-MS2-Coat encapsidation plasmid and 50% of the p8.74 plasmid have a fluorescence intensity of 7.76 whereas that of the cells transduced by the MS2RLP-ZsGreenI 12X particles produced only with the p8.74ΔZF-MS2-Coat encapsidation plasmid is 3.5.

FIG. 42 shows the same result in terms of percentage of cells transduced. Regarding the fluorescence intensity, as the quantity of p8.74 plasmid increases, the fluorescence intensity increases, as shown in FIG. 41. The cells transduced by the MS2RLP-ZsGreenI 12X particles produced with 50% of the p8.74ΔZF-MS2-Coat encapsidation plasmid and 50% of the p8.74 plasmid have a fluorescence intensity of 60.67 whereas that of the cells transduced by the MS2RLP-ZsGreenI 12X particles produced only with the p8.74ΔZF-MS2-Coat encapsidation plasmid is 11.48.

This signifies that at doses of 2 µg and 10 pg p24/cell, the fluorescence obtained is two and five times greater, respectively, when the particles are produced with 50% of the p8.74ΔZF-MS2-Coat encapsidation plasmid and 50% of the p8.74 plasmid than when they are produced only with the p8.74ΔZF-MS2-Coat plasmid.

Use of the p8.74 plasmid in the production of MS2RLP particles, in co-transfection with the p8.74ΔZF-MS2-Coat plasmid, therefore supplied a gain on the improvement of the functionality of the MS2RLP-ZsGreenI 12X particles, with a view to optimization of the MS2RLP particles.

FIG. 43 shows the maturation of the MS2RLP-ZsGreenI 12X particles in biochemical terms, by searching for the p24 protein in the production supernatant containing the particles. It corresponds to an analysis of the viral supernatants by anti-p24 Western blot, at two exposure times of the autoradiography film, one minute (FIG. 43a) and fifteen seconds (FIG. 43b).

In the case of an integrative lentiviral particle derived from HIV, produced solely with the p8.74 plasmid as encapsidation plasmid, the p24 protein is detectable at four levels:
  in the p160 protein precursor (GAG-POL)
  in the p55 protein precursor (GAG),
  in the mature protein state (p24)
  in other intermediate protein precursors in the course of maturation (between p160 and p55, and between p55 and p24).

If maturation takes place normally, the p24 protein should be detected in larger quantities in the mature state (p24) than in the state of protein precursors (p160, p55) or of intermediate protein precursors. In fact, maturation of the viral particles takes place after release of the particle by the producer cell. In other words, during their production, the particles bud at the surface of the producer cell, and then are released from the cell in the state of immature particles. It is only after release of the particles in the supernatant that the GAG-POL and GAG protein precursors mature into definitive proteins.

In the case of an MS2RLP 12X particle derived from HIV, produced solely with the p8.74ΔZF-MS2-Coat plasmid as encapsidation plasmid, the p24 protein is detectable at four levels:

in the p172 protein precursor (GAGΔZF-MS2-Coat-POL)
in the p67 protein precursor (GAGΔZF-MS2-Coat),
in the mature protein state (p24)
in other intermediate protein precursors in the course of maturation (between p172 and p67, and between p67 and p24).

In this MS2RLP-ZsGreenI 12X particle, each precursor is heavier than 12 kDa, which corresponds to the size of the Coat protein of the MS2 bacteriophage inserted in the second zinc finger of the Nucleocapsid protein.

FIG. 43 shows, on track ILV, the different forms of protein precursors, p160 (GAG-POL), p55 (GAG) as well as the perfectly mature p24 protein. There is a majority of mature p24 protein, compared to the protein precursor forms. On track 100/0, corresponding to MS2RLP-ZsGreenI 12X particles produced solely with the p8.74ΔZF-MS2-Coat plasmid as encapsidation plasmid, the proportion of precursors/mature p24 protein increases with respect to ILV, showing that insertion of the Coat protein of the MS2 bacteriophage decreases the maturation of the viral particles. On tracks 90/10, 80/20 and 50/50, the proportion of protein precursors p172 and p67 decreases to the benefit of the protein precursors p160 and p55 respectively, reaching one and the same expression level for track 50/50. Addition of the p8.74 plasmid to the p8.74ΔZF-MS2-Coat plasmid as encapsidation plasmid for producing particles results in an increase in the proportion of the mature p24 protein (FIG. 43b, 15 seconds of exposure). This result shows that to promote maturation of the protein precursors in the MS2RLP particles, it is necessary to add at least 10% of p8.74 plasmid in addition to the p8.74ΔZF-MS2-Coat plasmid as encapsidation plasmid for producing particles.

In conclusion, production of the MS2RLP particles using at least 10% of p8.74 plasmid in addition to the p8.74ΔZF-MS2-Coat plasmid as encapsidation plasmid not only makes it possible to increase the maturation of the precursors into mature proteins, but in addition makes it possible to increase the functionality of the particles after transduction of target cells.

EXAMPLE 14: RECRUITMENT OF NON-VIRAL RNAS DIRECTED BY TWO DIFFERENT ENCAPSIDATION SEQUENCES (MS2 AND PP71 WITH A VIEW TO OPTIMIZATION OF TRANSFER OF THE CRISPR SYSTEM BY AN RLP PARTICLE (MODULATION OF THE TYPES OF RNA ENCAPSIDATED)

I. Material & Methods
1. Plasmid Construction
1.1 Plasmids for Producing MS2/PP7(NC)-RLP 12X 2X Lentiviral Particles According to the Invention Expression Plasmids for a Sequence of Interest:

The first expression plasmid bears an expression cassette as described in FIG. 38, with or without an intron sequence or RNA stabilizing sequence. In order to transport the RNAs into the lentiviral particles, 12 repetitions of the stem-loop motif of the MS2 RNA (ctagaaaacatgaggatcacccatgtctgcag, SEQ ID No.1) were inserted in an expression cassette downstream of the RNA coding a reporter protein such as native firefly luciferase, a green fluorescent protein (ZsGreenI), a red fluorescent protein (mCherry) as described in FIG. 38, or a cDNA coding a protein, for example a nuclease, such as the Cas9 protein in its wild-type form (WT) or in its mutated form (N). The promoter used may be the CMV or EF1 promoter (FIG. 38) but other promoters may be used.

The second expression plasmid bears an expression cassette as described in FIG. 39, with or without an intron sequence or RNA stabilizing sequence. In order to transport the mRNAs into the lentiviral particles, 2 repetitions of the stem-loop motif of the PP7 RNA (ctagaaaggagcagacgatatggcgtcgctccctgcag SEQ ID No.2 and ctagaaaccagcagag-catatgggctcgctggctgcag SEQ ID No.4) were inserted in an expression cassette downstream of the RNA coding a reporter protein such as native firefly luciferase, a green fluorescent protein (ZsGreenI), a red fluorescent protein (mCherry) as described in FIG. 39, or a cDNA coding a protein, for example a nuclease, such as the Cas9 protein in its wild-type form (WT) or in its mutated form (N). The promoter used may be the CMV or EF1 promoter (FIG. 39) but other promoters may be used.

Encapsidation Plasmids:

The lentiviral particle was modified to contain the sequence of the "Coat" protein of the MS2 bacteriophage in the nucleocapsid protein, in place of the second Zn finger domain, or PP7. The p8.74 encapsidation plasmid bearing the genes coding the structural and functional proteins (Gag, Pol) used for production of the MS2RLP 12X particles is modified in accordance with the strategy illustrated in FIG. 2a: this p8.74 plasmid is used for generating, by assembly PCR, a plasmid lacking the second zinc finger of the p8.74ΔZF nucleocapsid protein. The second zinc finger is substituted by the "Coat" protein of the MS2 bacteriophage by HpaI cloning, to generate the p8.74ΔZF-MS2-Coat plasmid. This gives the construct illustrated in FIG. 2b. The Pol coding sequence may be deleted or mutated in certain functional elements such as for example the sequence coding reverse transcriptase (RT) or integrase (IN) without altering the function of the MS2RLP 12X.

The p8.74 encapsidation plasmid bearing the genes coding the structural and functional proteins (Gag, Pol) used for production of the PP7RLP 2X particles is modified in accordance with the strategy illustrated in FIG. 36a: this p8.74 plasmid is used for generating, by assembly PCR, a plasmid lacking the second zinc finger of the p8.74ΔZF nucleocapsid protein. The second zinc finger is substituted by the "Coat" protein of the PP7 bacteriophage by HpaI cloning, to generate the p8.74ΔZF-PP7-Coat plasmid. This gives the construct illustrated in FIG. 36b. The Pol coding sequence may be deleted or mutated in certain functional elements such as for example the sequence coding reverse transcriptase (RT) or integrase (IN) without altering the function of the PP7RLP 2X.

Envelope Plasmid (pENV):

This plasmid bears the gene coding an envelope protein, which may be VSV-G coding the envelope protein of the Vesicular stomatitis virus (FIG. 3).

More particularly, these plasmids are used for producing MS2/PP7-RLP-mCherry 12X-ZsGreenI 2X lentiviral particles.

1.2 Plasmids for Producing Control MS2(NC)-RLP 12X Lentiviral Particles According to the Invention Expression Plasmid for a Sequence of Interest:

The expression plasmid bears an expression cassette as described in FIG. 38 with or without an intron sequence or RNA stabilizing sequence. In order to transport the RNAs into the lentiviral particles, 12 repetitions of the stem-loop motif of the MS2 RNA (ctagaaaacatgaggatcacccatgtctgcag, SEQ ID No.1) were inserted in an expression cassette downstream of the RNA of a reporter protein such as native firefly luciferase, a green fluorescent protein (ZsGreenI), a red fluorescent protein (mCherry) as described in FIG. 38, or a cDNA coding a protein, for example a nuclease, such as the Cas9 protein in its wild-type form (WT) or in its mutated form (N). The promoter used may be the CMV or EF1 promoter (FIG. 38) but other promoters may be used.

Encapsidation Plasmid:

The lentiviral particle was modified to contain the sequence of the "Coat" protein of the MS2 bacteriophage in the nucleocapsid protein, in place of the second Zn finger domain. The p8.74 encapsidation plasmid bearing the genes coding the structural and functional proteins (Gag, Pol) used for production of the MS2RLP 12X particles is modified in accordance with the strategy illustrated in FIG. 2a: this p8.74 plasmid is used for generating, by assembly PCR, a plasmid lacking the second zinc finger of the p8.74ΔZF nucleocapsid protein. The second zinc finger is substituted by the "Coat" protein of the MS2 bacteriophage by HpaI cloning, to generate the p8.74ΔZF-MS2-Coat plasmid. This gives the construct illustrated in FIG. 2b. The Pol coding sequence may be deleted or mutated in certain functional elements such as for example the sequence coding reverse transcriptase (RT) or integrase (IN) without altering the function of the MS2RLP 12X.

Envelope Plasmid (pENV):

This plasmid bears the gene coding an envelope protein, which may be VSV-G coding the envelope protein of the Vesicular stomatitis virus (FIG. 3).

More particularly, these plasmids are used for producing MS2RLP-mCherry 12X lentiviral particles.

1.3 Plasmids for Producing Control PP7(NC)-RLP 2X Lentiviral Particles According to the Invention Expression Plasmid for a Sequence of Interest:

The expression plasmid bears an expression cassette as described in FIG. 39, with or without an intron sequence or RNA stabilizing sequence. In order to transport the mRNAs into the lentiviral particles, 2 repetitions of the stem-loop motif of the PP7 RNA (ctagaaaggagcagacga-tatggcgtcgctccctgcag SEQ ID No.2 and ctagaaaccagcagag-catatgggctcgctggctgcag SEQ ID No.4) were inserted in an expression cassette downstream of the RNA coding a reporter protein such as native firefly luciferase, a green fluorescent protein (ZsGreenI), a red fluorescent protein (mCherry) as described in FIG. 39, or a cDNA coding a protein, for example a nuclease, such as the Cas9 protein in its wild-type form (WT) or in its mutated form (N). The promoter used may be the CMV or EF1 promoter (FIG. 39) but other promoters may be used.

Encapsidation Plasmid:

The lentiviral particle was modified to contain the sequence of the "Coat" protein of the PP7 bacteriophage in the nucleocapsid protein, in place of the second Zn finger domain. The p8.74 encapsidation plasmid bearing the genes coding the structural and functional proteins (Gag, Pol) used for production of the PP7RLP 2X particles is modified in accordance with the strategy illustrated in FIG. 36a: this p8.74 plasmid is used for generating, by assembly PCR, a plasmid lacking the second zinc finger of the p8.74ΔZF nucleocapsid protein. The second zinc finger is substituted by the "Coat" protein of the PP7 bacteriophage by HpaI cloning, to generate the p8.74ΔZF-PP7-Coat plasmid. This gives the construct illustrated in FIG. 36b. The Pol coding sequence may be deleted or mutated in certain functional elements such as for example the sequence coding reverse transcriptase (RT) or integrase (IN) without altering the function of the PP7RLP 2X.

Envelope Plasmid (pENV):

This plasmid bears the gene coding an envelope protein, which may be VSV-G coding the envelope protein of the Vesicular stomatitis virus (FIG. 3).

More particularly, these plasmids are used for producing PP7RLP-ZsGreenI 2X lentiviral particles.

2. Production of the Batches of Lentiviral Particles

After transfection of the plasmids on producer cells, the supernatants are harvested and used crude or concentrated/purified according to one of the aforementioned methods P1 or P2 as described in application WO 2013/014537.

2.1 Production of the Lentiviral Particles

Production is carried out in a 10-stack CellSTACK (6360 cm$^2$, Corning) with HEK293T producer cells (ATCC, CRL-11268), cultured in Dulbecco's Modified Eagle's Medium (DMEM, Gibco, Paisley, UK) supplemented with 1% penicillin/streptomycin and 1% of ultraglutamine (PAA) at 37° C. in a humid atmosphere at 5% $CO_2$.

The MS2/PP7(NC)-RLP 12X 2X, preferably MS2/PP7-RLP-mCherry 12X-ZsGreenI 2X, lentiviral particles are produced by transfection of the following five plasmids:

The two expression plasmids described above including the pcDNA.EF1.mCherry.MS2 12X plasmid (the expression cassette of which is illustrated in FIG. 38) (50%) and the pcDNA.EF1.ZsGreenI.PP7 2X plasmid (of which the expression cassette is illustrated in FIG. 39) (50%), used in a single quantity;

p8.74ΔZF-PP7-Coat (50%) of which the expression cassette is illustrated in FIG. 36b and p8.74ΔZF-MS2-Coat (50%) of which expression cassette is illustrated in FIG. 2b;

pENV bearing the envelope VSV-G of which the expression cassette is illustrated in FIG. 3.

The MS2/PP7 (NC)-RLP 12X 2X lentiviral particles are produced as described in Example 1, i.e. with the following respective proportions of the plasmids:40% of the expression plasmid, 30% of the p8.74 plasmid (or p8.74ΔZF), 30% of the pENV plasmid. More particularly, the respective proportions of the plasmids are as follows: 20% of the pcDNA.EF1.mCherry.MS2 12X expression plasmid, 20% of the pcDNA.EF1.ZsGreenI.PP7 2X expression plasmid, 30% of the p8.74ΔZF plasmid, 30% of the pENV plasmid.

In the case of the production of an MS2/PP7 (NC)-RLP 12X 2X particle for transferring the complete CRISPR/Cas9 system, the particles are produced by the method as described in Example 8. More particularly, the respective proportions of the plasmids are as follows: 33% of the expression plasmid coding the guide, 17% of the expression plasmid coding Cas9 (the quantity of expression plasmid coding the guide is doubled with respect to that of the expression plasmid coding Cas9), 25% of the p8.74ΔZF plasmid and 25% of the pENV plasmid.

The control MS2 (NC)-RLP 12X lentiviral particles, preferably MS2-RLP-mCherry 12X, are produced by transfection of the following three plasmids:

The expression plasmid described above pcDNA.EF1.mCherry.MS2 12X (of which the expression cassette is illustrated in XXXVIII);

p8.74ΔZF-MS2-Coat of which the expression cassette is illustrated in FIG. 2b;

pENV bearing the envelope VSV-G of which the expression cassette is illustrated in FIG. 3.

The MS2 (NC)-RLP 12X lentiviral particles are produced as described in Example 1.

The control PP7 (NC)-RLP 2X lentiviral particles, preferably PP7-RLP-ZsGreenI 2X, are produced by transfection of the following three plasmids:

The expression plasmid described above pcDNA.EF1.ZsGreenI.PP7 2X (of which the expression cassette is illustrated in FIG. 39);

p8.74ΔZF-PP7-Coat of which the expression cassette is illustrated in FIG. 36b;

pENV bearing the envelope VSV-G of which the expression cassette is illustrated in FIG. 3.

The PP7(NC)-RLP 2X lentiviral particles are produced as described in Example 1.

24 hours after standard transfection with calcium phosphate, the culture supernatant is replaced with fresh unsupplemented DMEM medium. The producer cells are incubated at 37° C./5% $CO_2$. After changing the medium, the supernatant is harvested four times (32 h, 48 h, 56 h and 72 h post-transfection). Each collection is clarified by 5 min centrifugation at 3000 g before being microfiltered on a 0.45 µm filter (Stericup®, Millipore). All the collections are then pooled to compose the crude supernatant.

2.2 Concentration and Purification of the Lentiviral Particles

The lentiviral particles are concentrated and purified according to method P1 described in Example 1.

3. Titration of the Batches of Lentiviral Particles

The lentiviral particles are titrated as described in Example 1.

4. Transduction by MS2PP7(NC)-RLP 12X 2X Lentiviral Particles According to the Invention This example is carried out using MS2/PP7(NC)-RLP 12X 2X particles allowing transfer of several types of RNAs and therefore expression of several different proteins (ZsGreenI+mCherry).

HCT116 target cells (ATCC, CCL-247) were seeded in a 24-well plate and incubated for 24 h at 37° C./5% $CO_2$ and were transduced by the MS2/PP7(NC)-RLP 12X 2X particles at a dose of 10 pg p24/cell.

The controls carried out are as follows:
transduction with the MS2RLP-mCherry 12X and PP7RLP-ZsGreenI 2X lentiviral particles, at a dose of 10 pg p24/cell each;
transduction with the MS2RLP-mCherry 12X lentiviral particles alone, at a dose of 10 pg p24/cell;
transduction with the PP7RLP-ZsGreenI 2X lentiviral particles alone, at a dose of 10 pg p24/cell.

Transduction by the lentiviral particles is carried out in the presence of 8 µg/mL of Polybrene®. A cell defence mechanism inhibitor, BX795 (Invivogen), is used at a concentration of 6 µM in the case of the MS2/PP7(NC)-RLP 12X 2X, MS2RLP-mCherry 12X and PP7RLP-ZsGreenI 2X particles. The target cells are recovered at 48 h post-transduction and the percentage of cells expressing ZsGreenI and mCherry is quantified by cytometry (Macs Quant VYB, Miltenyi Biotec).

II. Results

FIG. 44 illustrates the effectiveness of the MS2/PP7(NC)-RLP 12X 2X particles for transfer of RNAs encapsidated by the encapsidation sequences derived from the bacteriophages MS2 and PP7 into HCT116 target cells. The figure shows that the proportion of bifluorescent cells is 97% after transduction of the MS2/PP7(NC)-RLP 12X 2X particles, at a dose of 10 pg p24/cell, and 98% after transduction of the MS2RLP-mCherry 12X and PP7RLP-ZsGreenI 2X particles, at 20 pg p24/cell. Therefore the same order of transduction effectiveness is observed with the MS2/PP7(NC)-RLP 12X 2X particles, for a dose that is half that of MS2/PP7(NC)-RLP 12X 2X.

The target cells transduced by the MS2RLP-mCherry 12X particles alone or PP7RLP-ZsGreenI 2X particles alone have a percentage transduction effectiveness similar to the percentage obtained after transduction of the target cells by the MS2/PP7(NC)-RLP 12X 2X particles for a single fluorescent protein. The results therefore show that the RLP particles are capable of transporting and transferring at least 2 types of RNAs encapsidated by two different systems (PP7 and MS2) in a single transduction of the target cells.

Demonstration of the capacity for transferring different types of RNA directed by two different encapsidation sequences, MS2 and PP7, in a single transduction of one and the same batch of RLP represents a significant gain on the modulation of the types of RNA encapsidated in particular for effective transfer of the CRISPR/Cas9 system. By replacing the RNAs coding the fluorescent reporters with RNAs coding the Cas9 nuclease and for a non-coding guide RNA, this modulation could allow diversification of the genome editing applications using the CRISPR/Cas9 system.

The invention claimed is:

1. A retroviral particle, comprising a protein derived from the Gag polyprotein, an envelope protein, optionally an integrase, and at least two encapsidated non-viral RNAs, the encapsidated non-viral RNAs each comprising an RNA sequence of interest bound to an encapsidation sequence, each encapsidation sequence being recognized by a heterologous binding domain introduced into the protein derived from the Gag polyprotein and/or into the integrase, in which the at least two encapsidated non-viral RNAs differ by their sequence of interest, wherein:

at least one of said sequences of interest of the encapsidated non-viral RNAs comprises a part coding for a nuclease, said nuclease being chosen from the group constituted by a nuclease associated with CRISPR system; and the sequence of interest of the other encapsidated non-viral RNA corresponds to at least one recognition element of a guide RNA.

2. The retroviral particle according to claim 1, in which the nuclease is Cas9.

3. The retroviral particle according to claim 1, which further comprises at least a third encapsidated non-viral RNA having a sequence of interest corresponding to a second recognition element of a guide RNA or to an additional guide RNA.

4. The retroviral particle according to claim 1, comprising a nucleocapsid protein, an envelope protein, optionally an integrase, and at least two encapsidated non-viral RNAs, the encapsidated non-viral RNAs each comprising an RNA sequence of interest bound to an encapsidation sequence, each encapsidation sequence being recognized by a heterologous binding domain introduced into the nucleocapsid protein and/or into the integrase.

5. The retroviral particle according to claim 4, in which the heterologous binding domain is introduced into the nucleocapsid protein, and a second heterologous binding domain may be introduced into the nucleocapsid and/or into the integrase.

6. The retroviral particle according to claim 1, comprising a nucleocapsid protein, an envelope protein, optionally an integrase, and at least two encapsidated non-viral RNAs, the encapsidated non-viral RNAs each comprising an RNA sequence of interest bound to an encapsidation sequence, at least one encapsidation sequence being the stem-loop motif of the MS2 bacteriophage repeated 12 times, said stem-loop motif being recognized by the Coat protein of the MS2 bacteriophage introduced into the nucleocapsid protein.

7. The retroviral particle according to claim 6, wherein the encapsidated non-viral RNAs comprises, as encapsidation sequence, the stem-loop motif of the MS2 bacteriophage repeated 12 times is an RNA coding Cas9, and a second encapsidated non-viral RNA is an RNA corresponding to at least one recognition element of a guide RNA or coding a guide, said encapsidated non-viral RNAs comprising as encapsidation sequence the stem-loop motif of the MS2 bacteriophage repeated 2 times.

8. The retroviral particle according to claim 1, comprising a nucleocapsid protein, an envelope protein, optionally an integrase, and at least two encapsidated non-viral RNAs, the encapsidated non-viral RNAs each comprising an RNA sequence of interest bound to an encapsidation sequence, at least one encapsidation sequence being the stem-loop motif of the PP7 bacteriophage repeated 2 times, said stem-loop motif being recognized by the Coat protein of the PP7 bacteriophage introduced into the nucleocapsid protein.

9. The retroviral particle according to claim 1, in which the heterologous binding domain is introduced into the integrase, and a second heterologous binding domain may be introduced into the nucleocapsid and/or into the integrase.

10. The retroviral particle according to claim 1, which is a lentiviral particle.

11. A composition comprising the particle according to claim 1.

12. A kit for producing particles according to claim 1, comprising:
(i) an expression plasmid comprising at least two different non-viral RNA sequences, each RNA sequence comprising a sequence of interest for which an encapsidation sequence is inserted upstream of, downstream of or within this sequence, or, alternatively, a first and a second expression plasmid each comprising a sequence of interest upstream or downstream of which an encapsidation sequence is inserted, at least one of these sequences of interest coding for a nuclease chosen from a group constituted by nucleases associated with CRISPR system, the other sequence of interest corresponding to at least one recognition element of a guide RNA,
(ii) an encapsidation plasmid coding for a protein derived from the Gag polyprotein and/or a chimeric integrase, comprising a binding domain allowing recognition of an encapsidation sequence, and,
(iii) an envelope plasmid coding for an envelope protein.

13. The kit according to claim 12, further comprising a second encapsidation plasmid coding for:
a protein derived from the wild-type Gag polyprotein, when the first encapsidation plasmid codes for a protein derived from the chimeric Gag polyprotein, and/or
a wild-type integrase, when the first encapsidation plasmid codes for a chimeric integrase.

14. A manufacturing method for producing the particle according to claim 1, comprising a step of co-transfection of cells with:
(i) an expression plasmid comprising at least two different non-viral RNA sequences, each RNA sequence comprising a sequence of interest for which an encapsidation sequence is inserted upstream of, downstream of or within this sequence, or, alternatively, a first and a second expression plasmid each comprising a sequence of interest upstream or downstream of which an encapsidation sequence is inserted, at least one of these sequences of interest coding for a nuclease chosen from a group constituted by nucleases associated with CRISPR system, the other sequence of interest corresponding to at least one recognition element of a guide RNA,
(ii) an encapsidation plasmid coding for a protein derived from the Gag polyprotein and/or a chimeric integrase comprising a binding domain allowing recognition of an encapsidation sequence, and,
(iii) an envelope plasmid coding for an envelope protein; and recovery of the supernatant from the transfected cells comprising a plurality of the particle.

15. The method according to claim 14, in which the step of co-transfection is further carried out with a second encapsidation plasmid coding for:
a protein derived from the wild-type Gag polyprotein, when the first encapsidation plasmid codes for a protein derived from the chimeric Gag polyprotein, and/or
a wild-type integrase, when the first encapsidation plasmid codes for a chimeric integrase.

16. A composition obtained by the method according to claim 14.

17. A method for generating in cells a DNA double-strand break, a point mutation, a sequence deletion including gene knock-out, a sequence insertion or gene replacement, comprising transducing the cells with the particle according to claim 1.

* * * * *